United States Patent [19]
Gerald et al.

[11] Patent Number: 5,989,834
[45] Date of Patent: Nov. 23, 1999

[54] USES OF NUCLEIC ACID ENCODING NEUROPEPTIDE Y/PEPTIDE YY (Y2) RECEPTORS NUCLEIC ACID ENCODING

[75] Inventors: Christophe Gerald, Ridgewood; Mary W. Walker, Elmwood Park; Theresa Branchek; Richard L. Weinshank, both of Teaneck, all of N.J.

[73] Assignee: Synaptic Pharmaceutical Corporation, Paramus, N.J.

[21] Appl. No.: 08/687,355

[22] PCT Filed: Feb. 3, 1995

[86] PCT No.: PCT/US95/01469

§ 371 Date: Nov. 26, 1996

§ 102(e) Date: Nov. 26, 1996

[87] PCT Pub. No.: WO95/21245

PCT Pub. Date: Aug. 10, 1995

Related U.S. Application Data

[63] Continuation-in-part of application No. 08/192,288, Feb. 3, 1994, Pat. No. 5,545,549.

[51] Int. Cl.$^6$ ........................ G01N 33/566; G01N 33/567
[52] U.S. Cl. .......................... 435/7.2; 435/7.1; 435/7.21
[58] Field of Search .............................. 435/7.1, 7.2, 7.21

[56] References Cited

U.S. PATENT DOCUMENTS

| | | |
|---|---|---|
| 5,026,685 | 6/1991 | Boublik et al. . |
| 5,328,899 | 7/1994 | Boublik et al. . |
| 5,506,258 | 4/1996 | Christophe et al. . |
| 5,516,653 | 5/1996 | Bard et al. . |
| 5,545,549 | 8/1996 | Gerald et al. . |
| 5,571,695 | 11/1996 | Selbie et al. . |
| 5,602,024 | 2/1997 | Gerald et al. . |

FOREIGN PATENT DOCUMENTS

| | | |
|---|---|---|
| 2037433 | 10/1991 | Canada . |
| 2134428 | 10/1994 | Canada . |
| 0355793 | 2/1990 | European Pat. Off. . |
| 0355794 | 2/1990 | European Pat. Off. . |
| 6-116284 | 4/1994 | Japan . |
| 9200079 | 1/1992 | WIPO . |
| 9309227 | 5/1993 | WIPO . |
| 9400486 | 1/1994 | WIPO . |
| 9422467 | 10/1994 | WIPO . |
| 9500161 | 1/1995 | WIPO . |
| 9614331 | 5/1996 | WIPO . |
| 9623809 | 8/1996 | WIPO . |
| 9717440 | 5/1997 | WIPO . |
| 9737998 | 10/1997 | WIPO . |
| 9748406 | 12/1997 | WIPO . |

OTHER PUBLICATIONS

Weinberg, D.H. et al. J. Biol. Chem. 271(28):16435–16438 (1996).
Herzog, H. et al. PNAS 89:5794–5798 (1992).
Wahlestedt, c. et al. Life Sciences. 50:7–12 (1991).
Whitcomb, D.C. et al. Am. J. Physiol. 259:G687–G691 (1990).
Lundberg, J.M. et al. J. Neuroscience. 4(9):2376–2386 (1984).
Wahlestedt, C. et al. Life Science. 50:7–12 (1991).
Narvaez, J.A. et al. Neuroscience Letters. 140:273–276 (1992).
Blasquez, C. et al. Brain Research. 596:163–168 (1992).
Kotz, C.M. et al. Brain Research. 631:325–328 (1993).
Gehlert, D.R. et al. Life Science. 55(8):551–562 (1994).
Gerald, C. et al. Nature. 382:168–171 (1996).
Larhammar, D., et al., "Cloning and Functional Expression of a Human Neuropeptide Y/Peptide YY Receptor of the Y1 Type" *J. Biol. Chem.* (1992) 267(16): 10935–10938;.
Sasaki, et al., "Cloning And Expressing Of A complementary DNA Encoding A Bovine Adrenal Angiotensin II Type–1 Receptor" *Nature* (1991) 351: 230–233;.
Inui, A. et al. Science. 611:350–352 (1990).
Wahlestedt, C. et al. Academy of Science. 611:7–12 (1990).
Sheikh, S.P. et al. J. Biol. Chem. 266:23959–23966 (1991).
Wahlestedt, C., et al., "Modulation of Anxiety and Neuropeptide Y–Y1 Receptors by Antisense Oligodeoxy nucleotides" *Science* (1993) 259(5094): 528–531; and.
Yan, H., et al., EMBL Data Library Accession No. G02301 (Jun. 6, 1997).
Kluxen, et al., "Expression Cloning Of A Rat Brain Somatostatin Receptor cDNA" *PNAS* (1992) 89: 4618–4622;.
Sheikh, S.P., et al., Binding of Monoiodinated Neuropeptide Y to Hippocampal Membranes and Human Neuroblastoma Cell Lines *J. Biol. Chem.* (1989) 264(12): 6648–6654;.
Wallace, et al., Oligonucleotide Probes For The Screening Of Recombinant D78 89++8u9 nh NA Libraries (1987) *Methods in Enzymology* 152: 432–442;.
Xie, et al., "Expression Cloning of G–Protein–Coupled Opioid Receptors" *PNAS* (1992) 89: 4124–4128.
Aguzzi, A., et al., "Transgenic and Knock–out Mice: Models of Neurological Disease" *Brain Pathol.* (1994) 4(1): 3–20;.

(List continued on next page.)

*Primary Examiner*—Anthony C. Caputa
*Assistant Examiner*—Stephen Gucker
*Attorney, Agent, or Firm*—John P. White; Cooper & Dunham LLP

[57] ABSTRACT

This invention provides isolated nucleic acid molecules encoding a human and a rat Y2 receptor, an isolated protein which is a human or rat Y2 receptor, vectors comprising an isolated nucleic acid molecule encoding a human or rat Y2 receptors, mammalian cells comprising such vectors, antibodies directed to the human or rat Y2 receptor, nucleic acid probes useful for detecting nucleic acid encoding human or rat Y2 receptors, antisense oligonucleotides complementary to any sequences of a nucleic acid molecule which encodes a human or rat Y2 receptor, pharmaceutical compounds related to human or rat Y2 receptors, and nonhuman transgenic animals which express DNA a normal or a mutant human or rat Y2 receptor. This invention further provides methods for determining ligand binding, detecting expression, drug screening, and treatment involving the human or rat Y2 receptor.

14 Claims, 35 Drawing Sheets

OTHER PUBLICATIONS

Herzog, H., et al., "Neuropeptide–Y Y1 Receptor Gene Polymorphism: Cross–Sectional Analyses in Essential Hypertension and Obesity" *Biochem. Biophys. Res. Commun.* (1993) 196(2): 902–906;.

Oliveira, L., et al., "A Common Motif In G–Protein–Coupled Seven Transmembrane Helix Receptors" *Journal of Computer–Aided Molecular Design* (1993) 7(6): 649–658;.

Voisin, T., et al., "Peptide YY Receptors in the Proximal Tubule PKSV–PCT Cell–Line Derived From Transgenic Mice–Relation With Cell–Growth" *J. Of Biol. Chem.* (1993) 268(27): 20547–20554;.

FIGURE 1

```
   1 GACTCTTGTGCTGGTTGCAGGCCAAGTGGACCTGTACTGAAAATGGGTCCAATAGGTGCA     60
  61 GAGGCTGATGAGAACCAGACAGTGGAAGAAATGAAGGTGGAACAATACGGGCCACAAACA    120
 121 ACTCCTAGAGGTGAACTGGTCCCTGACCCTGAGCCAGAGCTTATAGATAGTACCAAGCTG    180
 181 ATTGAGGTACAAGTGTGTTCTCATATTGGCCTACTGCTCCATCATCTTGCTTGGGTAATT    240
 241 GGCAACTCCTTGGTGATCCATGTGGTGGTGGCAGATCAAATTCAAGAGCATGCGCACAGTAACCAAC    300
 301 TTTTCATTGCCAATCTGGCTGTGTGGCAGATCTTTTGGTGAACACTCTGTGTCTACCGTTC    360
 361 ACTCTTACCTATACCTTAATGGGGAGTGGAAAATGGGTCCTGTCCTGTGCCACCTGGTG    420
 421 CCCTATGCCCAGGGCCTGCAGTACAAGTATCCACATCACCTTGACAGTAATGCCCCTG    480
 481 GACCGGCACAGGTGCATCGTGTTGGGGCATGTCCCTGCTGGCAAGTCCCCTGCCATCTTC    540
 541 CTGATTATTGGCTTGGCCTGATTCGCTGAGATCATCCCGGACTTTGAGATTGTGGCCTGTACTGAAAAG    600
 601 CGGGAGTATTCGCTGAGGAGAGAGCATCTATGGCACTGTCTCTATAGTCTTCTTCCTTGATC    660
 661 TGGCCTGGCCAGAGAGAGCATCTATGGCACTGTCTCTATAGTCTTCTTCCTTGTTGATC    720
 721 TTGTATGTTTTGCCCTCTGGGCCATTATATCATTCCTACACTCGCATTTGGAGTAAATTG    780
 781 AAGAACCATGTCAGTCCTGGTGTGTGACATTGACAGCCAGTCCTGGTCAGCTGGCTGCCCTCTCCATGCC    840
 841 ACCAAAATGCTGGTGCCGTTGACATTGACAGCCAGTCCTGGTGTTTGCGGTCAGCTGGCTGCCCTCTCCATGCC    900
 901 TTCCAGCTTGCCTGCCACATCATCGCCATGTGCCAATCCCCACTTTGCCAATCCCCTTCTCTATGGC    960
 961 TTCACAGTGTTCCACATCATCGCCATGTGCCAATCCCCTTCTCTATGGC   1020
1021 TGGATGAACAGCAACTACAGAAAGGCTTTCTCCGCCCTTCCGCTGTGAGCAGCGGTTG   1080
1081 GATGCCATTCACTCTGAGGTGTCCGTGACATTCAAGGCTAAAAAGAACCTGGAGGTCAGA   1140
1141 AAGAACAGTGGCCCCAATGACTCTTTCACAGAGCTACCAATGTCTAAGGAAGCTGTGGT   1200
1201 GTGAAATGTATGGATGAATTCTGACCAGAGCTATGAATTCTGGTTGATGGCGGCTCACAA   1260
1261 GTGAAAACTGATTTCCCATT   1280
```

Sequence positions labeled on left (6, 26, 46, 66, 86, 106, 126, 146, 166, 186, 206, 226, 246, 266, 286, 306, 326, 346, 366, 381) and on right (7, 27, 47, 67, 87, 107, 127, 147, 167, 187, 207, 227, 247, 267, 287, 307, 327, 347, 367).

FIGURE 3A

```
         .         .         .         .         .
1002 ATGGGTCCAATAGGTGCAGAGGCTGATGAGAACCAGACAGTGGAAGAAAT 1051
                                      ||||||||| |||||
 197 ..........................ATGAATTCAACACATTATTTC   216

.         .         .         .         .
1052 GAAGGTGGAACAATACGGGCCACAAACAACTCCTAGAGGTGAACTGGTCC 1101
     ||||  |   | | ||   ||  || | |  |  ||| |||||||||
 217 CCAGGTTGAAAATCATTCAGTCCACTCTAATTTCTCAGAGAATGCCC    266

.         .         .         .         .
1102 CTGACCCTGAGCCAGAGCTTATAGATAGTACCAAGCTGATTGAGGTACAA 1151
        ||  |||  | |  |    |  |||    |||  ||||||
 267 AGCTTCTGGCTTTTGAAAATGATGATTGTCATCTGCCCTTGCCATGATA  316

.         .         .         .         .
1152 GTTGTTCTCATATTGGCCTACTGCTCCATCATCTTGCTTGGGTAATTGG 1201
      |||||   ||  ||| ||  ||||||| |||||||  ||||||
 317 TTTACCTTAGCTCTTGCTTATGGAGCTGTGATCATTCTTGGTCTCTGG   366

.         .         .         .         .
1202 CAACTCCTTGGTGATCCATGTGGTGATCAAATTCAAGAGCATGCCACAG 1251
     ||| ||||||   ||||| ||  |||||||||  || || ||||||
 367 AAACCTGGCCTTGATCATAATCATCTTGAAACAAAAGGAGATGAGAAATG 416

.         .         .         .         .
1252 TAACCAACTTTTTCATTGCCAATCTGGCTGTGGCAGATCTTTTGGTGAAC 1301
     |||||| ||| ||||| | | |  ||| |||||| |||  ||  ||
 417 TTACCAACATCCCTGATTGTGAACCTTTCCTTCTCAGACTTGCTGTTGCC 466
```

FIGURE 3B

```
1302 ACTCTGTGTCTACCGTCTTCACTCTTACCTATACCTTAATGGGGGAGTGGAA 1351
     || |||||| ||    |||  ||  || ||  ||||||| |||||
 467 ATCATGTGTCTCCCCTTACATTGTCTACACATTAATGGACCACTGGGT      516

1352 AATGGGTCCTGTCCTGTGCCACCTGGTGCCCATGCCCAGGGCCTGGCAG    1401
      |||||| |||| ||||  || ||||  |||  |||||||| ||||
 517 CTTTGGTGAGGCGATGTGTAAGTTGAATCCTTTGTGCAATGTGTTTCAA    566

1402 TACAAGTATCCACAATCACCTTGACAGTAATTGCCCTGACCGGCACAGG    1451
         ||||| ||| ||||| |||  |||  ||||||| |||  |||||
 567 TCACTGTGTCCATTTCTCTCGGTTCTCATTGCTGTGGAACGACATCAG    616

1452 TGCATCGTCTACCACCTAGAGAGCAAGATCTCCAAGCGAATCAGCTTCCT    1501
     |||| |||  || ||||  ||    |||||  ||||  || |||
 617 CTGATAATCAACCCTCGAGGGTGGAGAGACCAAATAATAGACATGCTTATGT    666

1502 GATTATTGGCTTGGCCTGGGCATCAGTGCCCTGCTGGCAAGTCCCCTGG    1551
      || ||||| ||||  ||  |||    ||||| ||  ||||| |||
 667 AGGTATTGCTGTGATTGGGTCCTTGCTG..TGGCTTCTTCTTTGCCTTT    714

1552 CCATCTTCCGGGAGTATTCGCTGATTGAGATCATCCCGGACTTTGAGATT    1601
     ||  ||  || |||| || ||    |||  |||  |||||  |||
 715 CCTGATCTACCAAGTAATGACTGA.TGAGCCGTTCCAAAATGTAACACTT    763
```

FIGURE 3C

```
1602  GTGGCCTGTACTGAAAAGTGGCCTGGGCGAGGAGAA..........GAGCAT  1642
          ||   ||  ||                              ||||||
 764  GATGCGTACAAAGACAAATACGTGTGCTTTGATCAATTTCCATCGGACTC   813

1643  CTATGGCACTGTCTATAGTCTTTCTTCCTGTTGATCTTGTATGTTTTGC    1692
       ||||   |||||   ||||    |||  ||| ||   || ||||
 814  TCATAGGTTGTCTTATACCACTCCTCCTTGGTGCTGCAGTATTTGGTC     863

1693  CTCTGGGCATTATATCATTTTCCTACACTCGCATTT......GGAGTA     1734
        ||   || ||  ||||||   |||  ||  |   ||       ||||
 864  CACTTTGTTTTATATTTATTTGCTACTTCAAGATATATATACGCCTAAAA   913

1735  AATTGAAGAACCATGTCAGTCCTGGAGCTGCAAATGACCACTACCATCAG   1784
         ||||| ||||  ||   ||||    |||||| ||  |  ||   |||
 914  AGGAGAAACAACATGATGGACAAGATGAGAGACAATAAGTACAGGTCCAG    963

1785  CGAAGGCAAAA.AACCACCAAAATGCTGGTGTGGTGGTGGTGGTGTTTG    1833
       |||||||||| ||||||||||||||||||||||||| ||||||||||
 964  TGAAACCAAAAGAATCAATATCATGCTGCTCCCATTGTGGTAGCATTTG   1013

1834  CGGTCAGCTGGCTGCCTGGCCCTTCCAGCTTGCCGTTGACATTGAC      1883
       |||  |  |||||||| |||  |||||||||     ||  |||||
1014  CAGTCTGCTGGCTCCCTCCTTACCATCTCTTTAACACTGTGTTTGATTGGAAT  1063
```

FIGURE 3D

```
1884 AGCCAGGTCCTGGACCTGAAGGAGTACAAACTCATCTTCACAGTGTTCCA 1933
       ||| ||    ||  |  ||||    ||||| ||  ||| | ||||  ||
1064 CATCAGATCATTGCTACCTGCAACCACAATCTGTTATTCCTGCTCTGCCA 1113

1934 CATCATCGCCATGTGCTCCACTTTGCCAATCCCCCTTCTCTATGGCTGGA 1983
     | ||| || ||    |||||||| ||| ||  ||||| |||| |||  |
1114 CCTCACACAGCAATGATATCCACTTGTGTCAACCCCATATTTTATGGGTTCC 1163

1984 TGAACAGCAACTACAGAAAGGCTTTCCTCTCGGCCCTTCCGC....TGTGAG 2030
     |||||| |||||| || ||| ||| |    | |||    ||     ||  |
1164 TGAACAAAAACTTCCAGAGAGACTTGCAGTTCTTCTTCTTCAACTTTTGTGAT 1213

2031 CAGCGGTTGGATGCCATTCACTCTGAGGTGTCCGTGACATTCAAG..... 2075
      ||| || ||| ||  ||| ||  |  | ||  | || |  ||
1214 TTCCGGTCTCGGGATGATGATTATGAAACAATAGCCATGTCCACGATGCA 1263

2076 ........GCTAAAAAGAACCTGGAGGTCAGAGAAGAACAGTGGC..CCCA 2115
             |||| ||||  || ||| ||  |||  || || ||   | ||
1264 CACAGATGTTTCCAAAACTTCTTTGAAGCAAGCCCCAGTCGCATTTA 1313

2116 ATGACTCTTTCACAGAGGCTACCAATGTCTAA...... 2147
     |  || ||   || ||
1314 AAAAAATCAACAACAATGATGATAATGAAAAATCTGA 1351
```

FIGURE 4A

| FIGURE 4A |
|-----------|
| FIGURE 4B |

```
  1  MGPIGAEADENQTVEEMKVEQYGPQTTPRGELVPDPEPELIDSTKLIEVQ    50
     |...:.|:.|:.       .::......:   :|::       ...:
  1  MNSTLFSQVENHSVH.....SNFSEKNAQLLAFEND......DCHLPLAMI   40

51  VVLILAYCSIILLGVIGNSLVIHVVIKFKSMRTVTNFFIANLAVADLLVN   100
     :|||||||:.:|||    :|     ||.:.|:.|||..:.||:....||||
 41  FTLALAYGAVIILGVSGNLALIIIILKQKEMRNVTNILIVNLSFSDLLVA   90

101  TLCLPFTLTYTLMGEWKMGPVLCHLVPYAQGLAVQVSTITLTVIALDRHR   150
     .:|||||||:.||||||.   :|..::.|    ||.:...|..|.::||..||
 91  IMCLPFTFVYTLMDHWVFGEAMCKLNPFVQCVSITVSIFSLVLIAVERHQ   140

151  CIVYHLESKISKRISFLIIGLAWGISALLASPLAIFREYSLIEIIPDFEI   200
     |.:.:|..:.||:.|:.|.:    |:   |.:..   ||:.|:.
141  LIINPRGWRPNNRHAYVGIAVIWVLAVASSLPFLIYQVMT.DEPFQNVTL   189
```

FIGURE 4B

```
201 VACTEKW........PGEEKSIYGTVYSLSSLLILYVLPLGIISFSYTRIW 243
       |::|:      ...:  .:|:     |::  | .:|  ::| ::|
190 DAYKDKYVCFDQFPSDSHRLSYTTLL....LVLQYFGPLCFIFICYFKIY 235

244 SKLK..NHVSPGAANDHYHQRRQKTTK.MLVCVVVVFAVSWLPLHAFQLA 290
    :||  |::   .  ::|:   |..|   |:::||:||:||||  |: .
236 IRLKRRNNMMDKMRDNKYRSSETKRINIMLLSIVVAFAVCWLPLTIFNTV 285

291 VDIDSQVLDLKEYKLIFTVFHIIAMCSTFANPLLYGWMNSNYRKAF.... 336
    .| :  ||| :|  || ||  |::||:|| .|:::|.|::..:
286 FDWNHQIIATCNHNLLFLLCHLTAMISTCVNPIFYGFLNKNFQRDLQFFF 335

337 .LSAFRCEQR......LDAIHSEVSVT.FKAKKNLEVRK..NSGPNDSFT 376
     ::: :        ::|::||  ::|. |:  |:. ::|
336 NFCDFRSRDDDYETIAMSTMHTDVSKTSLKQASPVAFKKINNNDDNEKI* 385

377 EATNV* 381
```

| FIGURE 8A |
| FIGURE 8B |
| FIGURE 8C |
| FIGURE 8D |
| FIGURE 8E |

FIGURE 8A

```
            -200                   -180                   -160
             .          .           .          .           .
GTTGTTAACAGACTCGTGTAAAGGATTTGCTTTATGGAGCTTTTATGAGATCTGTGGTGT

-140                   -120                   -100
             .          .           .          .           .
GATGAATCAGAACACAGCTACGCAGAGGAGCTCAGCCTAAAACTAAATCAACCCCTTTAGG

-80                    -60                    -40
             .          .           .          .           .
ATGGTTCTCTGTTTCACTAACTTTTTTTAATGTCCGTTTTCTGTTATAGATTCTTGTGCTA

-20                     1                     20
             .          .           .          .           .
TCTGCAGGCCAAAATTGGAACCTGAGGTGAAAGATGGGCCCATTAGGTGCAGAGGCAGATGAG
                                    M  G  P  L  G  A  E  A  D  E 40                    60                    80
             .          .           .          .           .
AATCAAAACTGTAGAAGTGAAAGTGAACTCTATGGTCGGAGCCCCACCTCCTAGAGGT
 N  Q  T  V  E  V  K  V  E  L  Y  G  G  S  G  P  T  T  P  R  G
```

FIGURE 8B

```
     100         120         140
      .           .           .
GAGTTGCCCCCTGATCCAGAGCCGGAGCTCATAGACAGCACCAAACTGGTTGAGGTGCAG
 E  L  P  P  D  P  E  P  E  L  I  D  S  T  K  L  V  E  V  Q 160         180         200
      .           .           .
GTGGTCCTTATACTGGCCCTATTGTTCCATCATCTTGCTGGGCGTAGTTGGCAACTCTCTG
 V  V  L  I  L  A  Y  C  S  I  I  L  L  G  V  V  G  N  S  L 220         240         260
      .           .           .
GTAATCCATGTGGTGATCAAATTCAAGAGCATGCGCACAGTAACCAACTTTTTTATTGCC
 V  I  H  V  V  I  K  F  K  S  M  R  T  V  T  N  F  F  I  A 280         300         320
      .           .           .
AACCTGGCTGTGGCGGATCTTTTGGTGAACACCCTGTGCCTGCCATTCACTCTTACCTAT
 N  L  A  V  A  D  L  L  V  N  T  L  C  L  P  F  T  L  T  Y 340         360         380
      .           .           .
ACCTTGATGGGGGAGTGGAAAATGGGTCCAGTTTTGTGCCATTTGGTGCCCTATGCCCAG
 T  L  M  G  E  W  K  M  G  P  V  L  C  H  L  V  P  Y  A  Q
```

FIGURE 8C

```
                               400                    420                    440
                                 .                      .                      .
                        GGTCTGGCAGTACAAGTGTCCACAATAACTTTGACAGTCATTGCTTTGGACCGACACGT
                         G  L  A  V  Q  V  S  T  I  T  L  T  V  I  A  L  D  R  H  R 460                    480                    500
                                 .                      .                      .
                        TGCATTGTCTACCACCTGGAGAGCAAGATCTCCAAGCAAATCAGCTTCCTGATTATTGGC
                         C  I  V  Y  H  L  E  S  K  I  S  K  Q  I  S  F  L  I  I  G 520                    540                    560
                                 .                      .                      .
                        CTGGCCGTGGGGTGTCAGCCGCTCTGCTGGCAAGTCCCCTTGCCATCTTCCGGGAGTACTCA
                         L  A  W  G  V  S  A  L  L  A  S  P  L  A  I  F  R  E  Y  S 580                    600                    620
                                 .                      .                      .
                        CTGATTGAGATTATTCCTGACTTTGAGATTGTAGCCTGTACTGAGAAATGGCCCGGGGAG
                         L  I  E  I  I  P  D  F  E  I  V  A  C  T  E  K  W  P  G  E 640                    660                    680
                                 .                      .                      .
                        GAGAAGAGTGTGTACGGTACAGTCTACAGCCTTTCCACCCTGCTAATCCTCTACGTTTTG
                         E  K  S  V  Y  G  T  V  Y  S  L  S  T  L  L  I  L  Y  V  L
```

FIGURE 8D

```
     700                 720                 740
CCTCTGGGCATCATATATCTTTCTCCTACACCCGGATCTCTGGAGTAAGCTAAAGAACCACGTT
 P  L  G  I  I  S  F  S  Y  T  R  I  W  S  K  L  K  N  H  V 760                 780                 800
AGTCCTGGAGCTGCAAGTGACCATTACCATCAGCGAAGGCACAAAACGACCAAAATGCTC
 S  P  G  A  A  S  D  H  Y  H  Q  R  R  H  K  T  T  K  M  L 820                 840                 860
GTGTGCGTGGTAGTGGTGTTTGCAGTCAGTCAGTCTGGCCTGCCCCCTCCATGCCTTCCAACTTGCT
 V  C  V  V  V  F  A  V  S  W  L  P  L  H  A  F  Q  L  A 880                 900                 920
GTGGACATCGACAGCCATGTCCTGGACCTGAAGGAGTACAAACTCATCTTCACCGTGTTC
 V  D  I  D  S  H  V  L  D  L  K  E  Y  K  L  I  F  T  V  F 940                 960                 980
CACATTATTGCCGATGTGCTCCACCTTCGCCAACCCCCTTCGCCAACCCCCTTCTCTATGGCTGGATGAACAGC
 H  I  I  A  M  C  S  T  F  A  N  P  L  L  Y  G  W  M  N  S
```

FIGURE 8E

```
                  1000                    1020                    1040
                    .                       .                       .
AACTACAGAAAAAGCTTTCCTCTCTCAGCCTTCCGCTGTGAGCAGAGGTTGGATGCCATTCAC
 N  Y  R  K  A  F  L  S  A  F  R  C  E  Q  R  L  D  A  I  H
                  1060                    1080                    1100
                    .                       .                       .
TCGGAGGTGTCCATGACCTTCAAGGCTAAAAAGAACCTGGAAGTCAAAAAGAACAATGGC
 S  E  V  S  M  T  F  K  A  K  K  N  L  E  V  K  K  N  N  G
                  1120                    1140                    1160
                    .                       .                       .
CTCACTGACTCTTTTTCAGAGGCCACCAACGTGTAAGAATGCTGTGAAAGTACGTGGGTA
 L  T  D  S  F  S  E  A  T  N  V  *
                  1180                    1200                    1220
                    .                       .                       .
AATTGCGACCAGAGTTGCCAACCTGGTTAGGGAAGGTTTTCTGGCTAGTGCATGCCACCT
                  1240                    1260                    1280
                    .                       .                       .
CCCATTGTATTGACCCTAAAAAGCATCAGAGTGGAAGCCCCAGCGGTATTGTTCCTGGAAA
                  1300                    1320                    1340
                    .                       .                       .
ACTGGCTGGAAGAATGAGGAGAAAATAAACAGATTGCTGTGGCCAACGTTCTGAT
```

FIGURE 9A

| FIGURE 9A |
|---|
| FIGURE 9B |
| FIGURE 9C |
| FIGURE 9D |

```
         -50              -30              -10            1
          .                .                .             .
         TTTCTGTTATAGATTCTTGTGTGCTATCTGCAGGCCAAAATTGGAACTGAGGTGAAGATGGGC
                                                                   M  G 10               30               50
          .                .                .
         CCATTAGGTGCAGAGGCAGATGAGAATCAAACTGTAGAAGTGAAAGTGGAATTCTATGGG
         P  L  G  A  E  A  D  E  N  Q  T  V  E  V  K  V  E  F  Y  G 70               90              110
          .                .                .
         TCGGGGCCCACCACTCCTAGAGGTGAGTTGCCCCCTGATCCAGAGCCGGAGCTCATAGAC
         S  G  P  T  T  P  R  G  E  L  P  P  D  P  E  P  E  L  I  D 130              150              170
          .                .                .
         AGCACCAAAACTGGTTGAGGTGCAGGTGGTCCTTATACTGGCCTATTGTTCCATCATCTTG
         S  T  K  L  V  E  V  Q  V  V  L  I  L  A  Y  C  S  I  I  L 190              210              230
          .                .                .
         CTGGGCGTAGTTGGCAACTCTCTGGTAATCCATGTGGTGATCAAATTCAAGAGCATGCGC
         L  G  V  V  G  N  S  L  V  I  H  V  V  I  K  F  K  S  M  R
```

FIGURE 9B

```
            250                       270                       290
             .                         .                         .
ACAGTAACCAACTTTTTTATTGCCAACCTGGCTGTGGCGGATCTTTTGGTGAACACCCTG
 T  V  T  N  F  F  I  A  N  L  A  V  A  D  L  L  V  N  T  L 310                       330                       350
             .                         .                         .
TGCCTGCCATTCACTCTTACCTATACCTTGATGGGGAGTGGAAAATGGGTCCAGTTTTG
 C  L  P  F  T  L  T  Y  T  L  M  G  E  W  K  M  G  P  V  L 370                       390                       410
             .                         .                         .
TGCCATTTGGTGCCCTATGCCCAGGGTCTGGCAGTACAAGTGTCCACAATAACTTTGACA
 C  H  L  V  P  Y  A  Q  G  L  A  V  Q  V  S  T  I  T  L  T 430                       450                       470
             .                         .                         .
GTCATTGCTTTGGACCGACATCGTTGCATTGTCTACCACCTGGAGAGCAAGATCTCCAAG
 V  I  A  L  D  R  H  R  C  I  V  Y  H  L  E  S  K  I  S  K 490                       510                       530
             .                         .                         .
CAAATCAGCTTCCTGATTATTGGCCTGGCGGTGTCAGCGCTGCTGGCAAGTCCC
 Q  I  S  F  L  I  I  G  L  A  W  G  V  S  A  L  L  A  S  P
```

FIGURE 9C

```
         550                570                590
CTTGCCATCTTCCGGGAGTACTCACTGATTGAGATTATTCCTGACTTTGAGATTGTAGCC
 L  A  I  F  R  E  Y  S  L  I  E  I  I  P  D  F  E  I  V  A 610                630                650
TGTACTGAGAAATGGCCCGGGGAGGAGAAGAGTGTGTACGGTACAGTCTACAGCCTTTCC
 C  T  E  K  W  P  G  E  E  K  S  V  Y  G  T  V  Y  S  L  S 670                690                710
ACCCTGCTAATCCTTCTACGTTTGCCTCTGGGCATCATATCTTTCTCCTACACCCGGATC
 T  L  L  I  L  Y  V  L  P  L  G  I  I  S  F  S  Y  T  R  I 730                750                770
TGGAGTAAGCTAAAGAACCACGTTAGTCCTGGAGCTGCAAGTGACCATTACCATCAGCGA
 W  S  K  L  K  N  H  V  S  P  G  A  A  S  D  H  Y  H  Q  R 790                810                830
AGGCACAAAATGACCAAAATGCTCGTGTGCGTAGTGGTGTTTGCAGTCAGCTGGCTG
 R  H  K  M  T  K  M  L  V  C  V  V  V  F  A  V  S  W  L
```

FIGURE 9D

```
         850                870                890
          .                  .                  .
CCCCTCCATGCCTTCCAACTTGCTGTGGACATCGACAGCCATGTCCTGGACCTGAAGGAG
 P  L  H  A  F  Q  L  A  V  D  I  D  S  H  V  L  D  L  K  E 910                930                950
          .                  .                  .
TACAAACTCATCTTCACCGTGTTCCACATTATTGCGATGTGCTCCACCTTCGCCAACCCC
 Y  K  L  I  F  T  V  F  H  I  I  A  M  C  S  T  F  A  N  P 970                990               1010
          .                  .                  .
CTTCTCTATGGCTGGATGAACAGCAACTACAGAAAAGCTTTCCTCTCCAGCCTTCCGCTGT
 L  L  Y  G  W  M  N  S  N  Y  R  K  A  F  L  S  A  F  R  C 1030               1050               1070
          .                  .                  .
GAGCAGAGGTTGGATGCCATTCACTCGGAGGTGTCCATGACCTTCAAGGCTAAAAAGAAC
 E  Q  R  L  D  A  I  H  S  E  V  S  M  T  F  K  A  K  K  N 1090               1110               1130
          .                  .                  .
CTGGAAGTCAAAAAGAACAATGGCCTCACTGACTCTTTTTCAGAGGCCACCAACGTGTAA
 L  E  V  K  K  N  N  G  L  T  D  S  F  S  E  A  T  N  V  *
```

FIGURE 10A

| | FIGURE 10A |
|---|---|
| | FIGURE 10B |
| | FIGURE 10C |
| | FIGURE 10D |

```
Hum Y2  ATGGGTCCAATAGTGCAGAGGCTGATGAGAACCAGACAGTGGAAGAAAT   50
Rat Y2a ATGGGCCCATTAGTGCAGAGGCAGAGATGAGAATCAAACTGTAGAAGTGAA  50
Rat Y2b ATGGGCCCATTAGTGCAGAGGCAGATGAGAATCAAACTGTAGAAGTGAA   50

Hum Y2  GAAGGTGGAACAATACGGGCCACAAACAACTCCTAGAGGTGAACTGGTCC  100
Rat Y2a AGTGGAACTCTATGGGTCGGGGCCCACCACTCCTAGAGGTGAGTTGCCCC  100
Rat Y2b AGTGGAATTCTATGGGTCGGGGCCCACCACTCCTAGAGGTGAGTTGCCCC  100

Hum Y2  CTGACCCTGAGCCAGAGCTTATAGATAGTACCAAGCTGATTGAGGTACAA  150
Rat Y2a CTGATCCAGAGACCGGAGCTCATAGACACAGCACCAAACTGGTTGAGGTGCAG  150
Rat Y2b CTGATCCAGAGACCGGAGCTCATAGACACAGCACCAAACTGGTTGAGGTGCAG  150

Hum Y2  GTTGTTCTCATATTGGCCTACTGCTCCATCATCTTGCTTGGGTAATTGG   200
Rat Y2a GTGGTTCCTTATACTGGCCTATTGTTCCATCATCTTGCTCGGCTAGTTGG  200
Rat Y2b GTGGTTCCTTATACTGGCCTATTGTTCCATCATCTTGCTGGGCTAGTTGG  200

Hum Y2  CAACTCCTTGGTGATCCATGTGGTGATCAAATTCAAGAGCATGCGCACAG  250
Rat Y2a CAACTCCTCTGGTAATCCATGTGGTGATCAAATTCAAGAGCATGCGCACAG  250
Rat Y2b CAACTCTCTGGTAATCCATGTGGTGATCAAATTCAAGAGCATGCGCACAG  250

Hum Y2  TAACCAACTTTTTCATTGCCAATCTGGCTGTGCCAGATCTTTTGGTGAAC  300
Rat Y2a TAACCAACTTTTTTTATTGCCAACCTGGCTGTGCTGGCGATCTTTTGGTGAAC  300
Rat Y2b TAACCAACTTTTTTTATTGCCAACCTGGCTGTGCCGGATCTTTTGGTGAAC  300

Hum Y2  ACTCTGTCTACCGTTCACTCTTACCTATACCCTTAATGGGGAGTGGAA   350
Rat Y2a ACCCTGCCTGCCATTCACTCTTACCTTACCCTTGATGGGGAGTGGAA    350
Rat Y2b ACCCTGCCTGCCATTCACTCTTACCTATACCCTTGATGGGGAGTGGAA   350
```

FIGURE 10B

```
Hum  Y2    AATGGGTCCTGTCCTGTGCCACCTGGTGCCTGCCCTATGCCCAGGGCCTGGCAG   400
Rat  Y2a   AATGGGTCCAGTTTGTGCCAGTTTGGTGCCTGCCCTATGCCCAGGTCTGGCAG    400
Rat  Y2b   AATGGGTCCAGTTTTGTGCCATTTGGTGCCTGCCCTATGCCCAGGTCTGGCAG    400

Hum  Y2    TACAAGTATCCACAATCACCTTGACAGTAATTGCCCTGGACCGGCACAGG       450
Rat  Y2a   TACAAGTGTCCACAATAACTTTGACAGTCATTGCTTTGGACCGACATCGT       450
Rat  Y2b   TACAAGTGTCCACAATAACTTTGACAGTCATTGCTTTGGACCGACATCGT       450

Hum  Y2    TGCATCGTCTACCACCTAGAGAGCAAGATCTCCAAGCGAATCAGCTTCCT       500
Rat  Y2a   TGCATTGTCTACCACCTGGAGAGCAAGATCTCCAAGCAAATCAGCTTCCT       500
Rat  Y2b   TGCATTGTCTACCACCTGGAGAGCAAGATCTCCAAGCAAATCAGCTTCCT       500

Hum  Y2    GATTATTGGCTTGGCCTGGGCATCAGTGCCCTGCTGGCAAGTCCCCCTGG       550
Rat  Y2a   GATTATTGGCCTGGCCTGGGCGTGTCAGCGTGTCAGCGCTGCTGGCAAGTCCCCCTTG   550
Rat  Y2b   GATTATTGGCCTGGCCTGGGCGTGTCAGCGTGTCAGCGCTGCTGGCAAGTCCCCCTTG   550

Hum  Y2    CCATCTTCCGGGAGTATTCGCTGATTGAGATCATCCCGGACTTTGAGATT      600
Rat  Y2a   CCATCTTCCGGGAGTACTCACTGATTGAGATTATTCCTGACTTTGAGATT      600
Rat  Y2b   CCATCTTCCGGGAGTACTCACTGATTGAGATTATTCCTGACTTTGAGATT      600

Hum  Y2    GTGGCCTGTACTGAAAAGTGGCCTGGCGAGGAGAAGAGCATCTATGGCAC      650
Rat  Y2a   GTAGCCTGTACTGAGAAATGGCCCGGGGAGGAGGAGAAGAGTGTGTACGGTAC   650
Rat  Y2b   GTAGCCTGTACTGAGAAATGGCCCGGGGAGGAGGAGAAGAGTGTGTACGGTAC   650

Hum  Y2    TGTCTATAGTCTTTCTTCCTTGTGATCTTGTATGTTTGCCTCTGGGCA        700
Rat  Y2a   AGTCTACAGCCTTTCCACCCTTGCTAATCCTCTACGTTTTGCCTCTGGCA      700
Rat  Y2b   AGTCTACAGCCTTTCCACCCTTGCTAATCCTCTACGTTTTGCCTCTGGCA      700
```

FIGURE 10C

```
Hum Y2   TTATATCATTTCCTACACTCGCATTGGAGTAAATTGAAGAACCATGTC  750
Rat Y2a  TCATATCTTTCTCCTACACCCGGATCTGGAGTAAGCTAAAGAACCACGTT 750
Rat Y2b  TCATATCTTTCTCCTACACCCGGATCTGGAGTAAGCTAAAGAACCACGTT 750

Hum Y2   AGTCCTGGAGCTGCAAATGACCACTACCATCAGCGAAGGCAAAAACCAC  800
Rat Y2a  AGTCCTGGAGCTGCAAGTGACCATTACCATCAGCGAAGGCACAAAACGAC 800
Rat Y2b  AGTCCTGGAGCTGCAAGTGACCATTACCATCAGCGAAGGCACAAAATGAC 800

Hum Y2   CAAAATGCTGGTGTGTGTGGTGGTGTTGCGGTCAGCTGGCTGCCTC     850
Rat Y2a  CAAAATGCTCGTGTGTGCGTGGTAGTGGTGTTGCAGTCAGCTGGCTGCCCC 850
Rat Y2b  CAAAATGCTCGTGTGCGTGGTGGTAGTGGTGTTGCAGTCAGCTGGCTGCCCC 850

Hum Y2   TCCATGCCTTCCAGCTTGCCGTTGACATTGACAGCCAGGTCCTGGACCTG 900
Rat Y2a  TCCATGCCTTCCAACTTGCTGTGGACATCGACAGCCATGTCCTGGACCTG 900
Rat Y2b  TCCATGCCTTCCAACTTGCTGTGGACATCGACAGCCATGTCCTGGACCTG 900

Hum Y2   AAGGAGTACAAAACTCATCTTCACAGTGTTCCACATCATCGCCATGTGCTC 950
Rat Y2a  AAGGAGTACAAAACTCATCTTCACCGTGTTCCACATTATTGCGATGTGCTC 950
Rat Y2b  AAGGAGTACAAAACTCATCTTCACCGTGTTCCACATTATTGCGATGTGCTC 950

Hum Y2   CACTTTGCCAATCCCCTTCTCTATGGCTGGATGAACAGCAACTACAGAA  1000
Rat Y2a  CACCTTCGCCAACCCCTTCTCTATGGCTGGATGAACAGCAACTACAGAA  1000
Rat Y2b  CACCTTCGCCAACCCCTTCTCTATGGCTGGATGAACAGCAACTACAGAA  1000

Hum Y2   AGGCTTTCCTCTCGGCCTTCCGCTGTGAGCAGCGGTTGGATGCCATTCAC 1050
Rat Y2a  AAGCTTTCCTCTCAGCCTTCCGCTGTGAGCAGCAGAGGTTGGATGCCATTCAC 1050
Rat Y2b  AAGCTTTCCTCTCAGCCTTCCGCTGTGAGCAGCAGAGGTTGGATGCCATTCAC 1050
```

FIGURE 10D

```
Hum Y2   TCTGAGGTGTCCGTGACATTCAAGGCTAAAAAGAACCTGGAGGTCAGAAA   1100
Rat Y2a  TCGGAGGTGTCCATGACCCTTCAAGGCTAAAAAGAACCTGGAAGTCAAAAA  1100
Rat Y2b  TCGGAGGTGTCCATGACCCTTCAAGGCTAAAAAGAACCTGGAAGTCAAAAA  1100

Hum Y2   GAACAGTGGCCCCCAATGACTCTTTCACAGAGGCTACCAATGTCTAA      1146
Rat Y2a  GAACAATGGCCCTCACTGACTCTTTTCAGAGGCCACCAACGTGTAA       1146
Rat Y2b  GAACAATGGCCCTCACTGACTCTTTTCAGAGGCCACCAACGTGTAA       1146
```

FIGURE 11A

| | | FIGURE 11A |
|---|---|---|
| | | FIGURE 11B |

```
Hum  Y2    MGPIGAEADENQTVEEMKVEQYGP.QTTPRGELVPDDPEPELIDSTKLIEV         49
Rat  Y2a   MGPLGAEADENQTV.EVKVELYGSGPTTPRGELPPDPEPELIDSTKLVEV         49
Rat  Y2b   MGPLGAEADENQTV.EVKVEFYGSGPTTPRGELPPDPEPELIDSTKLVEV         49
                                                         I
                                                     ┌─────────────────
Hum  Y2    QVVLILAYCSIILLGVIGNSLVIHVVI KFKSMRTVTN FFIANLAVADLLV         99
Rat  Y2a   QVVLILAYCSIILLGVVGNSLVIHVVI KFKSMRTVTN FFIANLAVADLLV         99
Rat  Y2b   QVVLILAYCSIILLGVVGNSLVIHVVI KFKSMRTVTN FFIANLAVADLLV         99
                                                         II
                                                     ┌────────────
Hum  Y2    NTLCLPFTLT YTLMGEWKMGPVLCH LVPYAQGLAVQVSTITLTVIAL DRH      149
Rat  Y2a   NTLCLPFTLT YTLMGEWKMGPVLCH LVPYAQGLAVQVSTITLTVIAL DRH      149
Rat  Y2b   NTLCLPFTLT YTLMGEWKMGPVLCH LVPYAQGLAVQVSTITLTVIAL DRH      149
                                  III
                              ┌────────────
Hum  Y2    RCIVYHLESKISKRI SFLIIGLAWGISALLASPLAIF REYSLIEIIPDFE       199
Rat  Y2a   RCIVYHLESKISKQI SFLIIGLAWGVSALLASPLAIF REYSLIEIIPDFE       199
Rat  Y2b   RCIVYHLESKISKQI SFLIIGLAWGVSALLASPLAIF REYSLIEIIPDFE       199
                                        V
                              ┌────────────────
Hum  Y2    IVACTEKWPGEEKSIYGT VYSLSSLLILYLVLPLGIISFSYT RIWSKLKNH      249
Rat  Y2a   IVACTEKWPGEEKSVYGT VYSLSTLLILYLVLPLGIISFSYT RIWSKLKNH      249
Rat  Y2b   IVACTEKWPGEEKSVYGT VYSLSTLLILYLVLPLGIISFSYT RIWSKLKNH      249
                                        VI
                                    ┌────────────
Hum  Y2    VSPGAANDHYHQRRQKTTKM LVCVVVVFAVSWLPLHAFQLAVDI DSQVLD      299
Rat  Y2a   VSPGAASDHYHQRRHKTTKM LVCVVVVFAVSWLPLHAFQLAVDI DSHVLD      299
Rat  Y2b   VSPGAASDHYHQRRHKMTKM LVCVVVVFAVSWLPLHAFQLAVDI DSHVLD      299
```

FIGURE 11B

```
              ┌─────── VII ───────
Hum Y2    LKEYKL  IFTVFHIIAMCSTFANPLLYGWM  NSNYRKAFLSAFRCEQRLDAI  349
Rat Y2a   LKEYKL  IFTVFHIIAMCSTFANPLLYGWM  NSNYRKAFLSAFRCEQRLDAI  349
Rat Y2b   LKEYKL  IFTVFHIIAMCSTFANPLLYGWM  NSNYRKAFLSAFRCEQRLDAI  349

Hum Y2    HSEVSVTFKAKKNLEVRKNSGPNDSFTEATNV  381
Rat Y2a   HSEVSMTFKAKKNLEVKKNNGLTDSFSEATNV  381
Rat Y2b   HSEVSMTFKAKKNLEVKKNNGLTDSFSEATNV  381
```

Cervical Spinal Cord

FIG. 18A 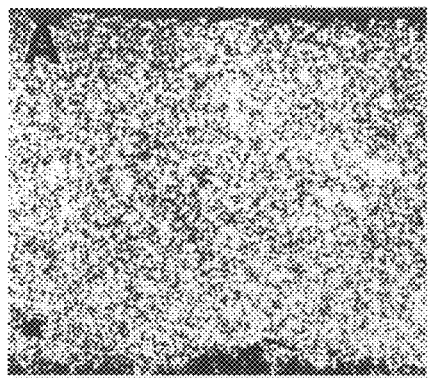 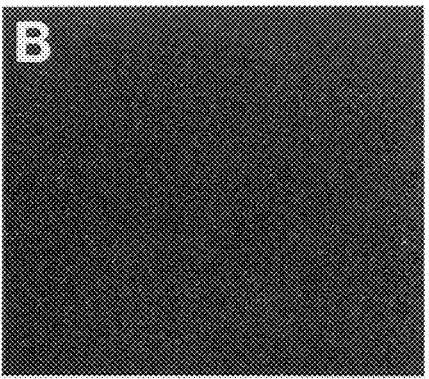 FIG. 18B
FIG. 18C 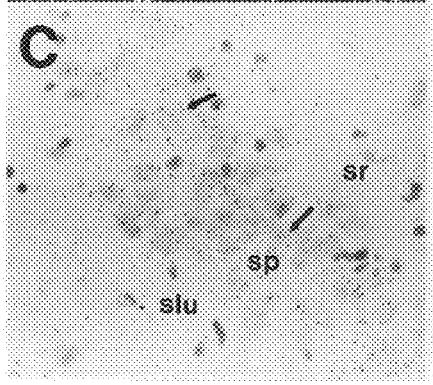 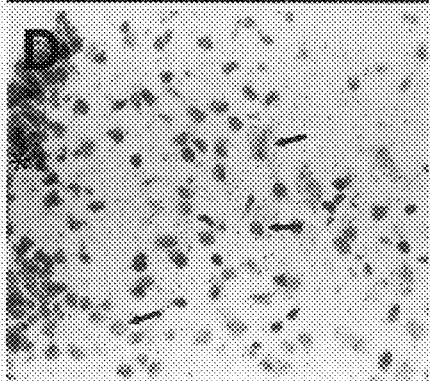 FIG. 18D

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 1280 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 43..1185

(xi) SEQUENCE DESCRIPTION: SEQ ID NO:1:

```
GACTCTTGTG CTGGTTGCAG GCCAAGTGGA CCTGTACTGA AA ATG GGT CCA ATA          54
                                                Met Gly Pro Ile
                                                  1

GGT GCA GAG GCT GAT GAG AAC CAG ACA GTG GAA GAA ATG AAG GTG GAA        102
Gly Ala Glu Ala Asp Glu Asn Gln Thr Val Glu Glu Met Lys Val Glu
  5              10                  15                  20

CAA TAC GGG CCA CAA ACA ACT CCT AGA GGT GAA CTG GTC CCT GAC CCT        150
Gln Tyr Gly Pro Gln Thr Thr Pro Arg Gly Glu Leu Val Pro Asp Pro
                     25                  30                  35

GAG CCA GAG CTT ATA GAT AGT ACC AAG CTG ATT GAG GTA CAA GTT GTT        198
Glu Pro Glu Leu Ile Asp Ser Thr Lys Leu Ile Glu Val Gln Val Val
             40                  45                  50

CTC ATA TTG GCC TAC TGC TCC ATC ATC TTG CTT GGG GTA ATT GGC AAC        246
Leu Ile Leu Ala Tyr Cys Ser Ile Ile Leu Leu Gly Val Ile Gly Asn
         55                  60                  65

TCC TTG GTG ATC CAT GTG GTG ATC AAA TTC AAG AGC ATG CGC ACA GTA        294
Ser Leu Val Ile His Val Val Ile Lys Phe Lys Ser Met Arg Thr Val
     70                  75                  80

ACC AAC TTT TTC ATT GCC AAT CTG GCT GTG GCA GAT CTT TTG GTG AAC        342
Thr Asn Phe Phe Ile Ala Asn Leu Ala Val Ala Asp Leu Leu Val Asn
```

|  |  |  |  |  |  |  |  |  |  |  |
|---|---|---|---|---|---|---|---|---|---|---|
| 85 |  |  |  | 90 |  |  | 95 |  |  | 100 |

```
ACT CTG TGT CTA CCG TTC ACT CTT ACC TAT ACC TTA ATG GGG GAG TGG     390
Thr Leu Cys Leu Pro Phe Thr Leu Thr Tyr Thr Leu Met Gly Glu Trp
            105                 110                 115

AAA ATG GGT CCT GTC CTG TGC CAC CTG GTG CCC TAT GCC CAG GGC CTG     438
Lys Met Gly Pro Val Leu Cys His Leu Val Pro Tyr Ala Gln Gly Leu
            120                 125                 130

GCA GTA CAA GTA TCC ACA ATC ACC TTG ACA GTA ATT GCC CTG GAC CGG     486
Ala Val Gln Val Ser Thr Ile Thr Leu Thr Val Ile Ala Leu Asp Arg
            135                 140                 145

CAC AGG TGC ATC GTC TAC CAC CTA GAG AGC AAG ATC TCC AAG CGA ATC     534
His Arg Cys Ile Val Tyr His Leu Glu Ser Lys Ile Ser Lys Arg Ile
        150                 155                 160

AGC TTC CTG ATT ATT GGC TTG GCC TGG GGC ATC AGT GCC CTG CTG GCA     582
Ser Phe Leu Ile Ile Gly Leu Ala Trp Gly Ile Ser Ala Leu Leu Ala
165                 170                 175                 180

AGT CCC CTG GCC ATC TTC CGG GAG TAT TCG CTG ATT GAG ATC ATC CCG     630
Ser Pro Leu Ala Ile Phe Arg Glu Tyr Ser Leu Ile Glu Ile Ile Pro
                185                 190                 195

GAC TTT GAG ATT GTG GCC TGT ACT GAA AAG TGG CCT GGC GAG GAG AAG     678
Asp Phe Glu Ile Val Ala Cys Thr Glu Lys Trp Pro Gly Glu Glu Lys
            200                 205                 210

AGC ATC TAT GGC ACT GTC TAT AGT CTT TCT TCC TTG TTG ATC TTG TAT     726
Ser Ile Tyr Gly Thr Val Tyr Ser Leu Ser Ser Leu Leu Ile Leu Tyr
            215                 220                 225

GTT TTG CCT CTG GGC ATT ATA TCA TTT TCC TAC ACT CGC ATT TGG AGT     774
Val Leu Pro Leu Gly Ile Ile Ser Phe Ser Tyr Thr Arg Ile Trp Ser
            230                 235                 240

AAA TTG AAG AAC CAT GTC AGT CCT GGA GCT GCA AAT GAC CAC TAC CAT     822
Lys Leu Lys Asn His Val Ser Pro Gly Ala Ala Asn Asp His Tyr His
245                 250                 255                 260

CAG CGA AGG CAA AAA ACC ACC AAA ATG CTG GTG TGT GTG GTG GTG GTG     870
Gln Arg Arg Gln Lys Thr Thr Lys Met Leu Val Cys Val Val Val Val
                265                 270                 275

TTT GCG GTC AGC TGG CTG CCT CTC CAT GCC TTC CAG CTT GCC GTT GAC     918
Phe Ala Val Ser Trp Leu Pro Leu His Ala Phe Gln Leu Ala Val Asp
            280                 285                 290

ATT GAC AGC CAG GTC CTG GAC CTG AAG GAG TAC AAA CTC ATC TTC ACA     966
Ile Asp Ser Gln Val Leu Asp Leu Lys Glu Tyr Lys Leu Ile Phe Thr
            295                 300                 305

GTG TTC CAC ATC ATC GCC ATG TGC TCC ACT TTT GCC AAT CCC CTT CTC    1014
Val Phe His Ile Ile Ala Met Cys Ser Thr Phe Ala Asn Pro Leu Leu
            310                 315                 320

TAT GGC TGG ATG AAC AGC AAC TAC AGA AAG GCT TTC CTC TCG GCC TTC    1062
Tyr Gly Trp Met Asn Ser Asn Tyr Arg Lys Ala Phe Leu Ser Ala Phe
325                 330                 335                 340

CGC TGT GAG CAG CGG TTG GAT GCC ATT CAC TCT GAG GTG TCC GTG ACA    1110
Arg Cys Glu Gln Arg Leu Asp Ala Ile His Ser Glu Val Ser Val Thr
                345                 350                 355

TTC AAG GCT AAA AAG AAC CTG GAG GTC AGA AAG AAC AGT GGC CCC AAT    1158
Phe Lys Ala Lys Lys Asn Leu Glu Val Arg Lys Asn Ser Gly Pro Asn
            360                 365                 370

GAC TCT TTC ACA GAG GCT ACC AAT GTC TAAGGAAGCT GTGGTGTGAA          1205
Asp Ser Phe Thr Glu Ala Thr Asn Val
            375                 380

AATGTATGGA TGAATTCTGA CCAGAGCTAT GAATCTGGTT GATGGCGGCT CACAAGTGAA  1265

AACTGATTTC CCATT                                                    1280
```

(2) INFORMATION FOR SEQ ID NO:2:

(i) SEQUENCE CHARACTERISTICS:
    (A) LENGTH: 381 amino acids
    (B) TYPE: amino acid
    (D) TOPOLOGY: linear (ii) MOLECULE TYPE: protein (xi) SEQUENCE DESCRIPTION: SEQ ID NO:2:

```
Met Gly Pro Ile Gly Ala Glu Ala Asp Glu Asn Gln Thr Val Glu Glu
 1               5                  10                  15

Met Lys Val Glu Gln Tyr Gly Pro Gln Thr Thr Pro Arg Gly Glu Leu
             20                  25                  30

Val Pro Asp Pro Glu Pro Glu Leu Ile Asp Ser Thr Lys Leu Ile Glu
         35                  40                  45

Val Gln Val Val Leu Ile Leu Ala Tyr Cys Ser Ile Ile Leu Leu Gly
     50                  55                  60

Val Ile Gly Asn Ser Leu Val Ile His Val Val Ile Lys Phe Lys Ser
 65                  70                  75                  80

Met Arg Thr Val Thr Asn Phe Phe Ile Ala Asn Leu Ala Val Ala Asp
             85                  90                  95

Leu Leu Val Asn Thr Leu Cys Leu Pro Phe Thr Leu Thr Tyr Thr Leu
        100                 105                 110

Met Gly Glu Trp Lys Met Gly Pro Val Leu Cys His Leu Val Pro Tyr
        115                 120                 125

Ala Gln Gly Leu Ala Val Gln Val Ser Thr Ile Thr Leu Thr Val Ile
130                 135                 140

Ala Leu Asp Arg His Arg Cys Ile Val Tyr His Leu Glu Ser Lys Ile
145                 150                 155                 160

Ser Lys Arg Ile Ser Phe Leu Ile Ile Gly Leu Ala Trp Gly Ile Ser
                165                 170                 175

Ala Leu Leu Ala Ser Pro Leu Ala Ile Phe Arg Glu Tyr Ser Leu Ile
            180                 185                 190

Glu Ile Ile Pro Asp Phe Glu Ile Val Ala Cys Thr Glu Lys Trp Pro
            195                 200                 205

Gly Glu Glu Lys Ser Ile Tyr Gly Thr Val Tyr Ser Leu Ser Ser Leu
210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Asn His Val Ser Pro Gly Ala Ala Asn
                245                 250                 255

Asp His Tyr His Gln Arg Arg Gln Lys Thr Thr Lys Met Leu Val Cys
            260                 265                 270

Val Val Val Val Phe Ala Val Ser Trp Leu Pro Leu His Ala Phe Gln
        275                 280                 285

Leu Ala Val Asp Ile Asp Ser Gln Val Leu Asp Leu Lys Glu Tyr Lys
290                 295                 300

Leu Ile Phe Thr Val Phe His Ile Ile Ala Met Cys Ser Thr Phe Ala
305                 310                 315                 320

Asn Pro Leu Leu Tyr Gly Trp Met Asn Ser Asn Tyr Arg Lys Ala Phe
                325                 330                 335

Leu Ser Ala Phe Arg Cys Glu Gln Arg Leu Asp Ala Ile His Ser Glu
            340                 345                 350

Val Ser Val Thr Phe Lys Ala Lys Lys Asn Leu Glu Val Arg Lys Asn
        355                 360                 365

Ser Gly Pro Asn Asp Ser Phe Thr Glu Ala Thr Asn Val
```

(2) INFORMATION FOR SEQ ID NO:3:

(i) SEQUENCE CHARACTERISTICS:
        (A) LENGTH: 1556 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 211..1353

(xi) SEQUENCE DESCRIPTION: SEQ ID NO:3:

```
GTTGTTAACA GACTCGTGTA AAGGATTTGC TTTATGGAGC TTTTATGAGA TCTGTGGTGT        60

GATGAATCAG AACACAGCTA CGCAGAGGAG CTCAGCCTAA ACTAAATCAA CCCCTTTAGG       120

ATGGTTCTCT GTTTCACTAA CTTTTTTTAA TGTCGTTTTC TGTTATAGAT TCTTGTGCTA       180

TCTGCAGGCC AAATTGGAAC TGAGGTGAAG ATG GGC CCA TTA GGT GCA GAG GCA        234
                                  Met Gly Pro Leu Gly Ala Glu Ala
                                   1               5

GAT GAG AAT CAA ACT GTA GAA GTG AAA GTG GAA CTC TAT GGG TCG GGG         282
Asp Glu Asn Gln Thr Val Glu Val Lys Val Glu Leu Tyr Gly Ser Gly
 10              15                  20

CCC ACC ACT CCT AGA GGT GAG TTG CCC CCT GAT CCA GAG CCG GAG CTC         330
Pro Thr Thr Pro Arg Gly Glu Leu Pro Pro Asp Pro Glu Pro Glu Leu
 25              30                  35                  40

ATA GAC AGC ACC AAA CTG GTT GAG GTG CAG GTG GTC CTT ATA CTG GCC         378
Ile Asp Ser Thr Lys Leu Val Glu Val Gln Val Val Leu Ile Leu Ala
                 45                  50                  55

TAT TGT TCC ATC ATC TTG CTG GGC GTA GTT GGC AAC TCT CTG GTA ATC         426
Tyr Cys Ser Ile Ile Leu Leu Gly Val Val Gly Asn Ser Leu Val Ile
                     60                  65                  70

CAT GTG GTG ATC AAA TTC AAG AGC ATG CGC ACA GTA ACC AAC TTT TTT         474
His Val Val Ile Lys Phe Lys Ser Met Arg Thr Val Thr Asn Phe Phe
                 75                  80                  85

ATT GCC AAC CTG GCT GTG GCG GAT CTT TTG GTG AAC ACC CTG TGC CTG         522
Ile Ala Asn Leu Ala Val Ala Asp Leu Leu Val Asn Thr Leu Cys Leu
                 90                  95                 100

CCA TTC ACT CTT ACC TAT ACC TTG ATG GGG GAG TGG AAA ATG GGT CCA         570
Pro Phe Thr Leu Thr Tyr Thr Leu Met Gly Glu Trp Lys Met Gly Pro
105             110                 115                 120

GTT TTG TGC CAT TTG GTG CCC TAT GCC CAG GGT CTG GCA GTA CAA GTG         618
Val Leu Cys His Leu Val Pro Tyr Ala Gln Gly Leu Ala Val Gln Val
                125                 130                 135

TCC ACA ATA ACT TTG ACA GTC ATT GCT TTG GAC CGA CAT CGT TGC ATT         666
Ser Thr Ile Thr Leu Thr Val Ile Ala Leu Asp Arg His Arg Cys Ile
                140                 145                 150

GTC TAC CAC CTG GAG AGC AAG ATC TCC AAG CAA ATC AGC TTC CTG ATT         714
Val Tyr His Leu Glu Ser Lys Ile Ser Lys Gln Ile Ser Phe Leu Ile
                155                 160                 165

ATT GGC CTG GCG TGG GGT GTC AGC GCT CTG CTG GCA AGT CCC CTT GCC         762
Ile Gly Leu Ala Trp Gly Val Ser Ala Leu Leu Ala Ser Pro Leu Ala
170                 175                 180

ATC TTC CGG GAG TAC TCA CTG ATT GAG ATT ATT CCT GAC TTT GAG ATT         810
Ile Phe Arg Glu Tyr Ser Leu Ile Glu Ile Ile Pro Asp Phe Glu Ile
185                 190                 195                 200
```

-continued

```
GTA GCC TGT ACT GAG AAA TGG CCC GGG GAG GAG AAG AGT GTG TAC GGT      858
Val Ala Cys Thr Glu Lys Trp Pro Gly Glu Glu Lys Ser Val Tyr Gly
            205                 210                 215

ACA GTC TAC AGC CTT TCC ACC CTG CTA ATC CTC TAC GTT TTG CCT CTG      906
Thr Val Tyr Ser Leu Ser Thr Leu Leu Ile Leu Tyr Val Leu Pro Leu
            220                 225                 230

GGC ATC ATA TCT TTC TCC TAC ACC CGG ATC TGG AGT AAG CTA AAG AAC      954
Gly Ile Ile Ser Phe Ser Tyr Thr Arg Ile Trp Ser Lys Leu Lys Asn
            235                 240                 245

CAC GTT AGT CCT GGA GCT GCA AGT GAC CAT TAC CAT CAG CGA AGG CAC     1002
His Val Ser Pro Gly Ala Ala Ser Asp His Tyr His Gln Arg Arg His
            250                 255                 260

AAA ACG ACC AAA ATG CTC GTG TGC GTG GTA GTG GTG TTT GCA GTC AGC     1050
Lys Thr Thr Lys Met Leu Val Cys Val Val Val Val Phe Ala Val Ser
265                 270                 275                 280

TGG CTG CCC CTC CAT GCC TTC CAA CTT GCT GTG GAC ATC GAC AGC CAT     1098
Trp Leu Pro Leu His Ala Phe Gln Leu Ala Val Asp Ile Asp Ser His
            285                 290                 295

GTC CTG GAC CTG AAG GAG TAC AAA CTC ATC TTC ACC GTG TTC CAC ATT     1146
Val Leu Asp Leu Lys Glu Tyr Lys Leu Ile Phe Thr Val Phe His Ile
            300                 305                 310

ATT GCG ATG TGC TCC ACC TTC GCC AAC CCC CTT CTC TAT GGC TGG ATG     1194
Ile Ala Met Cys Ser Thr Phe Ala Asn Pro Leu Leu Tyr Gly Trp Met
            315                 320                 325

AAC AGC AAC TAC AGA AAA GCT TTC CTC TCA GCC TTC CGC TGT GAG CAG     1242
Asn Ser Asn Tyr Arg Lys Ala Phe Leu Ser Ala Phe Arg Cys Glu Gln
            330                 335                 340

AGG TTG GAT GCC ATT CAC TCG GAG GTG TCC ATG ACC TTC AAG GCT AAA     1290
Arg Leu Asp Ala Ile His Ser Glu Val Ser Met Thr Phe Lys Ala Lys
345                 350                 355                 360

AAG AAC CTG GAA GTC AAA AAG AAC AAT GGC CTC ACT GAC TCT TTT TCA     1338
Lys Asn Leu Glu Val Lys Lys Asn Asn Gly Leu Thr Asp Ser Phe Ser
            365                 370                 375

GAG GCC ACC AAC GTG TAAGAATGCT GTGAAAGTAC GTGGGTAAAT TGCGACCAGA     1393
Glu Ala Thr Asn Val
            380

GTTGCCAACC TGGTTAGGGA AGGTTTTCTG GCTAGTGCAT GCCACCTCCC ATTGTATTGA   1453

CCCTAAAAGC ATCAGAGTGG AAGCCCCAGC GGTATTGTTC CTGGAAAACT GGCTGGAAGA   1513

ATGAGGAGAA AATAAACAGA TTGCTGTGGC GCAACGTTCT GAT                    1556
```

(2) INFORMATION FOR SEQ ID NO:4:

(i) SEQUENCE CHARACTERISTICS:
        (A) LENGTH: 381 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Pro Leu Gly Ala Glu Ala Asp Glu Asn Gln Thr Val Glu Val
1               5                   10                  15

Lys Val Glu Leu Tyr Gly Ser Gly Pro Thr Thr Pro Arg Gly Glu Leu
            20                  25                  30

Pro Pro Asp Pro Glu Pro Glu Leu Ile Asp Ser Thr Lys Leu Val Glu
        35                  40                  45

Val Gln Val Val Leu Ile Leu Ala Tyr Cys Ser Ile Ile Leu Leu Gly
    50                  55                  60

Val Val Gly Asn Ser Leu Val Ile His Val Val Ile Lys Phe Lys Ser
```

```
             65                  70                  75                  80
Met Arg Thr Val Thr Asn Phe Phe Ile Ala Asn Leu Ala Val Ala Asp
                         85                  90                  95

Leu Leu Val Asn Thr Leu Cys Leu Pro Phe Thr Leu Tyr Thr Leu
                100                 105                 110

Met Gly Glu Trp Lys Met Gly Pro Val Leu Cys His Leu Val Pro Tyr
            115                 120                 125

Ala Gln Gly Leu Ala Val Gln Val Ser Thr Ile Thr Leu Thr Val Ile
        130                 135                 140

Ala Leu Asp Arg His Arg Cys Ile Val Tyr His Leu Glu Ser Lys Ile
145                 150                 155                 160

Ser Lys Gln Ile Ser Phe Leu Ile Ile Gly Leu Ala Trp Gly Val Ser
                165                 170                 175

Ala Leu Leu Ala Ser Pro Leu Ala Ile Phe Arg Glu Tyr Ser Leu Ile
            180                 185                 190

Glu Ile Ile Pro Asp Phe Glu Ile Val Ala Cys Thr Glu Lys Trp Pro
        195                 200                 205

Gly Glu Glu Lys Ser Val Tyr Gly Thr Val Tyr Ser Leu Ser Thr Leu
            210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Asn His Val Ser Pro Gly Ala Ala Ser
                245                 250                 255

Asp His Tyr His Gln Arg Arg His Lys Thr Thr Lys Met Leu Val Cys
            260                 265                 270

Val Val Val Val Phe Ala Val Ser Trp Leu Pro Leu His Ala Phe Gln
        275                 280                 285

Leu Ala Val Asp Ile Asp Ser His Val Leu Asp Leu Lys Glu Tyr Lys
        290                 295                 300

Leu Ile Phe Thr Val Phe His Ile Ile Ala Met Cys Ser Thr Phe Ala
305                 310                 315                 320

Asn Pro Leu Leu Tyr Gly Trp Met Asn Ser Asn Tyr Arg Lys Ala Phe
                325                 330                 335

Leu Ser Ala Phe Arg Cys Glu Gln Arg Leu Asp Ala Ile His Ser Glu
            340                 345                 350

Val Ser Met Thr Phe Lys Ala Lys Lys Asn Leu Glu Val Lys Lys Asn
        355                 360                 365

Asn Gly Leu Thr Asp Ser Phe Ser Glu Ala Thr Asn Val
        370                 375                 380

(2) INFORMATION FOR SEQ ID NO:5:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (ix) FEATURE:
        (A) NAME/KEY: CDS
        (B) LOCATION: 55..1200

(xi) SEQUENCE DESCRIPTION: SEQ ID NO:5:
```

-continued

| | |
|---|---|
| TTTCTGTTAT AGATTCTTGT GCTATCTGCA GGCCAAATTG GAACTGAGGT GAAG ATG<br>                                                                                                 Met<br>                                                                                                  1 | 57 |
| GGC CCA TTA GGT GCA GAG GCA GAT GAG AAT CAA ACT GTA GAA GTG AAA<br>Gly Pro Leu Gly Ala Glu Ala Asp Glu Asn Gln Thr Val Glu Val Lys<br>                5                      10                        15 | 105 |
| GTG GAA TTC TAT GGG TCG GGG CCC ACC ACT CCT AGA GGT GAG TTG CCC<br>Val Glu Phe Tyr Gly Ser Gly Pro Thr Thr Pro Arg Gly Glu Leu Pro<br>          20                      25                        30 | 153 |
| CCT GAT CCA GAG CCG GAG CTC ATA GAC AGC ACC AAA CTG GTT GAG GTG<br>Pro Asp Pro Glu Pro Glu Leu Ile Asp Ser Thr Lys Leu Val Glu Val<br>35                        40                        45 | 201 |
| CAG GTG GTC CTT ATA CTG GCC TAT TGT TCC ATC ATC TTG CTG GGC GTA<br>Gln Val Val Leu Ile Leu Ala Tyr Cys Ser Ile Ile Leu Leu Gly Val<br>50                        55                        60                        65 | 249 |
| GTT GGC AAC TCT CTG GTA ATC CAT GTG GTG ATC AAA TTC AAG AGC ATG<br>Val Gly Asn Ser Leu Val Ile His Val Val Ile Lys Phe Lys Ser Met<br>                  70                      75                        80 | 297 |
| CGC ACA GTA ACC AAC TTT TTT ATT GCC AAC CTG GCT GTG GCG GAT CTT<br>Arg Thr Val Thr Asn Phe Phe Ile Ala Asn Leu Ala Val Ala Asp Leu<br>                      85                      90                        95 | 345 |
| TTG GTG AAC ACC CTG TGC CTG CCA TTC ACT CTT ACC TAT ACC TTG ATG<br>Leu Val Asn Thr Leu Cys Leu Pro Phe Thr Leu Thr Tyr Thr Leu Met<br>100                      105                      110 | 393 |
| GGG GAG TGG AAA ATG GGT CCA GTT TTG TGC CAT TTG GTG CCC TAT GCC<br>Gly Glu Trp Lys Met Gly Pro Val Leu Cys His Leu Val Pro Tyr Ala<br>115                      120                      125 | 441 |
| CAG GGT CTG GCA GTA CAA GTG TCC ACA ATA ACT TTG ACA GTC ATT GCT<br>Gln Gly Leu Ala Val Gln Val Ser Thr Ile Thr Leu Thr Val Ile Ala<br>130                      135                      140                      145 | 489 |
| TTG GAC CGA CAT CGT TGC ATT GTC TAC CAC CTG GAG AGC AAG ATC TCC<br>Leu Asp Arg His Arg Cys Ile Val Tyr His Leu Glu Ser Lys Ile Ser<br>                      150                      155                      160 | 537 |
| AAG CAA ATC AGC TTC CTG ATT ATT GGC CTG GCG TGG GGT GTC AGC GCT<br>Lys Gln Ile Ser Phe Leu Ile Ile Gly Leu Ala Trp Gly Val Ser Ala<br>                      165                      170                      175 | 585 |
| CTG CTG GCA AGT CCC CTT GCC ATC TTC CGG GAG TAC TCA CTG ATT GAG<br>Leu Leu Ala Ser Pro Leu Ala Ile Phe Arg Glu Tyr Ser Leu Ile Glu<br>180                      185                      190 | 633 |
| ATT ATT CCT GAC TTT GAG ATT GTA GCC TGT ACT GAG AAA TGG CCC GGG<br>Ile Ile Pro Asp Phe Glu Ile Val Ala Cys Thr Glu Lys Trp Pro Gly<br>195                      200                      205 | 681 |
| GAG GAG AAG AGT GTG TAC GGT ACA GTC TAC AGC CTT TCC ACC CTG CTA<br>Glu Glu Lys Ser Val Tyr Gly Thr Val Tyr Ser Leu Ser Thr Leu Leu<br>210                      215                      220                      225 | 729 |
| ATC CTC TAC GTT TTG CCT CTG GGC ATC ATA TCT TTC TCC TAC ACC CGG<br>Ile Leu Tyr Val Leu Pro Leu Gly Ile Ile Ser Phe Ser Tyr Thr Arg<br>                      230                      235                      240 | 777 |
| ATC TGG AGT AAG CTA AAG AAC CAC GTT AGT CCT GGA GCT GCA AGT GAC<br>Ile Trp Ser Lys Leu Lys Asn His Val Ser Pro Gly Ala Ala Ser Asp<br>                      245                      250                      255 | 825 |
| CAT TAC CAT CAG CGA AGG CAC AAA ATG ACC AAA ATG CTC GTG TGC GTG<br>His Tyr His Gln Arg Arg His Lys Met Thr Lys Met Leu Val Cys Val<br>                      260                      265                      270 | 873 |
| GTA GTG GTG TTT GCA GTC AGC TGG CTG CCC CTC CAT GCC TTC CAA CTT<br>Val Val Val Phe Ala Val Ser Trp Leu Pro Leu His Ala Phe Gln Leu<br>275                      280                      285 | 921 |
| GCT GTG GAC ATC GAC AGC CAT GTC CTG GAC CTG AAG GAG TAC AAA CTC<br>Ala Val Asp Ile Asp Ser His Val Leu Asp Leu Lys Glu Tyr Lys Leu<br>290                      295                      300                      305 | 969 |

```
ATC TTC ACC GTG TTC CAC ATT ATT GCG ATG TGC TCC ACC TTC GCC AAC      1017
Ile Phe Thr Val Phe His Ile Ile Ala Met Cys Ser Thr Phe Ala Asn
            310                 315                 320

CCC CTT CTC TAT GGC TGG ATG AAC AGC AAC TAC AGA AAA GCT TTC CTC      1065
Pro Leu Leu Tyr Gly Trp Met Asn Ser Asn Tyr Arg Lys Ala Phe Leu
            325                 330                 335

TCA GCC TTC CGC TGT GAG CAG AGG TTG GAT GCC ATT CAC TCG GAG GTG      1113
Ser Ala Phe Arg Cys Glu Gln Arg Leu Asp Ala Ile His Ser Glu Val
            340                 345                 350

TCC ATG ACC TTC AAG GCT AAA AAG AAC CTG GAA GTC AAA AAG AAC AAT      1161
Ser Met Thr Phe Lys Ala Lys Lys Asn Leu Glu Val Lys Lys Asn Asn
            355                 360                 365

GGC CTC ACT GAC TCT TTT TCA GAG GCC ACC AAC GTG TAA                  1200
Gly Leu Thr Asp Ser Phe Ser Glu Ala Thr Asn Val  *
370                 375                 380
```

(2) INFORMATION FOR SEQ ID NO:6:

(i) SEQUENCE CHARACTERISTICS:
        (A) LENGTH: 381 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Pro Leu Gly Ala Glu Ala Asp Glu Asn Gln Thr Val Glu Val
 1               5                  10                  15

Lys Val Glu Phe Tyr Gly Ser Gly Pro Thr Thr Pro Arg Gly Glu Leu
             20                  25                  30

Pro Pro Asp Pro Glu Pro Glu Leu Ile Asp Ser Thr Lys Leu Val Glu
             35                  40                  45

Val Gln Val Val Leu Ile Leu Ala Tyr Cys Ser Ile Ile Leu Leu Gly
 50                  55                  60

Val Val Gly Asn Ser Leu Val Ile His Val Val Ile Lys Phe Lys Ser
 65                  70                  75                  80

Met Arg Thr Val Thr Asn Phe Phe Ile Ala Asn Leu Ala Val Ala Asp
                 85                  90                  95

Leu Leu Val Asn Thr Leu Cys Leu Pro Phe Thr Leu Thr Tyr Thr Leu
                100                 105                 110

Met Gly Glu Trp Lys Met Gly Pro Val Leu Cys His Leu Val Pro Tyr
            115                 120                 125

Ala Gln Gly Leu Ala Val Gln Val Ser Thr Ile Thr Leu Thr Val Ile
            130                 135                 140

Ala Leu Asp Arg His Arg Cys Ile Val Tyr His Leu Glu Ser Lys Ile
145                 150                 155                 160

Ser Lys Gln Ile Ser Phe Leu Ile Ile Gly Leu Ala Trp Gly Val Ser
                165                 170                 175

Ala Leu Leu Ala Ser Pro Leu Ala Ile Phe Arg Glu Tyr Ser Leu Ile
                180                 185                 190

Glu Ile Ile Pro Asp Phe Glu Ile Val Ala Cys Thr Glu Lys Trp Pro
            195                 200                 205

Gly Glu Glu Lys Ser Val Tyr Gly Thr Val Tyr Ser Leu Ser Thr Leu
            210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Asn His Val Ser Pro Gly Ala Ala Ser
                245                 250                 255
```

```
Asp His Tyr His Gln Arg Arg His Lys Met Thr Lys Met Leu Val Cys
            260                 265                 270

Val Val Val Val Phe Ala Val Ser Trp Leu Pro Leu His Ala Phe Gln
        275                 280                 285

Leu Ala Val Asp Ile Asp Ser His Val Leu Asp Leu Lys Glu Tyr Lys
290                 295                 300

Leu Ile Phe Thr Val Phe His Ile Ile Ala Met Cys Ser Thr Phe Ala
305                 310                 315                 320

Asn Pro Leu Leu Tyr Gly Trp Met Asn Ser Asn Tyr Arg Lys Ala Phe
            325                 330                 335

Leu Ser Ala Phe Arg Cys Glu Gln Arg Leu Asp Ala Ile His Ser Glu
            340                 345                 350

Val Ser Met Thr Phe Lys Ala Lys Lys Asn Leu Glu Val Lys Lys Asn
            355                 360                 365

Asn Gly Leu Thr Asp Ser Phe Ser Glu Ala Thr Asn Val
            370                 375                 380
```

(2) INFORMATION FOR SEQ ID NO:7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
CAAGTTGTTC TCATATTGGC CTACTGCTCC ATCATCTTGC TTGGGGTAAT          50
```

(2) INFORMATION FOR SEQ ID NO:8:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
ATCACCACAT GGATCACCAA GGAGTTGCCA ATTACCCCAA GCAAGATGAT          50
```

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
TTTTTCATTG CCAATCTGGC TGTGGCAGAT CTTTTGGTGA ACACT               45
```

(2) INFORMATION FOR SEQ ID NO:10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

AGGTAAGAGT GAACGGTAGA CACAGAGTGT TCACCAAAAG ATCTG          45

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

CCACCTGGTG CCCTATGCCC AGGGCCTGGC AGTACAAGTA TCCAC          45

(2) INFORMATION FOR SEQ ID NO:12:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

CAGGGCAATT ACTGTCAAGG TGATTGTGGA TACTTGTACT GCCAG          45

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

AATCAGCTTC CTGATTATTG GCTTGGCCTG GGGCATCAGT GCCCT          45

(2) INFORMATION FOR SEQ ID NO:14:

```
        (i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

GAAGATGGCC AGGGGACTTG CCAGCAGGGC ACTGATGCCC CAGGC                     45

(2) INFORMATION FOR SEQ ID NO:15:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

ACTGTCTATA GTCTTTCTTC CTTGTTGATC TTGTATGTTT TGCCT                     45

(2) INFORMATION FOR SEQ ID NO:16:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

TGTAGGAAAA TGATATAATG CCCAGAGGCA AAACATACAA GATCA                     45

(2) INFORMATION FOR SEQ ID NO:17:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

CTGGTGTGTG TGGTGGTGGT GTTTGCGGTC AGCTGGCTGC CTCTC                     45

(2) INFORMATION FOR SEQ ID NO:18:

(i) SEQUENCE CHARACTERISTICS:
            (A) LENGTH: 45 base pairs
            (B) TYPE: nucleic acid
            (C) STRANDEDNESS: single
```

(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

TGTCAACGGC AAGCTGGAAG GCATGGAGAG GCAGCCAGCT GACCG                    45

(2) INFORMATION FOR SEQ ID NO:19:

(i) SEQUENCE CHARACTERISTICS:
          (A) LENGTH: 47 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

CTCATCTTCA CAGTGTTCCA CATCATCGCC ATGTGCTCCA CTTTTGC                  47

(2) INFORMATION FOR SEQ ID NO:20:

(i) SEQUENCE CHARACTERISTICS:
          (A) LENGTH: 47 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

TTCATCCAGC CATAGAGAAG GGGATTGGCA AAAGTGGAGC ACATGGC                  47

(2) INFORMATION FOR SEQ ID NO:21:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

GGGAGTATTC GCTGATTGAG ATCAT                                          25

(2) INFORMATION FOR SEQ ID NO:22:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

GCCTTGAATG TCACGGACAC CTC                                                      23

(2) INFORMATION FOR SEQ ID NO:23:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

CTGATGGTAG TGGTCATTTG CAGCTCCAGG ACTGACATGG TTCTT                               45

(2) INFORMATION FOR SEQ ID NO:24:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO:24:

GGCCCATTAG GTGCAGAGGC AGATGAGAAT CAAACTGTAG AAGTG                               45

(2) INFORMATION FOR SEQ ID NO:25:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: YES (xi) SEQUENCE DESCRIPTION: SEQ ID NO:25:

CACTTCTACA GTTTGATTCT CATCTGCCTC TGCACCTAAT GGGCC                               45

(2) INFORMATION FOR SEQ ID NO:26:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO:26:

CGGAGGTGTC CATGACCTTC AAGGCTAAAA AGAACCTGGA AGTCA                               45

(2) INFORMATION FOR SEQ ID NO:27:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: DNA (genomic)

(iv) ANTI-SENSE: YES (xi) SEQUENCE DESCRIPTION: SEQ ID NO:27:

TGACTTCCAG GTTCTTTTTA GCCTTGAAGG TCATGGACAC CTCCG                    45

USES OF NUCLEIC ACID ENCODING NEUROPEPTIDE Y/PEPTIDE YY (Y2) RECEPTORS NUCLEIC ACID ENCODING

This application is a 371 of PCT/US95/01469 and a continuation-in-part of U.S. Ser. No. 08/192,288, filed Feb. 3, 1994, now U.S. Pat. No. 5,545,549, the contents of which are hereby incorporated by reference into the subject application.

BACKGROUND OF THE INVENTION

Throughout this application, various publications are referenced in parenthesis by number. Full citations for these references may be found at the end of the specification immediately preceding the claims. The disclosure of these publications is hereby incorporated by reference into this application to describe more fully the art to which this invention pertains.

Neuropeptides are small peptides originating from large precursor proteins synthesized by peptidergic neurons and endocrine/paracrine cells. They hold promise for treatment of neurological, psychiatric, and endocrine disorders (46). Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals.

Neuropeptide Y (NPY), a 36-amino acid peptide, is the most abundant neuropeptide to be identified in mammalian brain. NPY is an important regulator in both the central and peripheral nervous systems (47) and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and have contributed to vasoconstriction. NPY binding sites have been identified in a variety of tissues, including spleen (48), intestinal membranes, brain (49), aortic smooth muscle (50), kidney, testis, and placenta (2). In addition, binding sites have been reported in a number of rat and human cell lines (e.g. Y1 in SK-N-MC, MC-IXC, CHP-212, and PC12 cells; Y2 in SK-N-Be(2), CHP-234, and SMS-MSN) (51,5).

Neuropeptide Y (NPY) receptor pharmacology is currently defined by structure activity relationships within the pancreatic polypeptide family (1, 2). This family includes NPY, which is synthesized primarily in neurons; peptide YY (PYY), which is synthesized primarily by endocrine cells in the gut; and pancreatic polypeptide (PP), which is synthesized primarily by endocrine cells in the pancreas. These 36 amino acid peptides have a compact helical structure involving a "PP-fold" in the middle of the peptide. Specific features include a polyproline helix in residues 1 through 8, a β-turn in residues 9 through 14, an α-helix in residues 15 through 30, an outward-projecting C-terminus in residues 30 through 36, and a carboxyl terminal amide which appears to be critical for biological activity (3). The peptides have been used to define at least four receptor subtypes known as Y1, Y2, Y3, and PP. Y1 receptor recognition by NPY involves both N- and C-terminal regions of the peptide; exchange of $Gln^{34}$ with $Pro^{34}$ is fairly well tolerated (3, 4, 5). Y2 receptor recognition by NPY depends primarily upon the four C-terminal residues of the peptide ($Arg^{33}$-$Gln^{34}$-$Arg^{35}$-$Tyr36$-$NH_2$) preceded by an amphipathic α-helix (3, 6, 7); exchange of $Gln^{34}$ with $Pro^{34}$ is not well tolerated (4, 5). Y3 receptor recognition is characterized by a strong preference for NPY over PYY (8). Exchange of $Gln^{34}$ in NPY with $Pro^{34}$ is reasonably well tolerated by the Y3 receptor but PP, which also contains $Pro^{34}$, does not bind well (8). The PP receptor is reported to bind tightly to PP, less so to [$Leu^{31}$, $Pro^{34}$]NPY, and even less so to NPY (3, 9). The only NPY receptor which has been cloned to date is the Y1 receptor gene, from mouse (12), rat (52), and human (10). One of the key pharmacological features which distinguish Y1 and Y2 is the fact that the Y1 receptor (and not the Y2 receptor) responds to an analog of NPY modified at residues 31 and 34 ([Leu31,Pro34]NPY), whereas the Y2 receptor (and not the Y1 receptor) has high affinity for the NPY peptide carboxyl-terminal fragment NPY-(13-36) (53,4).

Receptor genes for the other two structurally related peptides, peptide YY (PYY) and pancreatic polypeptide (PP), also have not been cloned. Peptide YY occurs mainly in endocrine cells in the lower gastrointestinal tract (54). Receptors for PYY were first described in the rat small intestine (55). This receptor has been defined as PYY-preferring because it displays a 5–10 fold higher affinity for PYY than for NPY (55, 56). Recently, a cell line, PKSV-PCT, derived from the proximal tubules of kidneys, has been described to express receptors for PYY (57).

In the last few years only the rat and human Y1 cDNAs have been cloned (10, 11). This success was based on identifying the randomly cloned FC5 "orphan receptor" (12). We now report the isolation by expression cloning of a human hippocampal Y2 cDNA clone and two rat Y2 clones and their pharmacological characterization.

SUMMARY OF THE INVENTION

This invention provides an isolated nucleic acid molecule encoding a Y2 receptor.

This invention also provides an isolated protein which is a Y2 receptor.

This invention provides a vector comprising nucleic acid encoding a Y2 receptor.

This invention also provides vectors such as plasmids comprising nucleic acid encoding a Y2 receptor, adapted for expression in a bacterial cell, a yeast cell, an insect cell or a mammalian cell which additionally comprise the regulatory elements necessary for expression of the nucleic acid in the bacterial, yeast, insect or mammalian cells operatively linked to the nucleic acid encoding the Y2 receptor as to permit expression thereof.

This invention provides a cell transfected with and expressing nucleic acid encoding a Y2 receptor.

This invention provides a nucleic acid probe comprising a nucleic acid molecule of at least 15 nucleotides capable of specifically hybridizing with a unique sequence included within the sequence of a nucleic acid molecule encoding a Y2 receptor.

This invention provides an antisense oligonucleotide having a sequence capable of specifically hybridizing with any sequences of an mRNA molecule which encodes a Y2 receptor so as to prevent translation of the mRNA molecule.

This invention provides an antibody directed to a Y2 receptor.

This invention provides a transgenic nonhuman mammal expressing nucleic acid encoding a Y2 receptor. This invention further provides a transgenic nonhuman mammal whose genome comprises antisense DNA complementary to DNA encoding a Y2 receptor so placed as to be transcribed into antisense mRNA which is complementary to mRNA encoding a Y2 receptor and which hybridizes to mRNA encoding a Y2 receptor thereby reducing its translation.

This invention further provides a transgenic nonhuman mammal comprising a homologous recombination knockout of the native Y2 receptor.

This invention provides a method for determining whether a ligand can bind specifically to a Y2 receptor which comprises contacting a cell transfected with and expressing nucleic acid encoding the Y2 receptor with the ligand under conditions permitting binding of ligands to such receptor, and detecting the presence of any such ligand bound to the Y2 receptor, thereby determining whether the ligand binds specifically to a Y2 receptor.

This invention also provides a method for determining whether a ligand is a Y2 receptor agonist which comprises contacting a cell transfected with and expressing nucleic acid encoding the Y2 receptor with the ligand under conditions permitting the activation of a functional Y2 receptor response from the cell, and detecting, by means of a bioassay, such as a second messenger assay, an increase in Y2 receptor activity, thereby determining whether the ligand is a Y2 receptor agonist.

This invention further provides a method for determining whether a ligand is a Y2 receptor antagonist which comprises contacting a cell transfected with and expressing nucleic acid encoding the Y2 receptor with the ligand in the presence of a known Y2 receptor agonist, such as NPY, under conditions permitting the activation of a functional Y2 receptor response, and detecting, by means of a bioassay, such as a second messenger assay, a decrease in Y2 receptor activity, thereby determining whether the ligand is a Y2 receptor antagonist.

This invention further provides a method of screening drugs to identify drugs which specifically bind to a Y2 receptor on the surface of a cell which comprises contacting a cell transfected with and expressing nucleic acid encoding the Y2 receptor with a plurality of drugs under conditions permitting binding of drugs to the Y2 receptor, and determining those drugs which bind to the Y2 receptor, thereby identifying drugs which specifically bind to a Y2 receptor.

This invention also provides a method of screening drugs to identify drugs which act as agonists of a Y2 receptor on the surface of a cell which comprises contacting a cell transfected with and expressing nucleic acid encoding the Y2 receptor with a plurality of drugs under conditions permitting the activation of a functional Y2 receptor response, and determining those drugs which activate the Y2 receptor, using a bioassay, such as a second messenger assay, thereby identifying drugs which act as Y2 receptor agonists.

This invention also provides a method of screening drugs to identify drugs which act as antagonists of a Y2 receptor on the surface of a cell which comprises contacting a cell transfected with and expressing nucleic acid encoding the Y2 receptor with a plurality of drugs in the presence of a known Y2 receptor agonist, such as NPY, under conditions permitting the activation of a functional Y2 receptor response, and determining those drugs which inhibit the activation of the Y2 receptor, using a bioassay, such as a second messenger assay, thereby identifying drugs which act as Y2 receptor antagonists.

This invention also provides a method of detecting expression of a Y2 receptor by a cell by detecting the presence of mRNA coding for the Y2 receptor which comprises obtaining total mRNA from the cell and contacting the mRNA so obtained with a nucleic acid probe comprising a nucleic acid molecule of at least 15 nucleotides capable of specifically hybridizing with a unique sequence included within the sequence of a nucleic acid molecule encoding the Y2 receptor under hybridizing conditions, and detecting the presence of mRNA hybridized to the probe, thereby detecting the expression of a Y2 receptor by the cell.

This invention provides a method of determining the physiological effects of expressing varying levels of Y2 receptors which comprises producing a transgenic nonhuman mammal expressing nucleic acid encoding a Y2 receptor whose levels of Y2 receptor expression are varied by use of an inducible promoter which regulates Y2 receptor expression.

This invention also provides a method of determining the physiological effects of expressing varying levels of Y2 receptors which comprises producing a panel of transgenic nonhuman animals each expressing nucleic acid encoding a Y2 receptor expressing nucleic acid and expressing a different amount of Y2 receptor.

This invention provides a method for diagnosing a predisposition to a disorder associated with the activity of a specific Y2 receptor allele which comprises: a. obtaining nucleic acid of subjects suffering from the disorder; b. performing a restriction digest of the nucleic acid with a panel of restriction enzymes; c. electrophoretically separating the resulting nucleic acid fragments on a sizing gel; d. contacting the resulting gel with a nucleic acid probe capable of specifically hybridizing to nucleic acid encoding a Y2 receptor and labeled with a detectable marker; e. detecting labeled bands which have hybridized to the nucleic acid encoding a Y2 receptor labelled with a detectable marker to create a unique band pattern specific to the nucleic acid of subjects suffering from the disorder; f. preparing nucleic acid obtained for diagnosis by steps a–e; and g. comparing the unique band pattern specific to the nucleic acid of subjects suffering from the disorder from step e and the nucleic acid obtained for diagnosis from step f to determine whether the patterns are the same or different and to diagnose thereby predisposition to the disorder if the patterns are the same.

This invention provides a method of preparing an isolated, purified Y2 receptor which comprises constructing a vector adapted for expression in a cell which comprises the regulatory elements necessary for the expression of nucleic acid in the cell operatively linked to the nucleic acid encoding a Y2 receptor as to permit expression thereof, wherein the cell is selected from the group consisting of bacterial cells, yeast cells, insect cells and mammalian cells; inserting the vector of the previous step in a suitable host cell; incubating the cells under conditions allowing the expression of a Y2 receptor; recovering the receptor so produced and purifying the receptor so recovered.

BRIEF DESCRIPTION OF THE DRAWINGS

FIG. 1 Nucleotide sequence of the human hippocampal Y2 cDNA clone (SEQ. I.D. No. 1). Initiation and stop codon are indicated in bold. Only partial 5' and 3' untranslated sequences are shown.

FIG. 2 Deduced amino acid sequence of the human hippocampal Y2 cDNA clone encoded by the nucleotide sequence in FIG. 1 (SEQ. I.D. No. 2).

FIG. 3A through FIG. 3D

Comparison of coding nucleotide sequences between human hippocampal Y2 (top row) and Y1 human cDNA clones (bottom row) (48.5% nucleotide identity).

FIG. 4A and FIG. 4B Comparison of amino acid sequences between hippocampal Y2 (top row) and Y1 human cDNA clones (bottom row). (31% overall identity and 41% in the transmembrane domains).

Figure 5A:
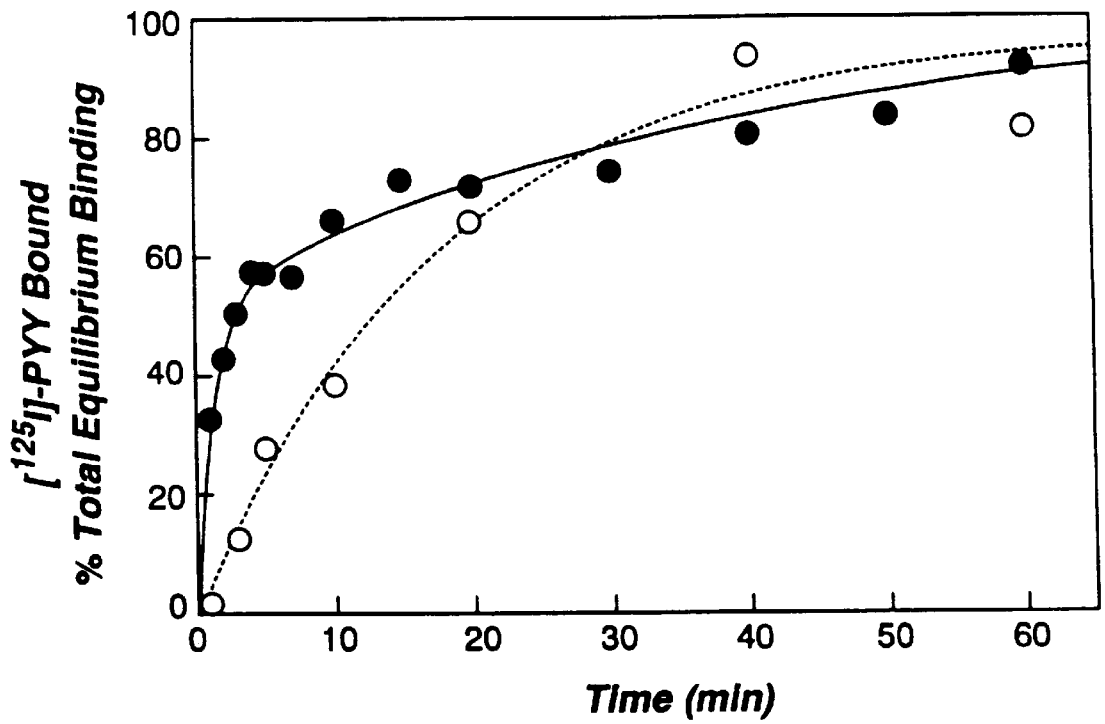

FIG. 5A Equilibrium binding of $^{125}$I-PYY to membranes from COS-7 cells transiently expressing CG-13 (●) and human Y1 (○) receptors. Membranes were incubated with $^{125}$I-PYY for the times indicated, in the presence or absence of 100 nM human NPY. Specific binding, B, was plotted against time, t, to obtain the maximum number of equilibrium binding sites, $B_1$ and $B_2$, and observed association rates, $K_{obs1}$ and $K_{obs2}$, according to the equation, $B=B_1*(1-e^{-(kobs1*t)})=B_2*(1-e^{-(kobs2*t)})$. Binding is shown as the percentage of total equilibrium binding, $B_1+B_2$, determined by nonlinear regression analysis. Data are representative of three independent experiments, with each point measured in triplicate.

Figure 5B:
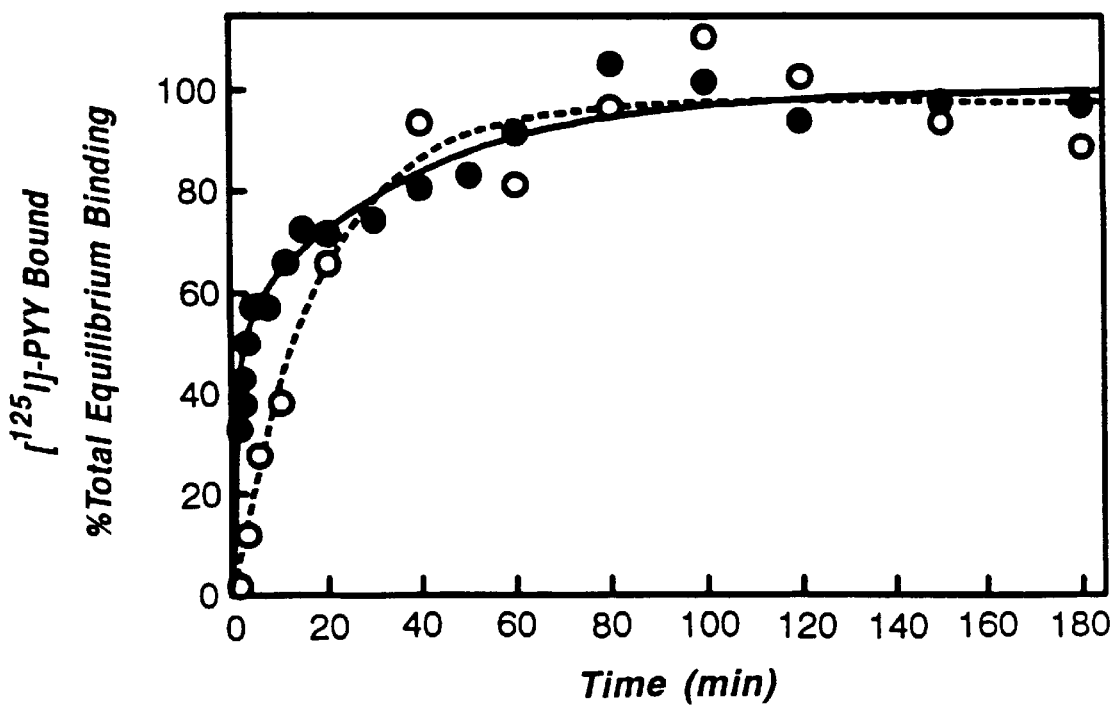

FIG. 5B Equilibrium binding of $^{125}$I-PYY to membranes from COS-7 cells transiently expressing CG-13 (●) and human Y1 (○) receptors using the same conditions as in FIG. 5A except for a prolonged time course of up to 180 minutes.

Figure 6:
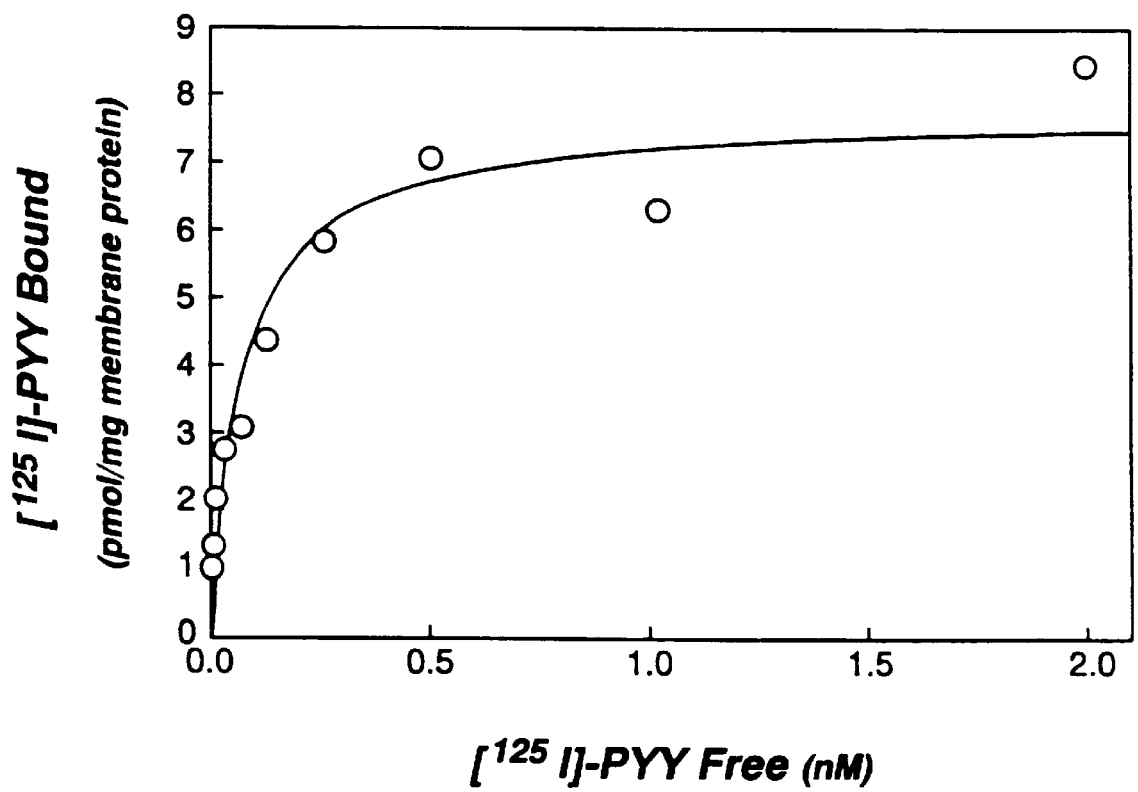

FIG. 6 Saturable equilibrium binding of $^{125}$I-PYY to membranes from COS-7 cells transiently expressing CG-13 receptors. Membranes were incubated with $^{125}$I-PYY ranging in concentration from 0.003 nM to 2 nM, in the presence or absence of 100 nM human NPY. Specific binding, B, was plotted against the free $^{125}$I-PYY concentration, [L], to obtain the maximum number of saturable binding sites, $B_{max}$, and the $^{125}$I-PYY equilibrium dissociation constant, $K_d$, according to the binding isotherm, $B=B_{max}[L]/([L]+K_d)$. Specific binding is shown. Data are representative of three independent experiments, with each point measured in triplicate.

Figure 7A:
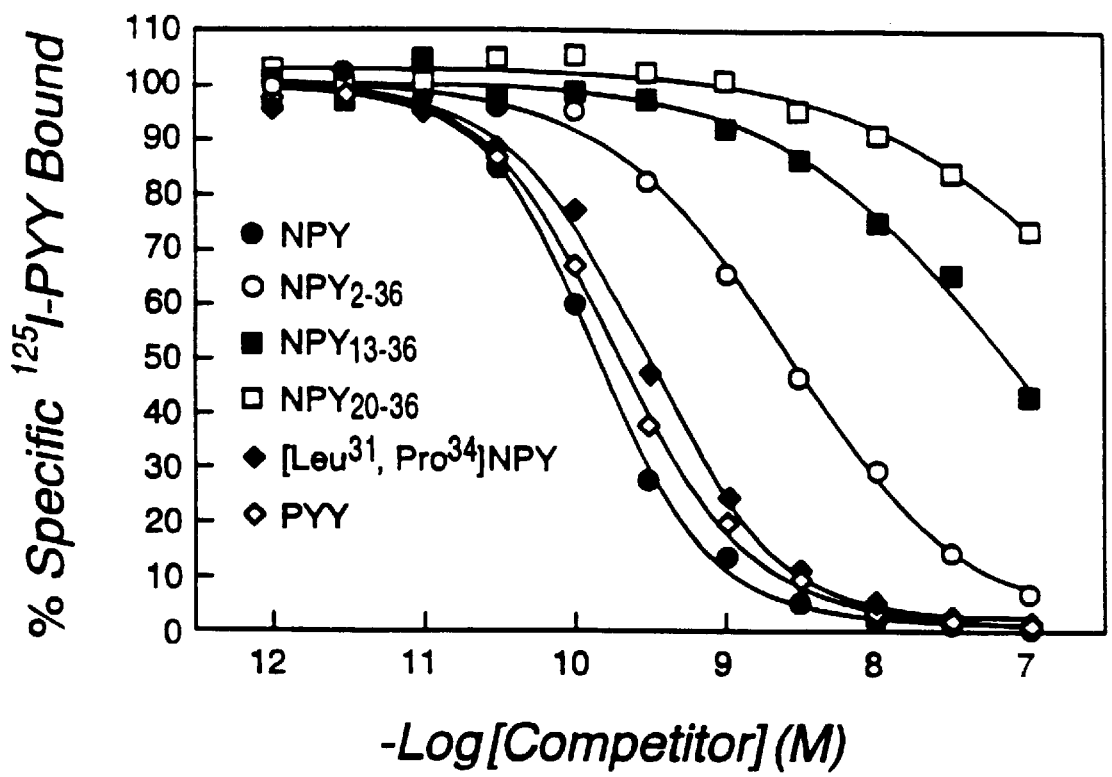

FIG. 7A Competitive displacement of $^{125}$I-PYY on membranes from COS-7 cells transiently expressing Human Y1 receptors. Membranes were incubated with $^{125}$I-PYY and increasing concentrations of peptide competitors. $IC_{50}$ values corresponding to 50% displacement were determined by nonlinear regression analysis and converted to $K_i$ values according to the equation, $K_i=IC_{50}/(1+[L]/K_d)$, where [L] is the $^{125}$I-PYY concentration and $K_d$ is the equilibrium dissociation constant of $_{125}$I-PYY. Data are representative of at least two independent experiments, with each point measured once or in duplicate. Rank orders of affinity for these and other compounds are listed separately in Table 2.

Figure 7B:
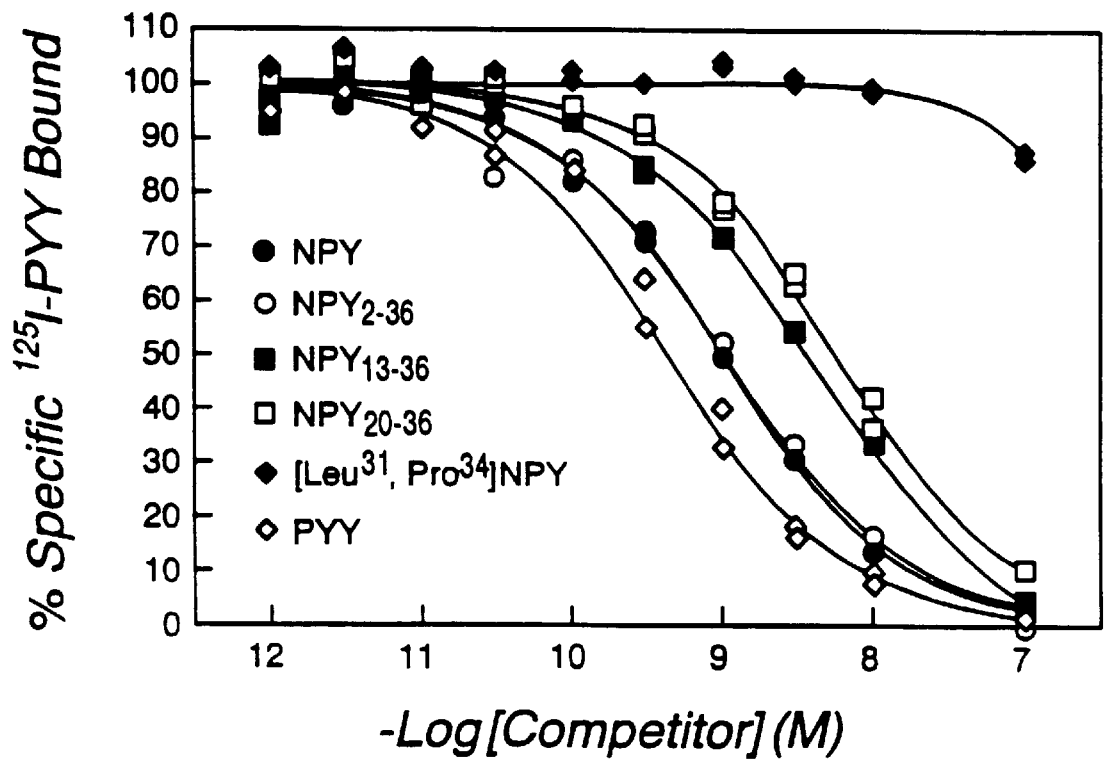

FIG. 7B Competitive displacement of $^{125}$I-PYY on membranes from COS-7 cells transiently expressing human Y2 receptors. Membranes were incubated with $^{125}$I-PYY and increasing concentrations of peptide competitors. $IC_{50}$ values corresponding to 50% displacement were determined by nonlinear regression analysis and converted to $K_i$ values according to the equation, $K_i=IC_{50}/(1+[L]/K_d)$, where [L] is the $^{125}$I-PYY concentration and $K_d$ is the equilibrium dissociation constant of 125-PYY. Data are representative of at least two independent experiments, with each point measured once or in duplicate. Rank orders of affinity for these and other compounds are listed separately in Table 2.

FIGS. 8A–8E Nucleotide sequence (SEQ. I.D. No. 3) and deduced amino acid sequence (SEQ. I.D. No. 4) of the rat Y2 receptor encoded by rs5a. Nucleotides are presented in the 5' to 3' orientation and the coding region is numbered starting from the putative initiating methionine and ending in the termination codon. Deduced amino acid sequence by translation of a long open reading frame is shown using one-letter symbols.

FIGS. 9A–9D Nucleotide sequence (SEQ. I.D. No. 5) and deduced amino acid sequence (SEQ. I.D. No. 6) of the rat Y2 receptor encoded by rs26a. Nucleotides are presented in the 5' to 3' orientation and the coding region is numbered starting from the putative initiating methionine and ending in the termination codon. Deduced amino acid sequence by translation of a long open reading frame is shown using one-letter symbols.

FIGS. 10A–10D Alignment of rat and human Y2 receptors: nucleotide sequences. Nucleotide sequences of the coding regions of the human Y2 receptor (HumY2) and the rat Y2 receptors encoded by rs5a (RatY2a) and rs26a (RatY2b) are shown; the nucleotide sequence of rs26a (RatY2b) is identical to rs5a (RatY2a) except where shown. Rat and human Y2 nucleotide sequences exhibit ~86% identity in the coding region.

FIGS. 11A–11B Alignment of rat and human Y2 receptors: amino acid sequences. Complete predicted amino acid sequences of the human Y2 receptor (Hum Y2) and the rat Y2 receptor encoded by rs5a (Rat Y2a) are shown; the amino acid sequence of RatY2b encoded by rs26a is identical to RatY2a except where shown. Rat and human Y2 amino acid sequences are ~94% identical overall and ~98% identical in the transmembrane domains (bracketed). Single letter abbreviations for amino acids are shown.

FIGS. 12A–12H Localization of Rat Y2 mRNA in the rat central nervous system. Schematic diagrams of half-coronal sections through the rat brain showing the distribution of neuropeptide Y Y2 receptor mRNA obtained with radiolabelled oligonucleotide probes and in situ hybridization histochemistry. The stars show the location of labeled neuronal populations, and are not indicative of the number of cells observed in each area.

Figure 13A:
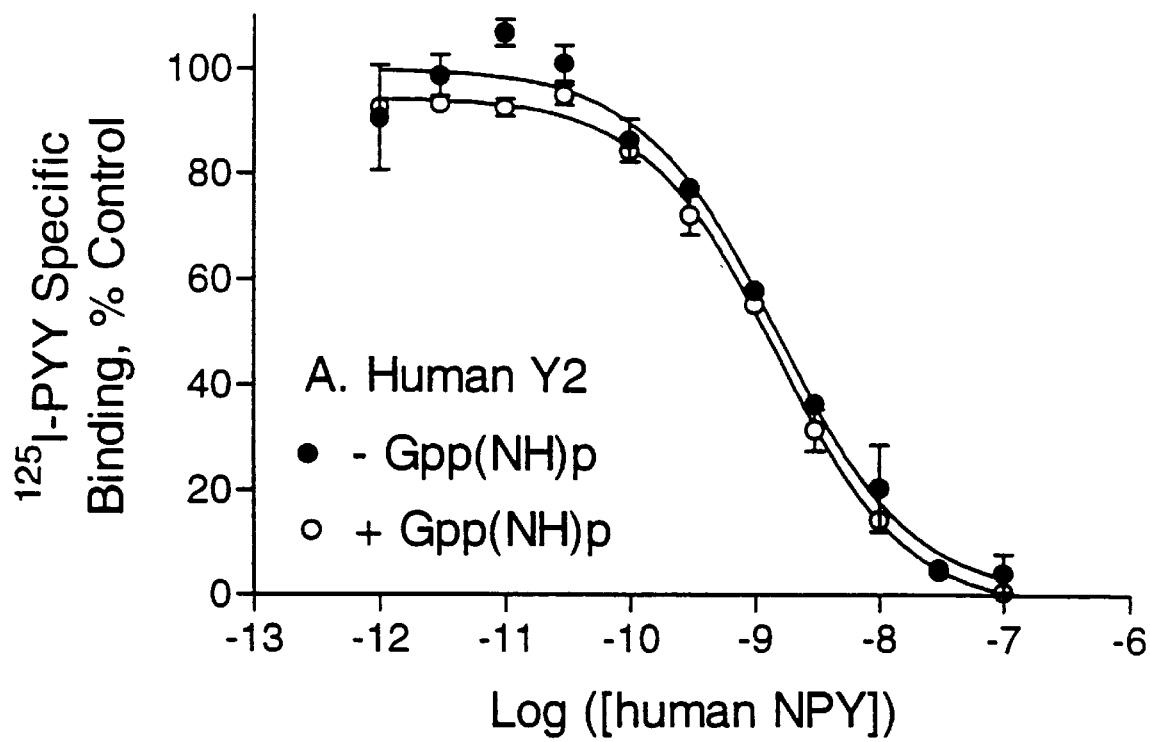
Figure 13B:
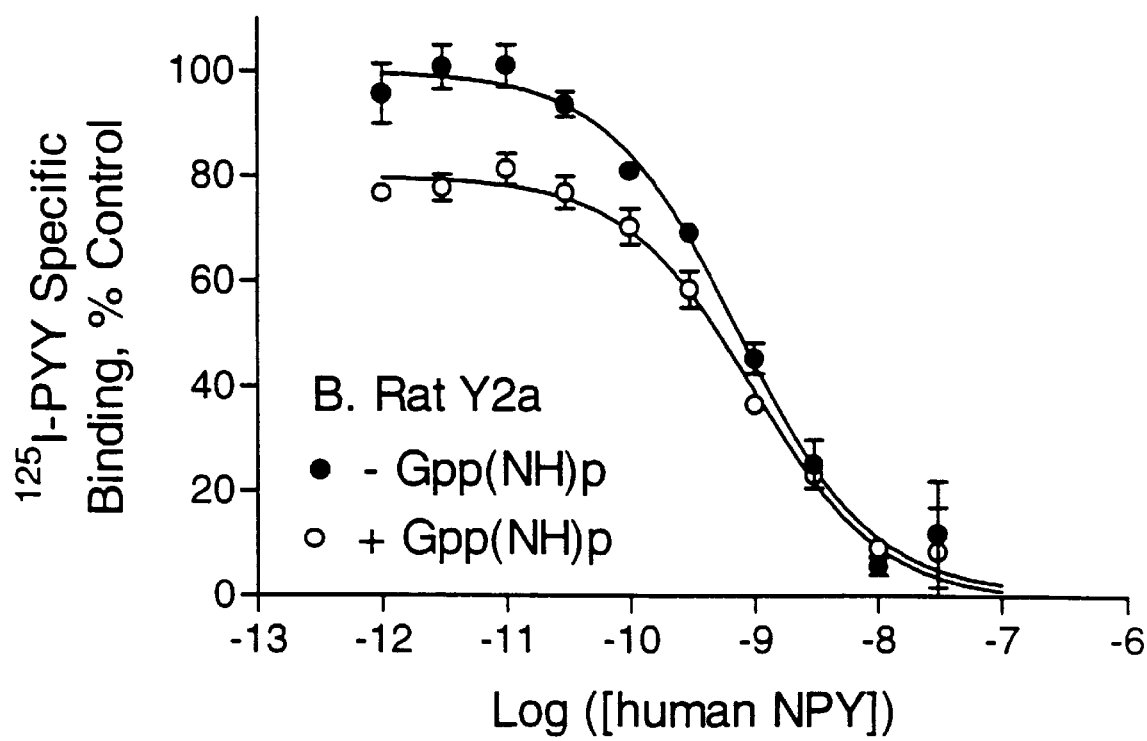

FIGS. 13A–13B Effects of Gpp(NH)p on radio ligand binding to Y2 receptors. Binding data were generated from competitive displacement assays in the absence (●) or presence (○) of 100 μM Gpp(NH)p. The maximum specific binding detected under control conditions (in the absence of Gpp(NH)p) was used to normalize the data. A) Human Y2 receptor transiently expressed in COS-7 cells. B) Rat Y2a receptor transiently expressed in COS-7 cells.

Figure 14:
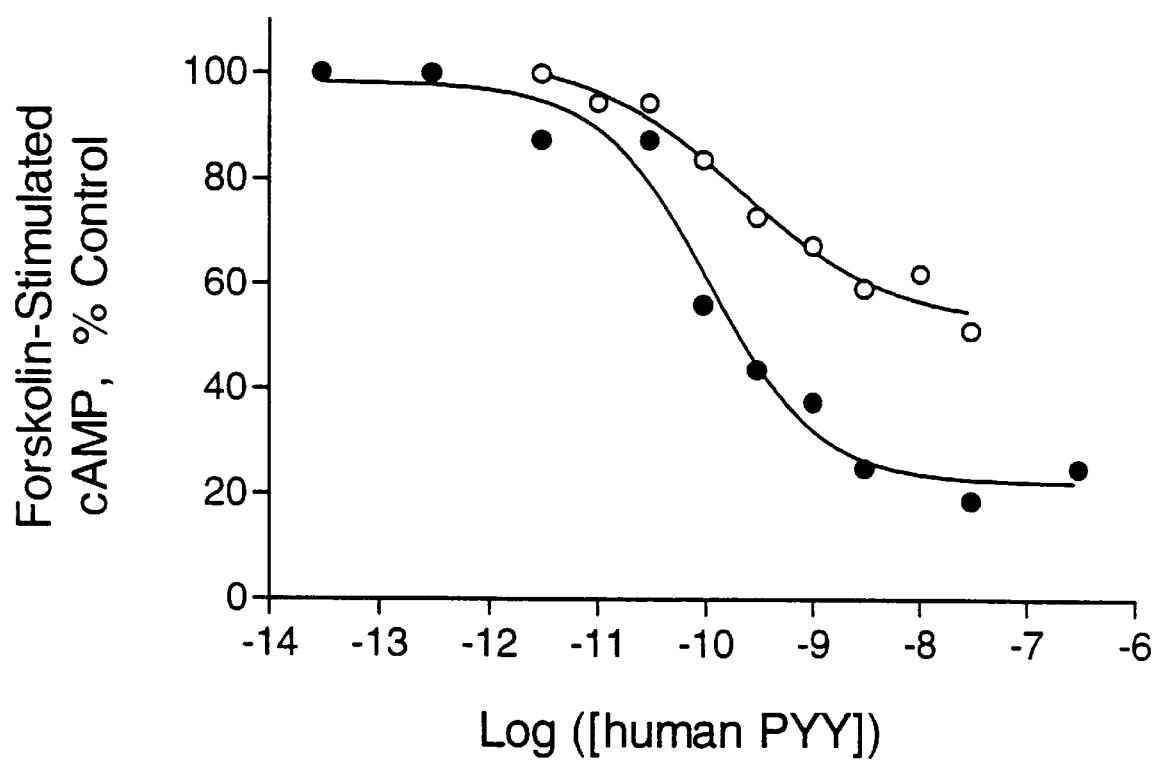

FIG. 14 Inhibition of forskolin-stimulated cAMP accumulation in intact cells stably expressing the human Y2 receptor. Functional data were derived from radioimmunoassay of cAMP in 293 cells stimulated with 10 μM forskolin over a 5 min period. Human PYY was tested for agonist activity over the same period. Data were fit to a four parameter logistic equation by nonlinear regression. Data generated from stably transfected 293 cells (●) and from stably transfected NIH-3T3 cells (○). Data shown are representative of ten (●) and two (○) independent experiments.

Figure 15A:
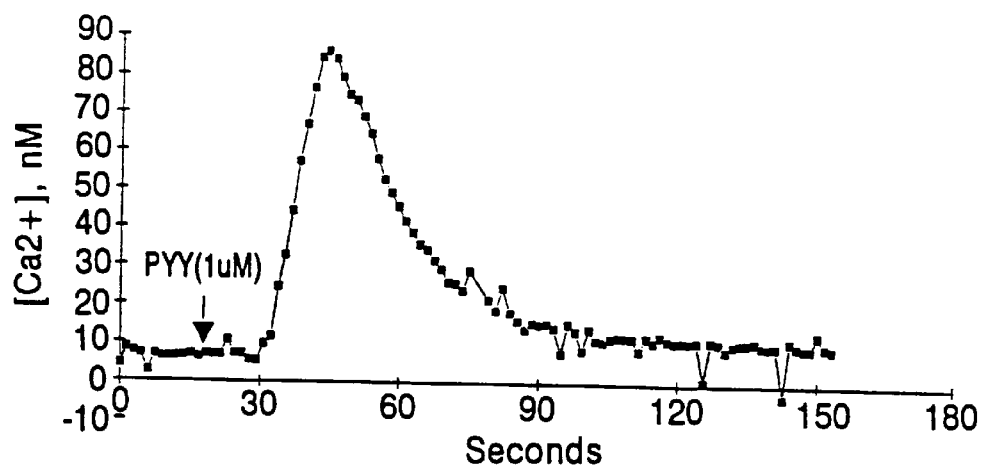
Figure 15B:
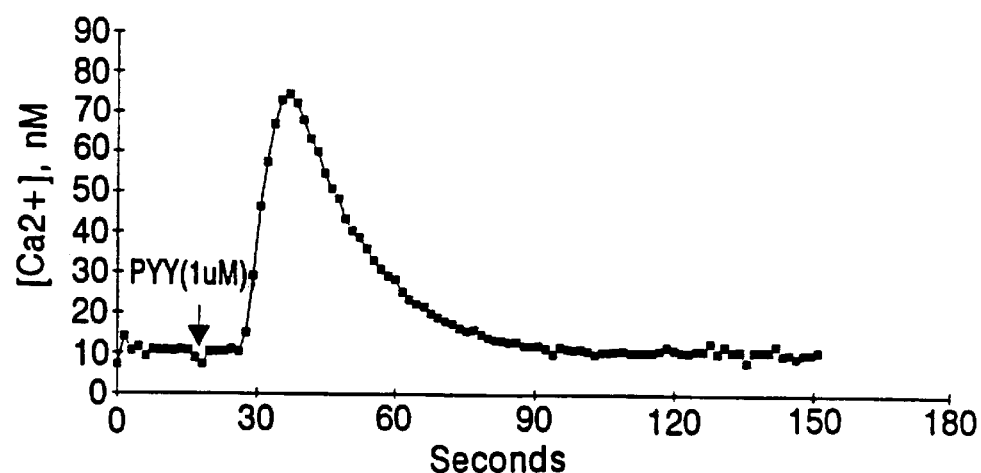
Figure 15C:
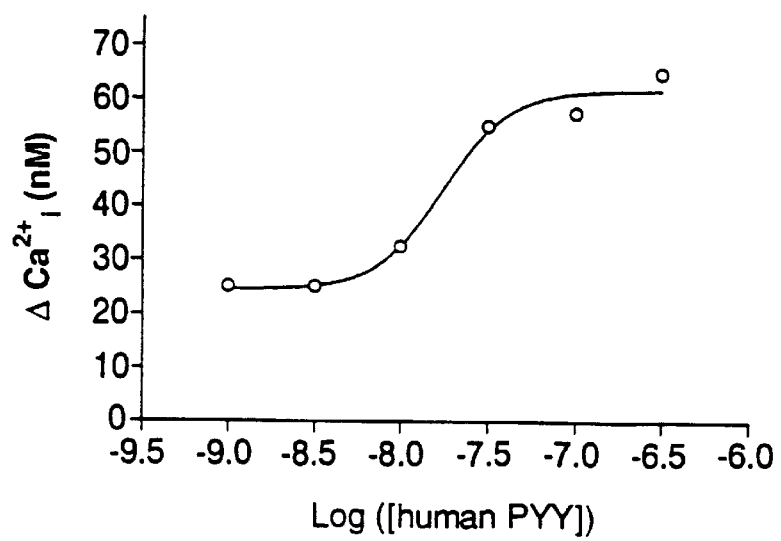

FIGS. 15A–15C Stimulation of intracellular free calcium concentration in intact 293 cells stably expressing the human Y2 receptor. A) Time course. Functional data were derived from Fura-2/AM fluorescence in 293 cells stimulated with 1 μM human PYY at the time indicated by the arrow. B) Time course. Cells were stimulated with 1 μM human PYY as in A except that 1 mM EGTA was included in the extracellular solution. C) Concentration/response curve for PYY-dependent mobilization of intracellular calcium in 293 cells stably transfected with the human Y2 receptor. Data were fit to a four parameter logistic equation by nonlinear regression. Data shown are representative of at least two independent experiments.

Figure 16:
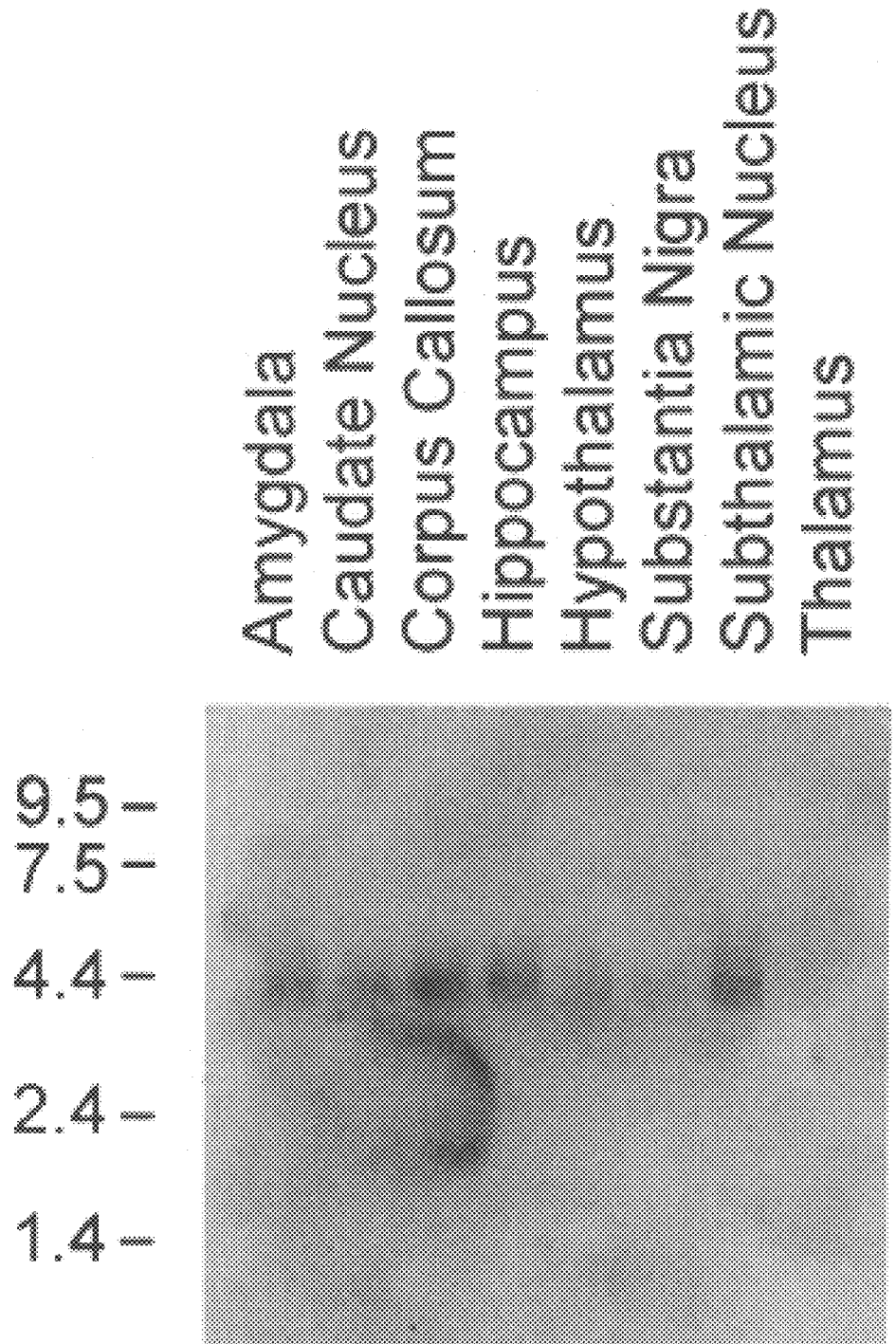

FIG. 16. Northern analysis of various human brain areas. Hybridization was done under conditions of high stringency, as described in Experimental Details. The probe was a $^{32}$P-labeled DNA fragment (specific activity 3×10$^9$ cpm/μg) corresponding to the entire coding region (as shown in FIG.

10) of the human NPY Y2 receptor. The BRL RNA ladder was used as molecular weight markers.

Figure 17:
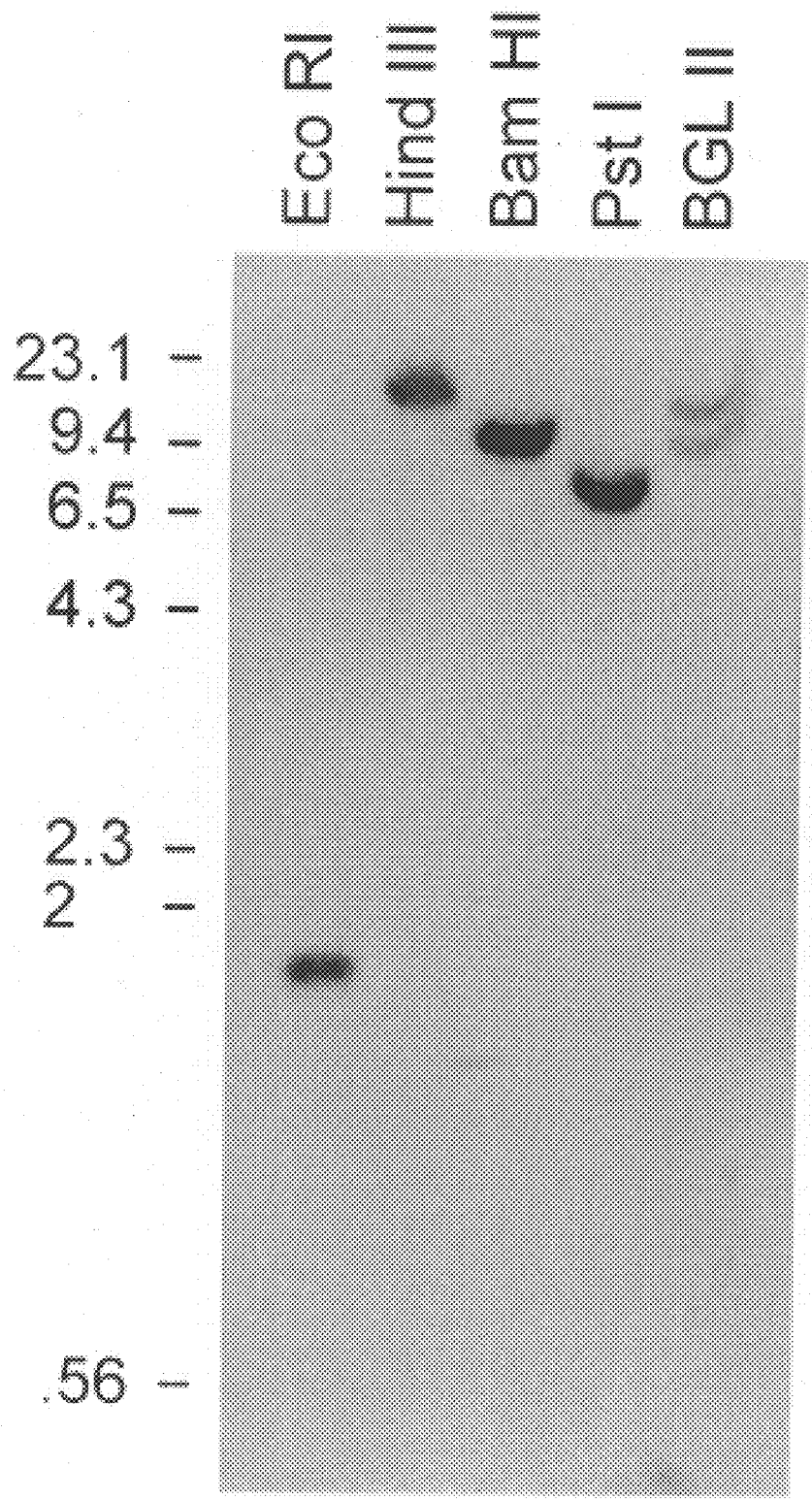

FIG. 17. Southern analysis of genomic DNA encoding the human NPY Y2 receptor subtype. Hybridization was done under conditions of high stringency, as described in Experimental Details. The probe was a $^{32}$P-labeled DNA fragment (specific activity $2.5\times10^9$ cpm/$\mu$g) corresponding to the TM1–TM5 region of the human NPY Y2 receptor (as shown in FIG. 11). Hind III digested $\lambda$ DNA was used as molecular weight markers.

FIGS. 18A–18D Photomicrographs showing some of the controls used for NPY Y2 oligonucleotide probe specificity (A, B), and tissue distribution of the hybridization signal in rat brain (C, D). A. Darkfield photomicrograph of the hybridization signal obtained using the radiolabeled antisense probe on COS-7 cells transfected with the rat Y2 DNA. B. Hybridization signal obtained following hybridization with the radiolabeled sense probe, also on transfected COS-7 cells. Only the antisense probes hybridize to the transfected cells. C. Brightfield photomicrograph of the hybridization signal observed in the CA3 region of the rat hippocampus. Silver grains are found over neuronal cell bodies (arrows) in the pyramidal cell layer (sp), but not over the stratum lucidum (slu) or stratum radiatum (sr). D. Hybridization signal observed over neurons (arrows) in the arcuate nucleus of the hypothalamus. The darkly stained ependymal lining of the third ventricle can be seen to the left of the micrograph (asterisk).

DETAILED DESCRIPTION OF THE INVENTION

Throughout this application, the following standard abbreviations are used to indicate specific nucleotide bases:

C=cytosine
A=adenine
T=thymine
G=guanine

This invention provides isolated nucleic acid molecules which encode Y2 receptors. In one embodiment, the Y2 receptor encoded is a human Y2 receptor. In another embodiment, the Y2 receptor encoded is a rat Y2 receptor. As used herein, the term Y2 receptor encompasses any amino acid sequence, polypeptide or protein having substantially the same pharmacology provided for the subject human Y2 receptor as shown in Tables 2–4 and FIGS. 5A–7B. As described herein our cloned receptor has a Y2 pharmacological profile that differs from the NPY receptor subtypes Y1 and Y3, PYY receptor, and PP receptor, and is therefore designated as the Y2 receptor. The only NPY receptor which has been cloned to date is the Y1 receptor gene, from mouse (Eva et al., 1992), rat (Eva et al., 1990), and human (Larhammar et al., 1992). The human Y2 receptor's greatest homology with any known receptor disclosed in the Genbank/EMBL databases is a 42% overall amino acid identity with the human Y1 receptor.

This invention provides isolated nucleic acid molecules encoding Y2 receptors. In one embodiment, the Y2 receptor is a human Y2 receptor. In another embodiment, the Y2 receptor is a rat Y2 receptor. As used herein, the term "isolated nucleic acid molecule" means a nucleic acid molecule that is a molecule in a form which does not occur in nature. Examples of such an isolated nucleic acid molecule are an RNA, cDNA, or isolated genomic DNA molecule encoding a Y2 receptor. The human Y2 receptor has an amino acid sequence substantially the same as the deduced amino acid sequence shown in FIG. 2 and any human receptor having substantially the same amino acid sequence as the amino acid sequence shown in FIG. 2 is by definition a human Y2 receptor. The rat Y2 receptor has an amino acid sequence substantially the same as the deduced amino acid sequences shown in FIG. 8 or FIG. 9. One means of isolating another Y2 receptor is to probe a genomic library with a natural or artificially designed DNA probe, using methods well known in the art. DNA probes derived from the human and the rat receptor Y2 gene are particularly useful probes for this purpose. DNA and cDNA molecules which encode Y2 receptors may be used to obtain genomic DNA, cDNA or RNA from human, mammalian or other animal sources, or to isolate related cDNA or genomic clones by the screening of cDNA or genomic libraries by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a Y2 receptor. Such molecules may have coding sequences substantially the same as the coding sequences shown in FIGS. 1, 8 and 9. The DNA molecule of FIG. 1 encodes the sequence of the human Y2 receptor gene. The DNA molecules of FIGS. 8 and 9 encode the sequence of two rat Y2 receptor genes.

This invention further provides DNA molecules encoding Y2 receptors having coding sequences substantially the same as the coding sequences shown in FIGS. 1, 8 and 9. These molecules are obtained by the means described above.

This invention also provides an isolated nucleic acid molecule encoding a Y2 receptor wherein the nucleic acid molecule encodes a receptor being characterized by an amino acid sequence in the transmembrane region, which amino acid sequence has 60% homology or higher to the amino acid sequence in the transmembrane region of the human Y2 receptor as shown in FIG. 11.

This invention also provides purified isolated proteins which are Y2 receptors. In one embodiment, the Y2 receptor protein is a human Y2 receptor protein. In another embodiment, the Y2 receptor protein is a rat Y2 receptor protein. As used herein, the term "isolated protein" means a protein molecule free of other cellular components. Examples of such proteins are isolated proteins having substantially the same amino acid sequence as the amino acid sequences shown in FIGS. 2, 8, and 9, which are a human Y2 receptor and two rat Y2 receptors, respectively. One means for obtaining an isolated Y2 receptor is to express DNA encoding the receptor in a suitable host, such as a bacterial, yeast, insect or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides vectors comprising nucleic acid molecules such as DNA, RNA, or cDNA encoding Y2 receptors. In one embodiment, the nucleic acid encodes a human Y2 receptor. In another embodiment, the nucleic acid encodes a rat Y2 receptor. Examples of vectors are viruses such as bacteriophages (such as phage lambda), animal viruses (such as Herpes virus, Murine Leukemia virus, and Baculovirus), cosmids, plasmids (such as pUC18, available from Pharmacia, Piscataway, N.J.), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. Specific examples of such plasmids are: a plasmid comprising cDNA having a coding sequence substantially the same as the coding sequence shown in FIG. 1 and designated clone CG-13 (Seq. I.D. No. 1); or a plasmid comprising genomic DNA having a coding sequence substantially the same as the coding sequence shown in FIG. 8 and designated clone rS5a (Seq. I.D. No. 3), or the coding sequence shown in FIG. 9 and designated clone rS26a (Seq. I.D. No. 5).

This invention also provides vectors comprising nucleic acid molecules encoding Y2 receptors, adapted for expression in a bacterial cell, a yeast cell, an insect cell or a mammalian cell which additionally comprise the regulatory elements necessary for expression of the nucleic acid in the bacterial, yeast, insect or mammalian cells operatively linked to the nucleic acid encoding a Y2 receptor as to permit expression thereof. Nucleic acid having coding sequences substantially the same as the coding sequence shown in FIG. 1 may be usefully inserted into the vectors to express human Y2 receptors. Nucleic acid having coding sequences substantially the same as the coding sequences shown in FIGS. 8 and 9 may be usefully inserted into vectors to express rat Y2 receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Furthermore, an insect expression vector, such as recombinant baculovirus, uses the polyhedron gene expression signals for expression of the inserted gene in insect cells. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial cell, a yeast cell, an insect cell, or, in particular, a mammalian cell which comprises a nucleic acid molecule encoding a Y2 receptor and the regulatory elements necessary for expression of the nucleic acid in the bacterial, yeast, insect, or mammalian cell operatively linked to the nucleic acid encoding the Y2 receptor as to permit expression thereof. In one embodiment, the Y2 receptor is a human Y2 receptor. In another embodiment, the Y2 receptor is a rat Y2 receptor. Some plasmids adapted for expression in a mammalian cell are pSVL (available from Pharmacia, Piscataway, N.J.) and pcEXV-3 (73). One specific example of such a plasmid is a plasmid adapted for expression in a mammalian cell comprising cDNA having a coding sequence substantially the same as the coding sequence shown in FIG. 1 and the regulatory elements necessary for expression of the DNA in the mammalian cell which is designated pcEXV-hY2, deposited on Jan. 27, 1994 under ATCC Accession No. 75659. Other specific examples of such plasmids are plasmids adapted for expression in a mammalian cell comprising genomic DNA having coding sequences substantially the same as the coding sequences shown in FIGS. 8 and 9 and the regulatory elements necessary for expression of the DNA in the mammalian cell which are designated pcEXV-rY2a, deposited on Jan. 25, 1995 under ATCC Accession No. 97035; and pcEXV-rY2b, deposited on Jan. 25, 1995 under ATCC Accession No. 97036, respectively. Those skilled in the art will readily appreciate that numerous plasmids adapted for expression in a mammalian cell which comprise DNA encoding Y2 receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposits discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a cell transfected with and expressing nucleic acid encoding a Y2 receptor. In one embodiment the Y2 receptor is a human Y2 receptor. In another embodiment, the Y2 receptor is a rat Y2 receptor. An example of such a cell is a mammalian cell transfected with a plasmid adapted for expression in a mammalian cell, which comprises nucleic acid encoding a Y2 receptor, and the regulatory elements necessary for expression of the nucleic acid in the mammalian cell operatively linked to the nucleic acid encoding a Y2 receptor as to permit expression thereof; the protein encoded thereby expressed on the cell surface. Numerous mammalian cells may be used as hosts, including, for example, the mouse fibroblast cell NIH-3T3, CHO cells, HeLa cells, LM(tk−) cells, etc. Expression plasmids such as that described supra may be used to transfect cells by methods well known in the art such as calcium phosphate precipitation, or DNA encoding these Y2 receptors may be otherwise introduced into cells, e.g., by microinjection, to obtain mammalian cells which comprise nucleic acid, e.g., cDNA or a plasmid, encoding a Y2 receptor. A specific example of such cells is a cell comprising the pcEXV-hY2 plasmid adapted for expression in a mammalian cell comprising cDNA encoding the Y2 receptor and the regulatory elements necessary for expression of the DNA in the mammalian cell, which is designated 293-hY2-10 and deposited on Jan. 27, 1994 under ATCC Accession No. 11837. Another specific example of such cells is a cell comprising the pcEXV-hY2 plasmid adapted for expression in a mammalian cell comprising cDNA encoding the Y2 receptor and the regulatory elements necessary for expression of the DNA in the mammalian cell, which is designated N-hY2-5 and deposited on Jan. 25, 1995 under ATCC Accession No. CRL-11825.

This invention provides a method for determining whether a ligand can bind specifically to a Y2 receptor which comprises contacting a cell transfected with and expressing nucleic acid encoding a Y2 receptor, the protein encoded thereby is expressed on the cell surface, with the ligand under conditions permitting binding of ligands known to bind to the Y2 receptor, and detecting the presence of any of the ligand bound to the Y2 receptor, thereby determining whether the ligand binds specifically to the Y2 receptor. In one embodiment, the Y2 receptor is a human Y2 receptor. In another embodiment, the Y2 receptor is a rat Y2 receptor.

This invention further provides a method for determining whether a ligand can bind specifically to a Y2 receptor, which comprises contacting a cell transfected with and expressing nucleic acid encoding the Y2 receptor with the ligand under conditions permitting binding of ligands to such receptor, and detecting the presence of any such ligand bound to the Y2 receptor, wherein the Y2 receptor is characterized by an amino acid sequence in the transmembrane region, such amino acid sequence having 60% homology or higher to the amino acid sequence in the transmembrane region of the Y2 receptor shown in FIG. 11. In one embodiment, the Y2 receptor is a human Y2 receptor. In another embodiment, the Y2 receptor is a rat Y2 receptor.

This invention provides a method for determining whether a ligand can bind specifically to a Y2 receptor which comprises preparing a cell extract from cells transfected with and expressing nucleic acid encoding a Y2 receptor, isolating a membrane fraction from the cell extract, contacting the ligand with the membrane fraction from the cell extract under conditions permitting binding of ligands to such receptor, and detecting the presence of any ligand bound to the Y2 receptor, thereby determining whether the compound is capable of binding specifically to a Y2 receptor. In one embodiment, the Y2 receptor is a human Y2 receptor. In another embodiment, the Y2 receptor is a rat Y2 receptor.

This invention also provides a method for determining whether a ligand is a Y2 receptor agonist. As used herein, the term "agonist" means any ligand capable of increasing Y2 receptor functional activity. This comprises contacting a cell transfected with and expressing nucleic acid encoding a Y2 receptor with the ligand under conditions permitting the activation of a functional Y2 receptor response from the cell, and detecting, by means of a bioassay, such as a second messenger assay, an increase in Y2 receptor activity, thereby determining whether the ligand acts as a Y2 receptor agonist. In one embodiment, the Y2 receptor is a human Y2 receptor. In another embodiment, the Y2 receptor is a rat Y2 receptor.

This invention further provides a method for determining whether a ligand is a Y2 receptor agonist which comprises preparing a cell extract from cells transfected with and expressing nucleic acid encoding a Y2 receptor, isolating a membrane fraction from the cell extract, contacting the membrane fraction of the extract with the ligand under conditions permitting the activation of a functional Y2 receptor response, and detecting, by means of a bioassay, such as a second messenger assay, an increase in Y2 receptor activity, thereby determining whether the ligand is a Y2 receptor agonist. In one embodiment, the Y2 receptor is a human Y2 receptor. In another embodiment, the Y2 receptor is a rat Y2 receptor.

This invention also provides a method for determining whether a ligand a Y2 receptor antagonist. As used herein, the term "antagonist" means any ligand capable of decreasing Y2 receptor functional activity. This comprises contacting a cell transfected with and expressing nucleic acid encoding a Y2 receptor with the ligand in the presence of a known Y2 receptor agonist such as NPY, under conditions permitting the activation of a functional Y2 receptor response, and detecting, by means of a bioassay, such as a second messenger assay, a decrease in Y2 receptor activity, thereby determining whether the ligand is a Y2 receptor antagonist. In one embodiment, the Y2 receptor is a human Y2 receptor. In another embodiment, the Y2 receptor is a rat Y2 receptor.

This invention also provides a method for determining whether a ligand is a Y2 receptor antagonist which comprises preparing a cell extract from cells transfected with and expressing nucleic acid encoding a Y2 receptor, isolating a membrane fraction from the cell extract, contacting the membrane fraction of the extract with the ligand in the presence of a known Y2 receptor agonist, such as NPY, under conditions permitting the activation of a functional Y2 receptor response, and detecting, by means of a bioassay, such as a second messenger assay, a decrease in Y2 receptor activity, thereby determining whether the ligand is a Y2 receptor antagonist. In one embodiment, the Y2 receptor is a human Y2 receptor. In another embodiment, the Y2 receptor is a rat Y2 receptor.

In one embodiment, the second messenger assays referred to comprise measurement of intracellular cAMP. In another embodiment, the second messenger assays comprise measurement of intracellular calcium mobilization.

In one embodiment, the nucleic acid in the cells referred to above encodes a Y2 receptor having an amino acid sequence substantially the same as the amino acid sequence shown in FIG. 2. In another embodiment, the nucleic acid in the cells referred to above encodes a Y2 receptor having an amino acid sequence substantially the same as the amino acid sequences shown in FIG. 8 or FIG. 9. In one embodiment, the cell is a mammalian cell. Preferably, the mammalian cell is non-neuronal in origin. An example of a nonneuronal mammalian cell is a COS-7 cell. Other examples of a non-neuronal mammalian cells that can be used for functional assays with Y2 receptors are the 293 human embryonic kidney cells, mouse embryonic fibroblast NIH-3T3 cells, and LM(tk–) cells.

The preferred method for determining whether a ligand is capable of binding specifically to a Y2 receptor comprises contacting a transfected nonneuronal mammalian cell (i.e. a cell that does not naturally express any type of NPY, PP, or PYY receptor, and thus will only express such a receptor if it is transfected into the cell) expressing a Y2 receptor on its surface, or contacting a membrane preparation derived from such a transfected cell, with the ligand under conditions which are known to prevail, and thus to be associated with, in vivo binding of the ligand to and/or activation of a Y2 receptor, and detecting the presence of any of the ligand being tested bound to the Y2 receptor on the surface of the cell, or detecting activation of the Y2 receptor, thereby determining whether the ligand binds to, activates or inhibits the activation of the Y2 receptor. Activation of a Y2 receptor may be detected by means of a second messenger assay. Such a response system is obtained by transfection of nucleic acid into a suitable host cell containing the desired second messenger system such as phospholipase C, adenylate cyclase, guanylate cyclase or ion channels. A suitable host cell can be isolated from pre-existing cell lines, or can be generated by inserting appropriate components of second messenger systems into existing cell lines. Such a transfected cell provides a complete response system for investigation or assay of the activity of Y2 receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for Y2 receptor activity and competitive binding assays. Functional assays of signal transduction pathways in transfection systems determine a ligand's efficacy of activating the receptor. A transfection system constitutes a "drug discovery system"

useful for the identification of natural or synthetic compounds with potential for drug development that can be further modified or used directly as therapeutic compounds to activate or inhibit the natural functions of the Y2 receptor. The transfection system is also useful for determining the affinity and efficacy of known drugs at the Y2 receptor sites.

This invention provides a pharmaceutical composition comprising an effective amount of the Y2 receptor agonist determined by the methods described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. In one embodiment, the Y2 receptor is a human Y2 receptor. In another embodiment, the Y2 receptor is a rat Y2 receptor. In a further embodiment, the Y2 receptor agonist is not previously known.

This invention further provides a pharmaceutical composition comprising an effective amount of the Y2 receptor antagonist determined by the methods described above and a pharmaceutically acceptable carrier. In one embodiment the Y2 receptor is a human Y2 receptor. In another embodiment, the Y2 receptor is a rat Y2 receptor. In a further embodiment, the Y2 receptor antagonist is not previously known.

This invention also provides a method of screening drugs to identify drugs which specifically bind to a Y2 receptor on the surface of a cell which comprises contacting a cell transfected with and expressing nucleic acid encoding the Y2 receptor with a plurality of drugs under conditions permitting binding of drugs to the Y2 receptor, and determining those drugs which bind specifically to the cell, thereby identifying drugs which specifically bind to a Y2 receptor. In one embodiment, the Y2 receptor is a human Y2 receptor. In another embodiment, the Y2 receptor is a rat Y2 receptor.

This invention also provides a method of screening drugs to identify drugs which specifically bind to a Y2 receptor on the surface of a cell which comprises preparing a cell extract from the cells transfected with and expressing nucleic acid encoding the Y2 receptor, isolating a membrane fraction from the cell extract, contacting the membrane fraction with a plurality of drugs under conditions permitting binding of drugs to the Y2 receptor, and determining those drugs which bind specifically to the transfected cell, thereby identifying drugs which bind specifically to a Y2 receptor. In one embodiment, the Y2 receptor is a human Y2 receptor. In another embodiment, the Y2 receptor is a rat Y2 receptor.

This invention also provides a method of screening drugs to identify drugs which act as Y2 receptor agonists which comprises contacting a cell transfected with and expressing nucleic acid encoding a Y2 receptor with a plurality of drugs under conditions permitting the activation of a functional Y2 receptor response, and determining those drugs which activate such Y2 receptor, using a bioassay, such as a second messenger assay, thereby identifying drugs which act as Y2 receptor agonists. In one embodiment, the Y2 receptor is a human Y2 receptor. In another embodiment the Y2 receptor is a rat Y2 receptor. In a further embodiment, the Y2 receptor agonist is not previously known.

This invention provides a method of screening drugs to identify drugs which act as agonists of a Y2 receptor which comprises preparing a cell extract from cells transfected with and expressing nucleic acid encoding a Y2 receptor, isolating a membrane fraction from the cell extract, contacting the membrane fraction with a plurality of drugs under conditions permitting the activation of a functional Y2 receptor response, and determining those drugs which activate such receptor, using a bioassay, such as a second messenger assay, thereby identifying drugs which act as Y2 receptor agonists. In one embodiment, the Y2 receptor is a human Y2 receptor. In another embodiment, the Y2 receptor is a rat Y2 receptor. In a further embodiment, the Y2 receptor agonist is not previously known.

This invention also provides a method of screening drugs to identify drugs which act as Y2 receptor antagonists which comprises contacting a cell transfected with and expressing nucleic acid encoding a Y2 receptor with a plurality of drugs in the presence of a known Y2 receptor agonist such as NPY under conditions permitting the activation of a functional Y2 receptor response, and determining those drugs which inhibit the activation of the receptor, using a bioassay, such as a second messenger assay, thereby identifying drugs which act as Y2 receptor antagonists. In one embodiment, the Y2 receptor is a human Y2 receptor. In another embodiment, the Y2 receptor is a rat Y2 receptor. In a further embodiment, the Y2 receptor antagonist is not previously known.

This invention provides a method of screening drugs to identify drugs which act as Y2 receptor antagonists which comprises preparing a cell extract from cells transfected with and expressing nucleic acid encoding a Y2 receptor, isolating a membrane fraction from the cell extract, contacting the membrane fraction with a plurality of drugs in the presence of a known Y2 receptor agonist, such as NPY, under conditions permitting the activation of a functional Y2 receptor response, and determining those drugs which inhibit the activation of the receptor using a bioassay, such as a second messenger assay, thereby identifying drugs which act as Y2 receptor antagonists. In one embodiment, the Y2 receptor is a human Y2 receptor. In another embodiment, the Y2 receptor is a rat Y2 receptor. In a further embodiment, the Y2 receptor antagonist is not previously known.

In one embodiment of the above described methods, the second messenger assay comprises measurement of intracellular cAMP. In another embodiment, the second messenger assay comprises measurement of intracellular calcium mobilization.

The nucleic acid in the cells of the methods described above may have a coding sequence substantially the same as the coding sequences shown in FIGS. 1, 8 and 9. Preferably, the mammalian cell is nonneuronal in origin. An example of a nonneuronal mammalian cell is an COS-7 cell. Other examples of a non-neuronal mammalian cell to be used for functional assays are 293 human embryonic kidney cells, mouse embryonic fibroblast NIH-3T3 cells and LM(tk−) cells. Drug candidates are identified by choosing chemical compounds which bind with high affinity to the expressed Y2 receptor protein in transfected cells, using radioligand binding methods well known in the art, examples of which are shown in the binding assays described herein. Drug candidates are also screened for selectivity by identifying compounds which bind with high affinity to the Y2 receptor but do not bind with high affinity to any other NPY receptor subtype or to any other known receptor site. Because selective, high affinity compounds interact primarily with the target Y2 receptor site after administration to the patient, the chances of producing a drug with unwanted side effects are minimized by this approach.

This invention provides a pharmaceutical composition comprising an effective amount of a drug identified by the methods described above and a pharmaceutically acceptable carrier.

As used herein, an "effective amount" is an amount of the drug effective to produce the desired result in a subject when administered in accordance with the chosen regimen. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention also provides a method of treating an abnormality in a subject, wherein the abnormality is alleviated by activation of a Y2 receptor which comprises administering to a subject an effective amount of the pharmaceutical composition described above, thereby treating the abnormality. In one embodiment, the Y2 receptor is a human Y2 receptor. In another embodiment, the Y2 receptor is a rat Y2 receptor.

As used herein, the term "effective amount" means that amount of a drug which is able to produce the desired result in a subject when administered in accordance with the chosen regimen. Typically, an effective amount is an amount from about 0.01 mg per subject per day to about 500 mg per subject per day. More typically this amount is an amount from about 0.1 mg per subject per day to about 60 mg per subject per day. Most typically, this amount is an amount from about 1 mg per subject per day to about 20 mg per subject per day. Optimal dosages to be administered may be determined by those skilled in the art, and will vary with the particular drug in use, the strength of the preparation, the mode of administration, and the advancement of the disease condition. Additional factors depending on the particular subject being treated will result in a need to adjust dosages, including subject age, weight, gender, diet, and time of administration.

This invention provides a method of treating an abnormality in a subject wherein the abnormality is alleviated by activation of a Y2 receptor which comprises administering to a subject an effective amount of a Y2 receptor agonist determined by the methods described above, thereby treating the abnormality. In one embodiment, the Y2 receptor is a human Y2 receptor. In another embodiment, the Y2 receptor is a rat Y2 receptor.

This invention further provides a method of treating an abnormality in a subject, wherein the abnormality is alleviated by decreasing the activity of a Y2 receptor which comprises administering to a subject an effective amount of the pharmaceutical composition described above, thereby treating the abnormality. In one embodiment, the Y2 receptor is a human Y2 receptor. In another embodiment, the Y2 receptor is a rat Y2 receptor.

This invention also provides a method of treating an abnormality in a subject, wherein the abnormality is alleviated by decreasing the activity of a Y2 receptor which comprises administering to the subject an effective amount of a Y2 receptor antagonist determined by the methods described above, thereby treating the abnormality. In one embodiment, the Y2 receptor is a human Y2 receptor. In another embodiment, the Y2 receptor is a rat Y2 receptor.

This invention provides a nucleic acid probe comprising a nucleic acid molecule of at least 15 nucleotides capable of specifically hybridizing with a unique sequence included within the sequence of a nucleic acid molecule encoding a Y2 receptor, for example with a coding sequence included within the sequences shown in FIGS. 1, 8 and 9. As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the Y2 receptor. In one embodiment the Y2 receptor is a human Y2 receptor. In another embodiment, the Y2 receptor is a rat Y2 receptor. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding Y2 receptors is useful as a diagnostic test for any disease process in which levels of expression of the corresponding Y2 receptor is altered. DNA probe molecules are produced by insertion of a DNA molecule which encodes Y2 receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1, 8 and 9. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a Y2 receptor are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the Y2 gene by in situ hybridization.

This invention also provides a method of detecting expression of a Y2 receptor by detecting the presence of mRNA coding for a Y2 receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding the Y2 receptor under hybridizing conditions, and detecting the presence of mRNA hybridized to the probe, thereby detecting the expression of the Y2 receptor by the cell. In one embodiment, the Y2 receptor is a human Y2 receptor. In another embodiment, the Y2 receptor is a rat Y2 receptor. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of specifically hybridizing to an mRNA molecule which encodes a Y2 receptor so as to prevent translation of the mRNA molecule. The antisense oligonucleotide may have a sequence capable of specifically hybridizing with the cDNA molecule whose sequence is shown in FIG. 1, or with the genomic DNA molecule whose sequences are shown in FIGS. 8 and 9. A particular example of an antisense oligonucleotide is an antisense oligonucleotide comprising chemical analogues of nucleotides.

This invention also provides a pharmaceutical composition comprising an amount of the oligonucleotide described above effective to decrease activity of a Y2 receptor by passing through a cell membrane and specifically hybridizing with mRNA encoding a Y2 receptor in the cell so as to prevent its translation and a pharmaceutically acceptable carrier capable of passing through a cell membrane. The oligonucleotide may be coupled to a substance which inactivates mRNA, such as a ribozyme. The pharmaceutically acceptable carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. In one embodiment, the Y2 receptor is a human Y2 receptor. In another embodiment, the Y2 receptor is a rat Y2 receptor. DNA molecules having coding sequences substantially the same as the coding sequences shown in FIGS. 1, 8 and 9 may be used as the oligonucleotides of the pharmaceutical composition.

This invention also provides a method of treating an abnormality in a subject wherein the abnormality is alleviated by decreasing the activity of a Y2 receptor which comprises administering to the subject an effective amount of the pharmaceutical composition described above, thereby treating the abnormality. In one embodiment, the Y2 receptor is a human Y2 receptor. In another embodiment, the Y2 receptor is a rat Y2 receptor. Several examples of such abnormalities are hypertension, gastrointestinal disorders, epilepsy, sleep disorders, and cognitive disorders, (58–80).

Antisense oligonucleotide drugs inhibit translation of mRNA encoding these receptors. Synthetic oligonucleotides, or other antisense chemical structures are designed to bind to mRNA encoding the Y2 receptor and inhibit translation of mRNA and are useful as drugs to inhibit expression of Y2 receptor genes in patients. This invention provides a means to therapeutically alter levels of expression of Y2 receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIGS. 1, 8, and 9 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequences shown in FIGS. 1, 8, and 9 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (74,75). In addition, coupling of ribozymes to antisense oligonucleotides is a promising strategy for inactivating target mRNA (76). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of Y2 receptors.

This invention provides an antibody directed to a Y2 receptor, for example, a monoclonal antibody directed to an epitope of a Y2 receptor present on the surface of a cell and having an amino acid sequence substantially the same as an amino acid sequence for a cell surface epitope of the Y2 receptor included in the amino acid sequences shown in FIGS. 2, 8 and 9 (Seq. I.D. Nos. 2, 4, and 6, respectively). In one embodiment, the Y2 receptor is a human Y2 receptor. In another embodiment, the Y2 receptor is a rat Y2 receptor. Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 2, 8, and 9 will probably bind to a surface epitope of a Y2 receptor, as described. Antibodies directed to Y2 receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as COS-7 cells, LM(tk–) cells, NIH-3T3 cells or 293 human embryonic cells comprising DNA encoding the Y2 receptor and thereby expressing the Y2 receptor may be used as immunogens to raise such an antibody. Alternatively, synthetic peptides may be prepared using commercially available machines and the amino acid sequences shown in FIGS. 2, 8, and 9 (Seq. I.D. Nos. 2, 4, and 6, respectively). As a still further alternative, DNA, such as a cDNA or a fragment thereof, may be cloned and expressed and the resulting polypeptide recovered and used as an immunogen. These antibodies are useful to detect the presence of Y2 receptors encoded by the isolated DNA, or to inhibit the function of the receptors in living animals, in humans, or in biological tissues or fluids isolated from animals or humans.

This invention provides a pharmaceutical composition which comprises an amount of an antibody directed to a Y2 receptor effective to block binding of ligands to the Y2 receptor, and a pharmaceutically acceptable carrier. A monoclonal antibody directed to an epitope of a Y2 receptor present on the surface of a cell and having an amino acid sequence substantially the same as an amino acid sequence for a cell surface epitope of the Y2 receptor included in the amino acid sequences shown in FIGS. 2, 8 and 9 are useful for this purpose.

This invention also provides a method of treating an abnormality in a subject, wherein the abnormality is alleviated by decreasing the activity of a Y2 receptor which comprises administering to the subject an amount of the pharmaceutical composition described above effective to block binding of ligands to the Y2 receptor, thereby treating the abnormality. In a one embodiment, the Y2 receptor is a human Y2 receptor. In another embodiment, the Y2 receptor is a rat Y2 receptor. Binding of the antibody to the receptor prevents the receptor from functioning, thereby neutralizing the effects of activity of the receptor. The monoclonal antibodies described above are both useful for this purpose. Some examples of such abnormalities are hypertension, gastrointestinal disorders, epilepsy, sleep disorders, and cognitive disorders (58–72).

This invention provides a method of detecting the presence of a Y2 receptor on the surface of a cell which comprises contacting the cell with an antibody directed to the Y2 receptor, under conditions permitting binding of the antibody to the receptor, and detecting the presence of the antibody bound to the cell, thereby detecting the presence of a Y2 receptor on the surface of the cell. Such a method is useful for determining whether a given cell is defective in expression of Y2 receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing nucleic acid encoding a Y2 receptor. In one embodiment, the Y2 receptor is a human Y2 receptor. In another embodiment, the Y2 receptor is a rat Y2 receptor. This invention also provides a transgenic nonhuman mammal comprising a homologous recombination knockout of the native Y2 receptor. This invention also provides a transgenic nonhuman mammal whose genome comprises antisense nucleic acid complementary to nucleic acid encoding a Y2 receptor so placed as to be transcribed into antisense mRNA which is complementary to mRNA encoding a Y2 receptor and which hybridizes to mRNA encoding a Y2 receptor thereby reducing its translation.

The nucleic acid may additionally comprise an inducible promoter or additionally comprise tissue specific regulatory elements, so that expression can be induced, or restricted to specific cell types. Examples of nucleic acid are DNA or cDNA molecules having a coding sequence substantially the same as the coding sequences shown in FIGS. 1, 8, and 9. An example of a transgenic animal is a transgenic mouse. Examples of tissue specificity-determining regions are the metallothionein promotor (77) and the L7 promotor (78).

Animal model systems which elucidate the physiological and behavioral roles of Y2 receptors are produced by creating transgenic animals in which the activity of a Y2 receptor is either increased or decreased, or the amino acid sequence of the expressed Y2 receptor protein is altered, by a variety of techniques. Examples of these techniques include: 1) Insertion of normal or mutant versions of nucleic acid encoding a Y2 receptor or homologous animal versions of these genes, by microinjection, retroviral infection or other means well known to those skilled in the art, into appropriate fertilized embryos in order to produce a transgenic animal (79). 2) Homologous recombination (80, 81) of mutant or normal, human or animal versions of these genes with the native gene locus in transgenic animals to alter the regulation of expression or the structure of these Y2 receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (79). DNA or cDNA encoding a Y2 receptor is purified from a vector (such as plasmid pcEXV-hY2, pcEXV-rY2a or pcEXV-rY2b described above) by methods well known in the art. Inducible promoters may be fused with the coding region of the nucleic acid to provide an experimental means to regulate expression of the transgene. Alternatively, or in addition, tissue specific regulatory elements may be fused with the coding region to permit tissue-specific expression of the trans-gene. The nucleic acid, in an appropriately buffered solution, is put into a microinjection needle (which may be made from capillary tubing using a pipet puller) and the egg to be injected is put in a depression slide. The needle is inserted into the pronucleus of the egg, and the nucleic acid solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting nucleic acid into the egg cell, and is used here only for exemplary purposes.

Since the normal action of receptor-specific drugs is to activate or to inhibit the receptor, the transgenic animal model systems described above are useful for testing the biological activity of drugs directed against these Y2 receptors even before such drugs become available. These animal model systems are useful for predicting or evaluating possible therapeutic applications of drugs which activate or inhibit these Y2 receptors by inducing or inhibiting expression of the native or trans-gene and thus increasing or decreasing activity of normal or mutant Y2 receptors in the living animal. Thus, a model system is produced in which the biological activity of drugs directed against these Y2 receptors are evaluated before such drugs become available. The transgenic animals which over or under produce the Y2 receptor indicate by their physiological state whether over or under production of the Y2 receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to decreased activity. Therefore, an animal which has decreased receptor activity is useful as a test system to investigate whether the actions of such drugs which result in decreased activity are in fact therapeutic. Another use is that if increased activity is found to lead to abnormalities, then a drug which down-regulates or acts as an antagonist to a Y2 receptor is indicated as worth developing, and if a promising therapeutic application is uncovered by these animal model systems, activation or inhibition of the Y2 receptor is achieved therapeutically either by producing agonist or antagonist drugs directed against these Y2 receptors or by any method which increases or decreases the activity of these Y2 receptors in humans or other mammals.

This invention provides a method of determining the physiological effects of expressing varying levels of Y2 receptors which comprises producing a transgenic nonhuman animal whose levels of Y2 receptor expression are varied by use of an inducible promoter which regulates Y2 receptor expression. This invention also provides a method of determining the physiological effects of expressing varying levels of Y2 receptors which comprises producing a panel of transgenic nonhuman animals each expressing a different amount of Y2 receptor. In one embodiment, the Y2 receptor is a human Y2 receptor. In another embodiment, the Y2 receptor is a rat Y2 receptor. Such animals may be produced by introducing different amounts of nucleic acid encoding a Y2 receptor into the oocytes from which the transgenic animals are developed.

This invention also provides a method for identifying a Y2 receptor antagonist capable of alleviating an abnormality is a subject, wherein the abnormality is alleviated by decreasing the acitivity of a Y2 receptor which comprises administering the antagonist to a transgenic nonhuman mammal described above and determining whether the antagonist alleviates the physical and behavioral abnormalities displayed by the transgenic nonhuman mammal as a result of the activity of a Y2 receptor, thereby identifying a Y2 antagonist. In one embodiment, the Y2 receptor is a human Y2 receptor, In another embodiment, the Y2 receptor is a rat Y2 receptor. This invention further provides an antagonist identified by the method described above. Examples of nucleic acid molecules are DNA or cDNA molecules having a coding sequence substantially the same as the coding sequences shown in FIGS. 1, 8, and 9.

This invention provides a pharmaceutical composition comprising an amount of the antagonist described supra effective to alleviate an abnormality wherein the abnormality is alleviated by decreasing the activity of a Y2 receptor and a pharmaceutically acceptable carrier.

This invention further provides a method for treating an abnormality in a subject wherein the abnormality is alleviated by decreasing the activity of a Y2 receptor which comprises administering to the subject an effective amount of the pharmaceutical composition described above, thereby treating the abnormality.

This invention provides a method for identifying a Y2 receptor agonist capable of alleviating an abnormality wherein the abnormality is alleviated by activation of a Y2 receptor which comprises administering the agonist to the transgenic nonhuman mammal described above and determining whether the agonist alleviates the physical and behavioral abnormalities displayed by the transgenic non-human mammal, thereby identifying a Y2 receptor agonist. In one embodiment, the Y2 receptor is a human Y2 receptor. In another embodiment, the Y2 receptor is a rat Y2 receptor. This invention further provides an agonist identified by the method described above.

This invention also provides a pharmaceutical composition comprising an effective amount of a Y2 receptor agonist identified by the method described above and a pharmaceutically acceptable carrier.

This invention further provides a method for treating an abnormality in a subject wherein the abnormality is alleviated by activation of a Y2 receptor which comprises administering to the subject an effective amount of the pharmaceutical composition described above, thereby treating the abnormality.

This invention provides a method for diagnosing a predisposition to a disorder associated with the expression of a specific Y2 receptor allele which comprises: a) obtaining nucleic acid of subjects suffering from the disorder; b) performing a restriction digest of the nucleic acid with a panel of restriction enzymes; c) electrophoretically separating the resulting nucleic acid fragments on a sizing gel; d) contacting the resulting gel with a nucleic acid probe capable of specifically hybridizing to nucleic acid encoding a Y2 receptor and labelled with a detectable marker; e) detecting labelled bands which have hybridized to the nucleic acid encoding a Y2 receptor labelled with a detectable marker to create a unique band pattern specific to the nucleic acid of subjects suffering from the disorder; f) preparing nucleic acid obtained for diagnosis by steps a–e; and g) comparing the unique band pattern specific to the nucleic acid of subjects suffering from the disorder from step e and the nucleic acid obtained for diagnosis from step f to determine whether the patterns are the same or different and thereby to diagnose predisposition to the disorder if the patterns are the same. This method may also be used to diagnose a disorder associated with the expression of a specific Y2 receptor allele. In one embodiment, the Y2 receptor is a human Y2 receptor. In another embodiment, the Y2 receptor is a rat Y2 receptor.

This invention provides a method of preparing the isolated, purified Y2 receptor which comprises a) constructing a vector adapted for expression in a cell which comprises the regulatory elements necessary for the expression of nucleic acid in the cell operatively linked to the nucleic acid encoding a Y2 receptor as to permit expression thereof, wherein the cell is selected form the group consisting of bacterial cells, yeast cells, insect cells and mammalian cells; b) inserting the vector of step (a) in a suitable host cell; c) incubating the cells of step (b) under conditions allowing the expression of a Y2 receptor; d) recovering the receptor so produced; and e) purifying the receptor so recovered. An example of an isolated Y2 receptor is an isolated protein having substantially the same amino acid sequence as the amino acid sequences shown in FIGS. 2, 8 and 9. For example, cells can be induced to express receptors by exposure to substances such as hormones. The cells can then be homogenized and the receptor isolated from the homogenate using an affinity column comprising, for example, PYY or NPY or another substance which is known to bind to the receptor. The resulting fractions can then be purified by contacting them with an ion exchange column, and determining which fraction contains receptor activity or binds anti-receptor antibodies.

The above described method for preparing a Y2 receptor uses recombinant DNA technology methods well known in the art. For example, isolated nucleic acid encoding Y2 receptor is inserted in a suitable vector, such as an expression vector. A suitable host cell, such as a bacterial cell, or a eukaryotic cell such as a yeast cell, is transfected with the vector. Y2 receptor is isolated from the culture medium by affinity purification or by chromatography or by other methods well known in the art.

This invention identifies for the first time a new receptor protein, its amino acid sequence, its human gene and its rat homologue. Furthermore, this invention describes a previously unrecognized group of receptors within the definition of a Y2 receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolation of a human genomic clone encoding a Y2 receptor. A new human gene for the receptor identified herein as Y2 has been identified and characterized. In addition, the human Y2 receptor has been expressed in 293 human embryonic kidney cells. The pharmacological binding properties of the protein encoded have been determined, and these binding properties classify this protein as a novel human NPY/PYY receptor which we designate as a human Y2 receptor. Mammalian cell lines expressing this human Y2 receptor at the cell surface have been constructed, thus establishing the first well-defined, cultured cell lines with which to study this Y2 receptor.

This invention will be better understood by reference to the Experimental Details which follow, but those skilled in the art will readily appreciate that the specific experiments detailed are only illustrative of the invention as described more fully in the claims which follow thereafter.

Experimental Details cDNA Cloning

Total RNA was prepared by a modification of the guanidine thiocyanate method (13), from 6 grams of human hippocampus. Poly A$^+$RNA was purified with a FastTrack kit (Invitrogen Corp., San Diego, Calif.). Double stranded (ds) cDNA was synthesized from 4 μg of poly A$^+$RNA according to Gubler and Hoffman (14), except that ligase was omitted in the second strand cDNA synthesis. The resulting DS cDNA was ligated to BstxI/EcoRI adaptors (Invitrogen Corp.), the excess of adaptors was removed by chromatography on Sephacryl 500 HR (Pharmacia-LKB) and the ds-cDNA size selected by chromatography on Sephacryl 1000 (Pharmacia-LKB). High molecular weight fractions were ligated in pcEXV.BS (An Okayama and Berg expression vector) cut by BstxI as described by Aruffo and Seed (15). The ligated DNA was electroporated in E. coli MC 1061 (Gene Pulser, Biorad). A total of 2.2×10$^6$ independent clones with an insert mean size of 3 kb could be generated. The library was plated on Petri dishes (Ampicillin selection) in pools of 0.4 to 1.2×10$^4$ independent clones. After 18 hours amplification, the bacteria from each pool were scraped, resuspended in 4 mL of LB media and 1.5 mL processed for plasmid purification by the alkali method (16). 1 mL aliquots of each bacterial pool were stored at −85° C. in 20% glycerol.

Isolation of a cDNA Clone Encoding a Human Hippocampal Y2 Receptor

DNA from pools of ≈5000 independent clones was transfected into COS-7 cells by a modification of the DEAE-dextran procedure (17). COS-7 cells were grown in Dulbecco's Modified Eagle Medium (DMEM) supplemented with 10% fetal calf serum, 100 U/mL of penicillin, 100 μg/mL of streptomycin, 2mM L-glutamine (DMEM-C) at 37° C. in 5% CO$_2$. The cells were seeded one day before transfection at a density of 30,000 cells/cm$^2$ in 6 well plates (Becton Dickinson, Lincoln Park, N.J.). On the next day, cells were washed twice with Phosphate Buffer Saline (PBS), 400 μl of transfection cocktail was added containing 1/10 of the DNA from each pool and DEAE-dextran (500 μg/mL) in PBS. After a 30 min. incubation at 37° C., 1.6 mL of chloroquine (80 μM in DMEM-C) was added and the cells incubated a further 2.5 hours at 37° C. The media was aspirated from each well and 1 mL of 10% DMSO in DMEM-C added. After 2.5 min. incubation at room temperature, the media was aspirated, each well washed once with 1 mL PBS and the cells incubated 24 hours in DMEM-C. The cells were then trypsinized and seeded on Lab-Tek chamber slides (1 chamber, Permanox slide from Nunc Inc., Naperville, Ill.), incubated in 2 ml DMEM-C for another 24 hours and the binding assay was performed on the slides.

After two washes with PBS, positive pools were identified by incubating the cells with 1 nM (3×10$^6$ cpm per slide) of porcine [$^{125}$I]-PYY (New England Nuclear; specific activity=2200 Ci/mmol) in 20 mM Hepes-NaOH pH 7.4, CaCl$_2$ 1.26 mM, MgSO$_4$ 0.81 mM, KH$_2$PO$_4$ 0.44 mM, KCl 5.4, NaCl 10 mM, 0.1% bovine serum albumin, 0.1% bacitracin for 1 hour at room temperature. After six washes (five seconds each) in binding buffer without ligand, the monolayers were fixed in 2.5% glutaraldehyde in PBS for five minutes, washed twice two minutes in PBS, dehydrated in ethanol baths for two minutes each (70, 80, 95, 100%) and air dried.

The slides were then dipped in 100% photoemulsion (Kodak type NTB2) at 42° C. and exposed in the dark for 48 hours at 4° C. in light proof boxes containing drierite. Slides were developed for three minutes in Kodak D19 developer (32 g/l of water), rinsed in water, fixed in Kodak fixer for 5 minutes, rinsed in water, air dried and mounted with Aqua-Mount (Lerner Laboratories, Pittsburgh, Pa.). Slides were screened at 25×total magnification.

A single clone, CG-13, was isolated by sib selection as described (18). DS-DNA was sequenced with a Sequenase kit (US Biochemical, Cleveland, Ohio) according to the manufacturer. Nucleotide and peptide sequences analysis were performed with GCG programs (Genetics Computer group, Madison, Wis.).

Northern Blot

A multiple tissue Northern blot (MTN blot, Contech, Palo Alto, Calif.) carrying mRNA purified from various human brain areas was hybridized at high stringency according to the manufacturer's specifications. The probe was a 1.15 kb DNA fragment corresponding to the entire coding region of the human Y2 receptor as shown in FIG. 10.

Southern Blot

A Southern blot (Geno-Blot, Clontech, Palo Alto, Calif.) containing human genomic DNA cut with five different enzymes (8 μg DNA per lane) was hybridized at high stringency according to the manufacturer's specifications. The probe was a DNA fragment corresponding to the TM1–TM5 coding region of the human Y2 receptor, as shown in FIG. 11.

Cloning and Expression of Two Isoforms of the Rat NPY/PYY (Y2) Receptor

To obtain the rat homologue of the human NPY/PYY (Y2) receptor, we designed and synthesized oligonucleotide probes derived from the nucleotide sequences corresponding approximately to the transmembrane (TM) regions of the amino acid sequence of the human Y2 receptor (TM1–7) as shown in FIG. 11. The overlapping oligomers used were as follows:

(TM1: nts. #190–257, (+) strand/5'-CAAGTTGTTCTCATATTGGCCTACTGCTCCATCA-TCTTGCTTGGGGTAAT-3' (Seq. I.D. No. 7) and (−) strand/5'-ATCACCACATGGATCACCAA-GGAGTTGCCAATTACCCCAAGCAAGATGAT-3' (Seq. I.D. No. 8)

TM2: nts. #301–370, (+) strand/5'-TTTTTCATTGCCAATCTGGCTGTGGCAGATC-TTTTGGTGAACACT-3' (Seq. I.D. No. 9) and (−) strand/ 5'-AGGTAAGAGTGAACGGTAGACACAGAGTGTT-CACCAAAAGATCTG-3' (Seq. I.D. No. 10).

TM3: nts. #411–480, (+) strand/5'-CCACCTGGTGCCCTATGCCCAGGGCCTGGCAG-TACAAGTATCCAC-3' (Seq. I.D. No. 11) and (−) strand/ 5'-CAGGGCAATTACTGTCAAGGTGATTGTGGATA-CTTGTACTGCCAG-3' (Seq. I.D. No. 12).

TM4: nts. #531–600, (+) strand/5'-AATCAGCTTCCTGATTATTGGCTTGGCCTGGGG-CATCAGTGCCCT-3' (Seq. I.D. No. 13) and (−) strand/ 5'-GAAGATGGCCAGGGGACTTGCCAGCAGGGCA-CTGATGCCCCAGGC-3' (Seq. I.D. No. 14)

TM5: nts. #691–760, (+) strand/5'-ACTGTCTATAGTCTTTCTTCCTTGTTGATCTTGT-ATGTTTTGCCT-3' (Seq. I.D. No. 15) and (−) strand/5'-TGTAGGAAAATGATATAATGCCCAGAGGCAAA-CATACAAGATCA-3' (Seq. I.D. NO. 16)

TM6: nts. #850–919, (+) strand/5'-CTGGTGTGTGTGGTGGTGGTGTTTGCGGTCAGC-TGGCTGCCTCTC-3' (Seq. I.D. No. 17) and (−) strand/ 5'-TGTCAACGGCAAGCTGGAAGGCATGGAGA-GGCAGCCAGCTGACCG-3' (Seq. I.D. No. 18)

TM7: NTS. #955–1028, (+) strand/5'-CTCATCTTCACAGTGTTCCACATCATCGCCATGT-GCTCCACTTTTGC-3' (Seq. I.D. No. 19) and (−) strand/ 5'-TTCATCCAGCCATAGAGAAGGGGATTGGC-AAAAGTGGAGCACATGGC-3' (Seq. I.D. No. 20).

The probes were labeled with $[^{32}P]$-ATP and $[^{32}p]$-CTP by synthesis with the large fragment of DNA polymerase.

Hybridization was performed at 40° C. in a solution containing 25% formamide, 10% dextran sulfate, 5× SSC (1× SSC is 0.15 M sodium chloride, 0.015 M sodium citrate), 1× Denhardt's (0.02% polyvinylpyrrolidone, 0.02% Ficoll, and 0.02% bovine serum albumin), and 100 μg/ml of sonicated salmon sperm DNA. The filters were washed at 40° C. in 0.1× SSC containing 0.1% sodium dodecyl sulfate (SDS) and exposed at −70° C. to Kodak XAR film in the presence of one intensifying screen. Lambda phage hybridizing to the probes were plaque purified by successive plating and rescreening. A genomic clone hybridizing with six out of seven TM probes, designated rs5a, was isolated using this method. A 4.0 kb EcoRI fragment of rs5a was subcloned into the eukaryotic expression vector EXJ.RH modified from pcEXV-3 (73) for sequence analysis and expression studies. The nucleotide sequence of the fragment in EXJ.RH was analyzed on both strands by the Sanger dideoxy nucleotide chain-termination method (82) using Sequenase (U.S. Biochemical Corp., Cleveland, Ohio).

A second genomic clone, termed rs26a, was also isolated using the hybridization conditions described above and exhibited the same hybridization profile with TM probes. In contrast with rs5a, however, rs26a contained an internal EcoRI restriction enzyme site not present in the other clone. To further investigate potential differences between the two clones, a 3.9 kb SalI/KpnI fragment of rs26a was subcloned into the expression vector EXJ.HR for sequence analysis and expression studies. The nucleotide sequence of the fragment was analyzed on both strands by the Sanger dideoxy nucleotide chain-termination method as described above.

Cell Culture

COS-7 cells were grown on 150 mm plates in Dulbecco's Modified Eagle Medium (DMEM) with supplements (10% bovine calf serum, 4 mM glutamine, 100 units/ml penicillin/ 100 μg/ml streptomycin) at 37° C., 5% $CO_2$. Stock plates of COS-7 cells were trypsinized and split 1:6 every 3–4 days.

Human embryonic kidney cells 293 cells were grown on 150 mm plates in Dulbecco's Modified Eagle Medium (DMEM) with supplements (10% bovine calf serum, 4 mM glutamine, 100 units/ml penicillin/100 μg/ml streptomycin) at 37° C., 5% $CO_2$. Stock plates of 293 cells were trypsinized and split 1:6 every 3–4 days.

Mouse embryonic fibroblast NIH-3T3 cells were grown on 150 mm plates in Dulbecco's Modified Eagle Medium (DMEM) with supplements (10% bovine calf serum, 4 mM glutamine, 100 units/ml penicillin/100 μg/ml streptomycin) at 37° C., 5% $CO_2$. Stock plates of NIH-3T3 cells were trypsinized and split 1:15 every 3–4 days.

SK-N-Be(2) human neuroblastoma cells were grown similarly in 225 $cm^2$ flasks using 50% Eagle's Modified Essential Media, 50% Ham's Nutrient Mixture F-12, 15% fetal bovine serum, 2 mM glutamine, 100 units/ml penicillin/80 units/ml streptomycin, and 1% non-essential amino acids. Stock flasks of SK-N-Be(2) cells were trypsinized and split 1:10 every 7 days.

DNA Transfection for Pharmacological Characterization

All cloned receptor subtypes studied (human Y1, human Y2, human Y4, rat Y2a and rat Y2b) were transiently transfected into COS-7 cells by the DEAE-dextran method, using 1 μg of DNA/$10^6$ cells (17). The cDNA corresponding to the cloned Y4 receptor was disclosed in U.S. patent application Ser. No. 08/176,412 filed on Dec. 28, 1993, now U.S. Pat. No. 5,516,653.

Membrane Preparation

Membranes were harvested from COS-7 cells 48 hours after transfection and from SK-N-Be(2) seven days after splitting. Adherent cells were washed twice in ice-cold phosphate buffered saline (138 mM NaCl, 8.1 mM $Na_2HPO_4$, 2.5 mM KCl, 1.2 mM $KH2PO_4$, 0.9 mM $CaCl_2$, 0.5 mM $MgCl_2$, pH 7.4) and lysed by sonication in ice-cold hypotonic buffer (20 mM Tris-HCl, 5 mM EDTA, pH 7.7). Large particles and debris were cleared by low speed centrifugation (200×g, 20 min, 4° C.). Membranes were collected from the supernatant fraction by high speed centrifugation (32,000×g, 18 min, 4° C.), washed with ice-cold hypotonic buffer, and collected again by high speed centrifugation (32,000×g, 18 min, 4° C.). The final membrane pellet was resuspended by sonication into a small volume (~500 μl) of ice-cold binding buffer (10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (19) using Bio-Rad Reagent, with bovine serum albumin as a standard.

Radioligand Binding to Membrane Suspensions

Membrane suspensions were diluted in binding buffer supplemented with 0.1% bovine serum albumin and 0.1% bacitracin to yield membrane protein concentrations of ~0.02 mg/ml for human Y1 receptors, ~0.003 mg/ml for CG-13 receptors, and ~0.25 mg/ml for SK-N-Be(2) (under these assay conditions, non-specific binding of $^{125}$I-PYY to membranes was less than 10%). $^{125}$I-PYY and non-labeled peptide competitors were also diluted to desired concentrations in supplemented binding buffer. Individual samples were then prepared in 96-well polypropylene microliter plates by mixing membrane suspensions (200 ul), $^{125}$I-PYY (25 ul), and non-labeled peptides or supplemented binding buffer (25 ul). Samples were incubated in a 30° C. water bath with constant shaking for 120 min. Incubations were terminated by filtration over Whatman GF/C filters (pre-coated with 0.5% polyethyleneimine and air-dried before use). Filter-trapped membranes were counted for $^{125}$I in a gamma counter. Non-specific binding was defined by 100 nM human NPY. Specific binding in time course and competition studies was typically 80%; most non-specific binding was associated with the filter. Binding data were analyzed using nonlinear regression and statistical techniques available in the GraphPAD InPlot package (San Diego, Calif.).

Creation of a Stably Expressing Cell Line pcEXV-hY2 DNA was transfected into the 293 human embryonic kidney cell line by the calcium phosphate transfection method. The 293 cells were grown in minimal essential medium (MEM) with Hank's salts, plus 2 mM glutamine, 100 international units of penicillin, streptomycin at 100 ug/ml, and 10% fetal calf serum, in 5% $CO_2$ at 37° C. Stably transfected cells were selected for two weeks in media containing G-148 (1 mg/ml) and screened for the ability to bind $^{125}$I-PYY. Several clones were selected based on preliminary measurements of cell density. One positive clone, designated 293-hY2-10, was chosen for further characterization in binding and functional assays. This clone displayed saturable binding of $^{125}$I-porcine PYY in membrane preparations: $B_{max}$=880 fmol/mg membrane protein, $K_d$=3 pM, (n=3). When incubated with various concentrations of human PYY, it elicited a concentration-dependent inhibition of forskolin-stimulated cAMP accumulation as determined by radioimmunoassay. Clone 293-hY2-10 also elicited a concentration-dependent increase in free intracellular calcium as determined by Fura-2 florescence. The calcium response, which probably reflects mobilization of intracellular calcium stores, was inhibited by pretreatment of cells with pertussis toxin. $EC_{50}$ values for both the cAMP and the calcium response are currently under investigation. pcEXV-hY2 DNA was also transfected into the mouse embryonic NIH-3T3 cell line using the methods described above to create another cell line stably expressing human Y2 receptors. A clone designated N-hY2-5 was selected and characterized as above.

Tissue Localization and Gene Expression: Reverse Transcriptase PCR

Human tissues obtained from National Disease Research Interchange were homogenized and total RNA extracted using guanidine isothiocyanate/CsCl cushion method. RNA was treated with DNase to remove any contaminating genomic DNA. cDNA was prepared from total RNA with random hexanucleotide primers using the reverse transcriptase Superscript II (BRL, Gaithersburg, Md.). An aliquot of the first strand cDNA (250 ng of total RNA) was amplified in a 50 μl PCR reaction mixture (200 μM dNTPs final concentration) containing 1.2 U of Taq polymerase in the buffer supplied by the manufacturer (Perkin-Elmer Corporation), and 1 μM of primers, using a program consisting of 30 cycles of 94° C./2', 68° C./2', and 72° C./3', with a pre- and post-incubation of 95° C./5' and 72° C./10', respectively. PCR primers for human Y2 were designed against the human Y2 sequence in the third intracellular loop and carboxyl terminal regions: 5'-GGGAGTATTCGCTGATTGAGATCAT-3' (SEQ. I.D. No. 21) and 5'-GCCTTGAATGTCACGGACACCTC-3' (SEQ. I.D. No. 22), respectively.

The PCR products were run on a 1.5% agarose gel and transferred to charged nylon membranes (Zetaprobe GT, BioRad), and analyzed as Southern blots. Hybridization probes corresponding to the receptor region flanked by PCR primers were prepared (5'-CTGGGTA GT-GGTCATTTGCAGCTCCAGGACTGACATGGTTCTT-3') (SEQ. I.D. No. 23) and pre-screened for the absence of cross-reactivity with human Y1 and Y4 receptor subtypes.

Filters were hybridized with the phosphorylated probes and washed under high stringency. Labeled PCR products were visualized on X-ray film. Similar PCR and Southern blot analyses were conducted with primers and probe directed to the housekeeping gene, glyceraldehyde-3-phosphate dehydrogenase (Clontech, Palo Alto, Calif.), and demonstrated that equal amounts of cDNA from the different tissues were being assayed for Y2 receptor expression.

Localization of NPY Y2 Messenger RNA in the Rat Central Nervous System

The distribution of NPY Y2 mRNA in the rat brain was determined using in situ hybridization histochemistry. Male Sprague-Dawley rats were euthanized with $CO_2$, decapitated and the brains rapidly removed and frozen in isopentane. Coronal sections were cut at 11 μm on a cryostat and thaw-mounted onto poly-L-lysine coated slides and stored at −80° C. until use. Prior to hybridization, tissues were fixed in 4% paraformaldehyde, treated with 5 mM dithiothreitol, acetylated in 0.1 M triethanolamine containing 0.25% acetic anhydride, delipidated with chloroform, and dehydrated in graded ethanols.

The oligonucleotide probes employed to characterize the distribution of the NPY Y2 mRNA were synthesized using a Cyclone Plus DNA synthesizer (Milligen/Biosearch) and gel-purified. The probes used and their sequences are given in Table 7. Probe specificity was established by performing the in situ hybridization protocol described below on cells transfected with the rat NPY Y2 DNA (supra), or on non-transfected control cells. In addition, both sense and anti-sense probes were employed on cells and rat tissues.

Probes were 3'-end labeled with $^{35}$S-dATP (1200 Ci/mmol, New England Nuclear, Boston, Mass.) to a specific activity of $10^9$ dpm/μg using terminal deoxynucleotidyl transferase (Boehringer Mannheim; Indianapolis, Ind.). The radiolabeled probes were purified on Biospin 6 chromatography columns (Bio-Rad; Richmond, Calif.), and diluted in hybridization buffer to a concentration of $1.5 \times 10^4$ cpm/μl. The hybridization buffer consisted of 50% formamide, 4× sodium citrate buffer (1× SSC=0.15 M NaCl and 0.015 M sodium citrate), 1× Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate. One hundred μl of the diluted probe was applied to each section, which was then covered with a Parafilm coverslip. Hybridization was carried out overnight in humid chambers at 40 to 55° C. The following day the sections were washed in two changes of 2× SSC for one hour at room temperature, in 0.1× SSC for 30 min at 50–60° C., and finally in 0.1× SSC for 30 min at room temperature. Tissues were dehydrated in graded ethanols and apposed to Kodak XAR-5 film for 3 days to 6 weeks at −20° C., then dipped in Kodak NTB3 autoradiography emulsion diluted 1:1 with 0.2% glycerol water. After exposure at 4° C. for 2 to 8 weeks, the slides were developed in Kodak D-19 developer, fixed, and counterstained with hematoxylin and eosin.

Functional Assay: Radioimmunoassay of cAMP

Stably transfected cells were seeded into 96-well microliter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1% bovine serum albumin plus 5 mM theophylline and pre-equilibrated in the same solution for 20 min at 37° C. in 5% $CO_2$. Cells were then incubated 5 min with 10 μM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microliter plate (Millipore, Bedford, Mass.). Filters were punched and counted for $^{125}$I in a Packard gamma counter. Binding data were analyzed using nonlinear regression and statistical techniques available in the GraphPAD Prism package (San Diego, Calif.).

Functional Assay: Intracellular Calcium Mobilization

The intracellular free calcium concentration was measured by microspectroflourometry using the fluorescent indicator dye Fura-2/AM. Stably transfected cells were seeded onto a 35 mm culture dish containing a glass coverslip insert. Cells were washed with HBS and then loaded with 100 μl of Fura-2/AM (10 μM) for 20 to 40 min. After washing with HBS to remove the Fura-2/AM solution, cells were equilibrated in HBS for 10 to 20 min. Cells were then visualized under the 40× objective of a Leitz Fluovert FS microscope and fluorescence emission was determined at 510 nM with excitation wave lengths alternating between 340 nM and 380 nM. Raw fluorescence data were converted to calcium concentrations using standard calcium concentration curves and software analysis techniques.

Reagents

Cell culture media and supplements were from Specialty Media (Lavallette, N.J.). Cell culture plates (150 mm) were from Corning (Corning, N.Y.). Cell culture flasks (225 $cm^2$) and polypropylene microliter plates were from Co-star (Cambridge, Mass.). Porcine $^{125}$I-PYY was from New England Nuclear (Boston, Mass.). NPY and related peptide analogs were from either Bachem California (Torrance, Calif.) or Peninsula (Belmont, Calif.). Whatman GF/C filters were Brandel (Gaithersburg, Md.). Bio-Rad Reagent was from Bio-Rad (Hercules, Calif.). Bovine serum albumin and bacitracin were from Sigma (St. Louis. Mo.). All other materials were reagent grade.

RESULTS

Isolation of a cDNA Clone Encoding a Human Hippocampal Y2 Receptor

In order to clone a human NPY receptor subtype (Y2), we used an expression cloning strategy in COS-7 cells (20, 21, 22). This strategy was chosen for its extreme sensitivity since it allows detection of a single "receptor positive" cell by direct microscopic autoradiography.

Since the Y2 receptor is described as a presynaptic receptor, it is difficult to locate cell bodies that actually contain this specific mRNA in restricted brain areas. We reasoned that human hippocampus was a good source of mRNA since it contains both a large number of interneurons and has been shown to carry a particularly dense population of Y2 receptors (23, 24, 25, 26). A human hippocampal cDNA library of 2.2×10⁶ independent recombinants with a 3 kb average insert size was fractionated into 440 pools of ≈5000 independent clones. From the first 200 pools tested, three gave rise to positive cells in the screening assay (#145, 158 and 189). The last 220 pools tested were all negative.

Since both Y1 and Y2 receptor subtypes are expressed in the hippocampus (2), we analyzed the DNA of positive pools by PCR with Y1 specific primers. Pools #145 and #158 turned out to contain cDNAs encoding an Y1 receptor, but pool #189, negative by PCR (data not shown), likely contained a cDNA encoding a human hippocampal NPY receptor that was not Y1. Pool #189 was subdivided in 20 pools of 1000 clones each, and a preliminary pharmacological characterization was run on COS-7 cells transfected with DNA prepared from the secondary pools. This preliminary analysis revealed that a 100 fold excess of cold [Leu$^{31}$-Pro$^{34}$]NPY totally inhibited binding of $^{125}$I-PYY to control COS-7 cells transfected with the Y1 gene. In contrast, no significant inhibition of binding was observed when the same experiment was performed on COS-7 cells transfected with secondary pool #189-17 (data not shown). This is consistent with pool #189 containing a cDNA encoding a human hippocampal Y2 receptor. The sib selection was therefore pursued on pool #189 until a single clone was isolated (designated CG-13).

The isolated clone carries a 4.2 kb cDNA. This cDNA contains an open reading frame between nucleotides 1002 and 2147 that encodes a 381 amino acid protein (SEQ. I.D. No. 2). The unusually long 5' untranslated region could be involved in the regulation of translation efficiency or mRNA stability. The flanking sequence around the putative initiation codon conforms to the Kozak consensus sequence for optimal translation initiation (27, 28).

The hydrophobicity plot displayed seven hydrophobic, putative membrane spanning regions which makes the human hippocampal Y2 receptor a member of the G-protein coupled superfamily. The nucleotide and deduced amino acid sequences are shown in FIG. 1 and FIG. 2, respectively.

Like most G-protein coupled receptors, the Y2 receptor contains a consensus sequence for N-linked glycosylation, in the amino terminus (position 11) involved in the proper expression of membrane proteins (29). The Y2 receptor carries two highly conserved cysteine residues in the first two extracellular loops that are believed to form a disulfide bond stabilizing the functional protein structure (30). The Y2 receptor shows 7 potential phosphorylation sites for protein kinase C in positions 11, 27, 64, 145, 188, 250 and 340, 2 casein kinase sites in positions 174 and 358, and 2 cAMP- and cGMP-dependent protein kinase phosphorylation sites in positions 146 and 350. It should be noted that 7 of those 11 potential phosphorylation sites are located in intra-cellular loops 1, 2 and 3 as well as in the carboxyl terminus of the receptor and therefore could play a role in regulating functional characteristics of the Y2 receptor (30). A potential palmitoylation site is present in the sequence at the cysteine found in position 326. A large number of G-protein coupled receptors carry a cysteine in the same position and O'Dowd et al. have speculated that it plays an important role in the functional coupling of the human $\beta_2$-adrenergic receptor (31). The formation of this additional cytosolic loop may influence the mobility of the receptor across the membrane (32).

When compared to the published human Y1 cDNA clone (10, 11) the Y2 sequence shows surprisingly low homology both at the nucleotide level, 48.1% (FIG. 3) and overall amino acid level, 31% (FIG. 4). The transmembrane domain identity of the human hippocampal Y2 receptor with other 7 TM receptors is shown in Table 1. The low TM identity with other G-protein coupled receptor families, with other peptide receptors and especially with the Y1 subtype raises the possibility that Y2 receptor subtypes belong to a new distinct sub-family of 7 TM peptide receptors. Conversely, NPY receptor subtypes could form a sub-family where members show unusually low levels of overall homology. Applicants have also cloned the human Y4 receptor, and this receptor also exhibits a low degree of homology with the human Y2 receptor (Table 1). It is interesting to observe that the mouse orphan receptor MUSGIR (mouse glucocorticoid induced receptor, 33) shows the highest TM identity (42%, Table 1) with our human Y2 receptor. The same comparison between human Y1 (or Y4) and Y2 TM regions only gives a score of 41% identity. If we were comparing the human Y2 receptor sequence with the human homolog of the MUSGIR receptor, the level of identity might even be higher. Therefore the MUSGIR receptor could be related to the NPY receptors and bind members of the pancreatic polypeptide ligand family. A full pharmacological evaluation of the human GIR homolog with NPY, PYY and PP related ligands is now underway to verify this hypothesis.

Using the human Y2 probe, northern hybridizations reveal a unique band at 4.3 kb in human brain after a three-day exposure (FIG. 16). This is in good agreement with the 4.2 kb cDNA that we isolated by expression cloning and indicates that our cDNA clone is full-length. The mRNA encoding the human Y2 receptor is present in significant amounts in amygdala, corpus callosum, hippocampus, and subthalamic nucleus. A faint band is detectable in caudate nucleus, hypothalamus and substantia nigra. No signal could be detected in thalamus. It should be noted that Clontech's MTN blot does not carry any mRNA from cortex or brain stem.

Southern hybridizations to human genomic DNA followed by high stringency washes (FIG. 17) suggest that the human genome contains a single Y2 receptor gene (single band with EcoRI, HindIII, BamHI and PstI). The faint bands at 9 and 12 kb observed with BglII can be explained by the presence of two BglII restriction sites in the coding region of the human Y2 sequence and are also consistent with a single Y2 receptor gene.

Pharmacology of the Transiently Expressed Human Y2 Receptor

The Y2-like pharmacology of CG-13, originally identified by whole cell autoradiographic techniques, was further defined by membrane binding assays. The gene for the human hippocampal Y2 receptor was transiently expressed in COS-7 cells for full pharmacological evaluation. $^{125}$I-PYY bound specifically to membranes from COS-7 cells transiently transfected with the CG-13 construct. The time course of specific binding was measured in the presence of 0.06 nM $^{125}$I-PYY (FIG. 5). The association curve was biphasic, with approximately 55% of the specific binding occurring during an initial rapid phase and 45% following a slower time course. For the rapid phase, the observed association constant ($K_{obs}$) was 1.28±0.02 min$^{-1}$ and $t_{1/2}$ was 0.5 min; equilibrium binding was 95% complete within 2 min and 100% complete within 5 min (n=3). For the slow phase, $K_{obs}$ was 0.02±0.00 min$^{-1}$ and $t_{1/2}$ was 37 min; equilibrium binding was 90% complete within 120 min, 95% complete within 160 min and 100% complete within 280 min (n=3). Total equilibrium binding, composed of both phases, was 95% complete within 120 min and 100% complete within 240 min. The biphasic association curve may reflect a complex pattern of receptor surface binding followed by access to deep-seated binding sites, as has been suggested by Schwartz and co-workers for Y2 receptors (34). For comparison, we also measured the time course of binding to human Y1 receptors transiently expressed in COS-7 cells (FIG. 5). The association curve was monophasic, with a $K_{obs}$ of 0.06±0.02 min$^{-1}$ and a $t_{1/2}$ of 12 min; equilibrium binding was 95% complete within 51 min and 100% complete within 90 min (n=3). The different patterns of association for CG-13 and human Y1 receptors suggest novel mechanisms of receptor/ligand interaction.

Saturation binding data for $^{125}$I-PYY were fit to a one-site model with an apparent $K_d$ of 0.069±0.009 nM and an apparent $B_{max}$ of 7.8±0.4 pmol/mg membrane protein, corresponding to approximately 7.5×10$^5$ receptors/cell (n=3; FIG. 6). Given that the transfection efficiency was 20–30% (data not shown), the receptor density on transfected cells was probably closer to 3×10$^6$/cell. Membranes from mock-transfected cells, when prepared and analyzed in the same way as those from CG-13-transfected cells, displayed no specific binding of $^{125}$I-PYY. We conclude that the $^{125}$I-PYY binding sites observed under the described conditions were derived from the CG-13 construct.

Y2 receptor recognition is thought to depend primarily upon the four C-terminal residues of NPY (Arg$^{33}$-Gln$^{34}$-Arg$^{35}$-Tyr$^{36}$-NH$_2$) preceded by an amphipathic α-helix (M4, M5); exchange of Gln$^{34}$ with Pro$^{34}$ is not well tolerated (4, 5). We therefore chose several C-terminal fragments and C-terminal modified peptides for competition binding studies. The rank order of affinity for selected compounds was derived from competitive displacement of $^{125}$I-PYY (FIG. 7 and Table 3). The CG-13 receptor was compared with two model systems: 1) the cloned human Y1 receptor (10, 11) transiently expressed in COS-7 cells, and 2) the Y2-like receptor population expressed by human SK-N-Be(2) neuroblastoma cells (2, 8). To our knowledge, no models for human Y3 and human PP receptors have been described.

CG-13 bound with high affinity to human NPY ($K_i$=0.69 nM) and even more so to human PYY ($K_i$=0.39 nM). The $K_i$ values are in agreement with numerous reports of pharmacologically defined Y2 receptors studied in NPY binding and functional assays (2). The opposite rank order was observed with human Y1 receptors, combined with stronger receptor/binding interactions ($K_i$=0.049 and 0.085 nM for human NPY and human PYY, respectively). It is interesting in this regard that CG-13 bound $^{125}$I-PYY ($K_d$=0.069 nM) with higher affinity than PYY ($K_i$=0.39 nM), suggesting that iodination may stabilize the receptor/ligand complex. The human Y1 receptor, in contrast, bound both $^{125}$I-PYY ($K_d$=0.062+0.010 nM, n=3, data not shown) and PYY ($K_i$=0.085 nM) with comparable affinity. The fact that CG-13 and the human Y1 receptor bound NPY, PYY and $^{125}$I-PYY with different magnitudes and rank orders of affinity most likely reflects distinct mechanisms of peptide recognition which could potentially be exploited for the development of subtype-selective non-peptide ligands.

CG-13 also bound with high affinity to porcine NPY ($K_i$=0.86 nM), which differs from human NPY by containing Leu$^{17}$ in the PP-fold rather than Met$^{17}$. CG-13 was relatively insensitive to N-terminal deletion of NPY and PYY; the affinity for porcine NPY$_{22-36}$ was only 5-fold less than that for full length porcine NPY. Extreme deletion of α-helical structure was less well tolerated; the affinity for porcine NPY$_{26-36}$ was 240-fold less than that for full length porcine NPY. Human [Leu$^{31}$,Pro$^{34}$]NPY and human PP, both having Pro$^{34}$ rather than Glu$^{34}$, did not bind well ($K_i$>300 nM). Hydrolysis of the carboxyl terminal amide to free carboxylic acid, as in NPY free acid, also disrupted binding affinity for CG-13 ($K_i$>300 nM). The terminal amide appears to be a common structural requirement for pancreatic polypeptide family/receptor interactions.

The competitive displacement data indicate that CG-13 binds PYY with equal or greater affinity than NPY. The C-terminal region of NPY is the primary pharmacophore. CG-13 does not tolerate exchange of Gln$^{34}$ with Pro$^{34}$, as revealed by low affinity interactions with human [Leu$^{31}$, Pro$^{34}$]NPY and human PP. The binding profile, which is shared by SK-N-Be(2) cell receptors but not by human Y1 receptors, is characteristic of the pharmacologically defined Y2 receptor (refs. 2, 8; see also Table 2). The membrane binding studies therefore confirm and extend our assessment that CG-13 encodes a human Y2 receptor.

The pharmacological profile of the human Y2 receptor was further investigated using peptide analogs related to NPY, PYY, and PP (Table 4). CG-13 did not discriminate human and frog analogs of NPY ($K_i$=0.74 and 0.87 nM, respectively), human and porcine analogs of NPY$_{2-36}$ ($K_i$= 2.0 and 1.2 nM, respectively), human and porcine analogs of [Leu$^{31}$,Pro$^{34}$]NPY ($K_i$>130 and>540 nM, respectively), or human NPY and human [Tyr-o-Me$^{21}$]NPY ($K_i$=0.74 and 1.6 nM, respectively). This last derivative was tested based on the proposal that it was selective for central vs. peripheral NPY receptors, with high binding affinity in rat CNS but low potency in rat vas deferens relative to NPY (83). For the receptors under investigation, however, [Tyr-O-Me$^{21}$]NPY and human NPY yielded highly similar binding profiles. The NPY derivative with greatest selectivity for CG-13 was C2-NPY, a $C^2$ to $C^{27}$ disulfide-stabilized derivative of NPY with an 8-amino-octanoic linker replacing NPY$_{5-24}$ ($K_i$=3.5 nM, $\geq$20-fold selective for CG-13 over Y1 and Y4 receptors). C2-NPY has been described as a Y2-selective compound (3).

Three additional PYY derivatives yielded distinctive binding profiles. CG-13 bound with highest affinity and greatest selectivity to human PYY3-36 ($K_i$=0.70 nM, $\geq$20-fold selective for CG-13 over Y1 and Y4 receptors). PYY$_{3-36}$ is a major form of PYY-like immunoreactivity in blood and could therefore mediate CG-13-dependent processes in vivo (84, 85). Porcine PYY was relatively nonselective and similar in binding affinity to human PYY ($K_i$=0.35 nM and 0.36 nM, respectively). Human [Pro$^{34}$]PYY was lacking in binding affinity for CG-13 ($K_i$>310), further supporting the argument that Pro$^{34}$ is disruptive for high affinity peptide binding to the CG-13 receptor.

Six additional PP derivatives were investigated. Those peptides which resemble human PP in that they contain Pro$^{34}$ (bovine, rat, avian, and frog PP) displayed no activity in the CG-13 binding assay. High affinity binding was detected only for salmon PP ($K_i$=0.17 nM), which is distinguished by containing Gln$^{34}$. When the C-terminus of human PP was modified to more closely resemble human NPY, as in [Ile$^{31}$, Gln$^{34}$]PP, the binding affinity for CG-13 was increased dramatically ($K_i$=20 nM). It has been reported previously that [Ile$^{31}$, Gln$^{34}$]PP was more active than PP in Y2 binding assays, while exhibiting decreased potency for putative PP receptors in rat vas deferens (86).

Several proposed NPY antagonists were analyzed for their ability to bind to CG-13 receptors. These include PYX-1 and PYX-2, C-terminal derivatives of NPY reported to antagonize NPY-mediated feeding and neurotransmitter release (87, 88, 89). Neither synthetic peptide bound to CG-13 with high affinity or selectivity ($K_i$=684 for PYX-1 and $K_i$>1000 nM for PYX-2). [D-Trp$^{32}$]NPY is an NPY derivative reported to regulate feeding behavior when injected into the hypothalamus of rats (90); this analog was inactive in the CG-13 binding assay. Another inactive compound was NPY$_{1-24}$ amide, a peptide reported to antagonize NPY in the rat vas deferens (83).

Human Tissue Y2 Receptor Macrolocalization: PCR

Human Y2 mRNA was detected by PCR techniques in a broad range of human tissues (Table 5). Relatively intense hybridization signals were detected in total brain, thoracic artery, coronary artery, and penis, with more moderate levels in frontal brain, ventricle, mesentery, stomach and ileum. Relatively low levels were detected in nasal mucosa and pancreas. Several other tissues were negative for Y2 mRNA as measured by this technique, including atrium, liver, and uterus.

Cloning and Expression of Two Isoforms of the Rat NPY/PYY (Y2) Receptor

Two rat genomic clones homologous to the human Y2 receptor were isolated, termed rs5a (FIG. 8) and rs26a (FIG. 9). The nucleotide sequence of rs5a is 86.5% identical in the coding region to that of the human Y2 receptor (FIG. 10), and can encode a 381 amino acid protein with 94.5% identity to the human Y2 amino acid sequence (FIG. 11). In the putative transmembrane domains (TMs), the protein predicted by rs5a exhibits 98.2% amino acid identity with the human Y2 receptor (FIG. 11). This high degree of primary sequence identity is often observed for species homologues, and strongly suggests that the receptor encoded by rs5a is the rat Y2 receptor. However, even a single amino acid substitution can influence the functional properties of a receptor; thus, even species homologues exhibiting a high level of sequence identity may display different pharmacological properties (infra), underscoring the importance of obtaining both rat and human receptors for use in drug development.

Sequence analysis of the second genomic clone revealed that rs26a also encoded a full-length rat Y2 receptor; however, rs26a contains two nucleotide changes when compared with the sequence of rs5a. Both nucleotide changes result in amino acid substitutions in the predicted rat Y2 receptor protein. With two (2) amino acid changes, the protein encoded by rs26a is 99.7% identical to that of rs5a. Compared with the human Y2 receptor, the nucleotide sequence identity of rs26a is 85.2% and the amino acid sequence identity is 98.2%. This clone therefore encodes an isoform of the rat Y2 receptor distinct from that encoded by rs5a. The locations of the amino acid substitutions (N-terminus and 5/6 loop; see FIG. 3) suggest that they could potentially influence receptor function. The Y2 receptors encoded by rs5a and rs26a are likely to represent allelic variants at the same gene locus; however, rs26a could represent a second rat Y2 gene. Accordingly, we have designated the isoform encoded by rs5a as the rat Y2a receptor, and designated the isoform encoded by rs26a as the rat Y2b receptor.

The primary sequences of rat and human Y2 receptors, while highly related, show distinct patterns of sequence motifs for N-linked glycosylation, N-myristoylation, and protein phosphorylation. For example, the rat Y2a differs from the rat Y2b in that it contains an additional site for phosphorylation by protein kinase C. Further, the human Y2 differs from both rat Y2 isoforms in containing two additional sites for N-linked glycosylation, two additional sites for cAMP- and cGMP-dependent protein phosphorylation, an additional site for casein kinase II phosphorylation, one additional site for protein kinase C phosphorylation, and two fewer sites for N-myristoylation. These sites could mediate differences in the function or regulation of the three receptors. The isolation of two rat homologues of the Y2 receptor provides the means to compare the pharmacological properties of the rat and human Y2 receptors (see below) in relation to their observed differences in primary structures. These data will be critical to the design and testing of human therapeutic agents acting at these sites.

Binding Studies with Rat Y2 Homologs

The DNA corresponding to the rat Y2a homolog was transiently expressed in COS-7 cells for membrane binding studies. The binding of $^{125}$I-PYY to the rat Y2a receptor was saturable over a radioligand concentration of 0.5 pM to 2.5 nM. Binding data were fit to a one-site model with an apparent $K_d$=0.26 nM and a receptor density of 5100 fmol/mg membrane protein. As determined by using peptide analogs within the pancreatic polypeptide family, the rat Y2a pharmacological profile resembles that for the human Y2 receptor (Table 6). Each receptor analog is relatively tolerant of N-terminal ligand deletion (the human apparently more so than the rat) and intolerant of any peptide containing Pro$^{34}$ or a modified C-terminus (as in NPY free acid or [D-Trp$^{32}$] NPY).

The rat Y2b clone, which differs from rat Y2a by two amino acid changes one in the N-terminal tail (from Leu$^{20}$ to Phe$^{20}$) and another in the third intracellular loop (from Thr$^{266}$ to Met$^{266}$), has been subjected only to a preliminary investigation. Membranes from COS-7 cells transiently transfected with the rat Y2b receptor were incubated with 0.08 nM $^{125}$I-PYY and analyzed for specific binding after incubation at 30° C. for 120 min. Membranes from transfected cells bound 310 fmol $^{125}$I-PYY/mg membrane protein, whereas membranes from mock-transfected cells (receiving vector without receptor cDNA insert) bound only 3 fmol $^{125}$I-PYY/mg membrane protein. It remains to be determined whether there exist any pharmacological or functional differences between the ratY2a and rat Y2b receptors.

Localization of NPY Y2 Messenger RNA in the Rat Central Nervous System

In control experiments, hybridization signals for rat NPY Y2 mRNA were seen only with the antisense probes (probe sequences shown in Table 7), and only over cells which had been transfected with the rat Y2 DNA (FIG. 18). The probes were designed to recognize both rat Y2a and rat Y2b. Neither mock transfected cells nor cells transfected with rat NPY Y1 mRNA exhibited hybridization signals. On rat brain sections, no hybridization signals were obtained with the sense probes, only with the antisense probes.

The distribution of NPY Y2 mRNA observed in coronal sections through the rostrocaudal extent of rat brain is shown in FIG. 12 and Table 8. Hybridization signals were seen over many areas of the rat brain (FIG. 12), which, at the microscopic level, were confined to the cytoplasm of neuronal profiles (data not shown). In the telencephalon, the most intense hybridization signals were observed over the CA3 region of the hippocampus (FIGS. 12B–E) and over the anteroventral aspect of the medial nucleus of the amygdala (FIGS. 12C, D). Less intense signals were found over the olfactory tubercle, the lateral septal nucleus (FIG. 12A), and over the basomedial nucleus and posteromedial cortical nucleus of the amygdala (FIGS. 12D, E). Scattered neurons with hybridization signal were also seen in the central amygdaloid nucleus. In cortex, silver grains were seen over large neurons in the piriform region.

Figure 12A:
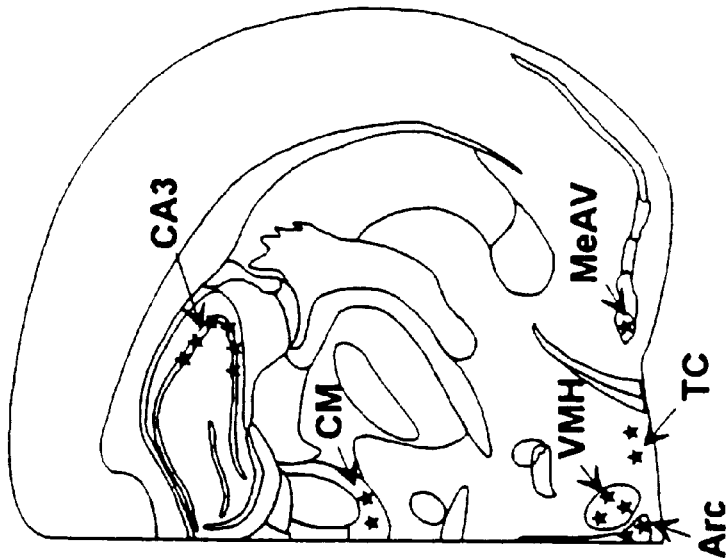
Figure 12B:
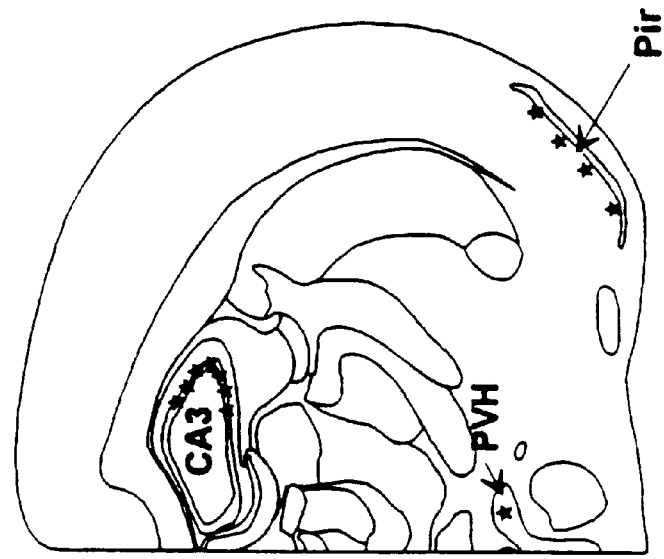
Figure 12C:
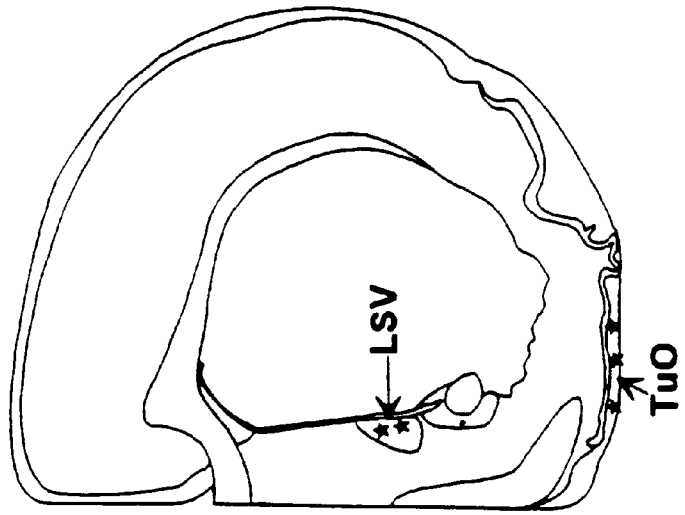
Figure 12D:
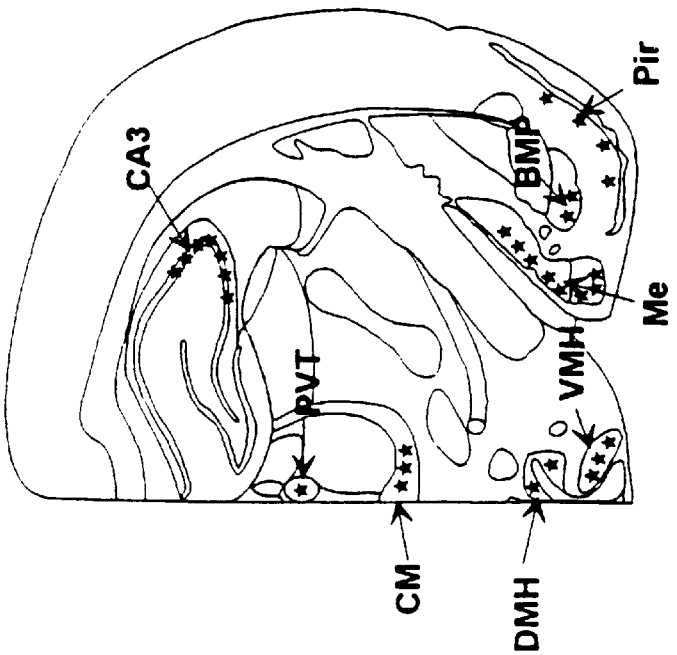
Figure 12E:
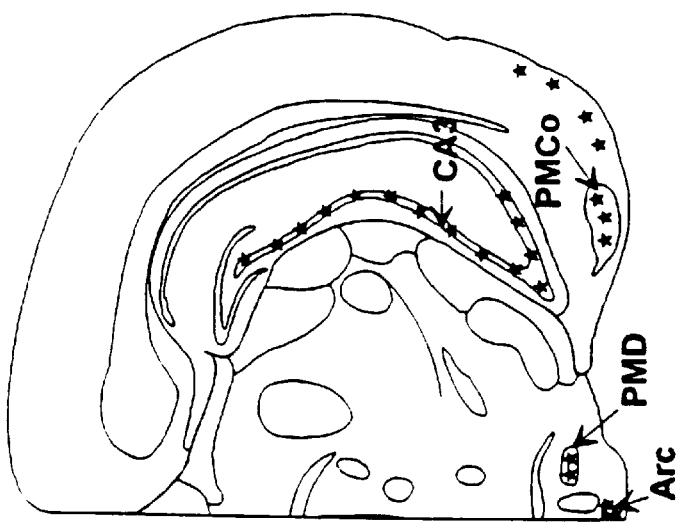
Figure 12F:
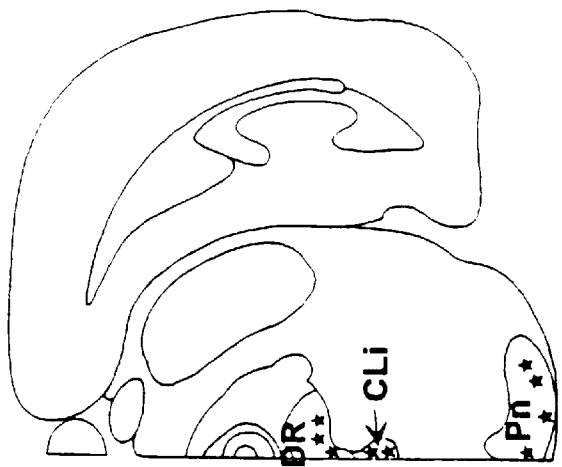

Among diencephalic structures, the arcuate nucleus of the hypothalamus exhibited the most intense hybridization signal for NPY Y2 mRNA (FIGS. 12D, E). In this area, most of the neurons appeared to be labelled, and many neurons were also labelled in the region of the tuber cinereum lateral to the arcuate nucleus. In addition, both the dorsomedial and ventromedial hypothalamic nuclei contained appreciable hybridization signals over subpopulations of neurons (FIGS. 12C, D). In the dorsal and ventral premammillary nuclei, hybridization signal was seen over many neurons (FIG. 12E). In the thalamus, neurons in the centromedial nucleus were labelled (FIGS. 12C, D), while a smaller, less intensely labelled group of cells was visible in the paraventricular nucleus (FIG. 12D).

Figure 12G:
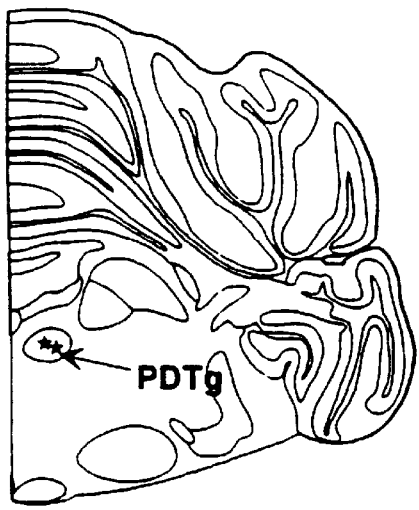
Figure 12H:
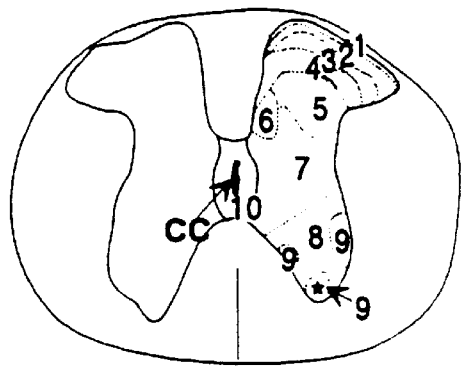

In the mesencephalon, medulla, and pons, few structures were labelled with the antisense oligonucleotide probe. Those exhibiting a moderate level of hybridization signal were the dorsal and caudal linear raphe (FIG. 12F), the pontine nucleus, and the posterior dorsal tegmental nucleus (FIG. 12G). In the spinal cord, labelling was observed over scattered large neurons in lamina 9 (FIG. 12H). Silver grains were also found over a few large neurons in the dorsal root ganglion.

Receptor/G Protein Interactions: Effects of Guanine Nucleotides

For a given G protein-coupled receptor, a portion of the receptor population in a membrane homogenate typically exists in the high affinity ligand binding state as a receptor/G protein complex. The binding of GTP or a nonhydrolyzable analog to the G protein causes a conformational change in the receptor which favors a low affinity ligand/binding state (110). We investigated whether the non-hydrolyzable GTP analog, Gpp(NH)p, would alter the binding of human NPY or $^{125}$I-PYY to Y2 receptors transiently expressed in COS-7 cells. The competition curve produced by human NPY was evaluated in the absence and presence of 100 μM Gpp(NH)p. The human Y2 receptor was relatively insensitive to the Gpp(NH)p compared to the rat Y2a receptor (FIG. 13). The $IC_{50}$ for human NPY binding to the human Y2 receptor was increased from 2.2 nM to 3.3 nM; specific binding of $^{125}$I-PYY was decreased by only 4% (n=5). The $IC_{50}$ for human NPY binding to the rat Y2a receptor was altered very little (from 0.7 nM to 1.2 nM, n=2); specific binding of $^{125}$I-PYY, however, was decreased by 23% (n=2). A similar pattern of sensitivity to Gpp(NH)p was reported for $^{125}$I-PYY binding to rat brain (91). The difference between the rat and human Y2 receptor clones could be explained by several factors, including 1) the types of G proteins available in COS-7 cells, 2) the level of receptor reserve in COS-7 cells (note that human Y2 receptor density was greater than that of the rat Y2a receptor), and 3) the efficiency of receptor/G protein coupling (92; 93).

Stable Expression Systems: Characterization in Binding Assays

Untransfected 293 and NIH-3T3 cells were pre-screened for specific $^{125}$I-PYY binding and found to be negative (data not shown). After co-transfection with the human Y2 cDNA plus a G-418-resistant gene and selection with G-418, surviving colonies were screened for specific binding of $^{125}$I-PYY. Two positive clones were identified and isolated for further study (293 clone #10 and NIH-3T3 clone #5). The binding of $^{125}$I-PYY to membranes from the 293 stable clone was saturable over a radioligand concentration range of 0.5 pM to 2.5 nM. Binding data were fit to a one-site binding model with an apparent $K_d$ of 3±1 pM and a receptor density of 880±50 fmol/mg membrane protein (mean±s.e.m., n=3). Membranes from stably transfected NIH-3T3 cells displayed similar binding properties, with an apparent $K_d$ of 8±2 pM and a receptor density of 160±60 fmol/mg membrane protein (mean±s.e.m., n=2). Membranes from both stable clones were incubated with 0.08 nM $^{125}$I-PYY in the presence or absence of 100 μM Gpp(NH)p. Specific binding of $^{125}$I-PYY to Y2 receptors in 293 cell membranes was reduced 32% in the presence of the guanine nucleotide, whereas specific binding to Y2 receptors in NIH-3T3 cell membranes was reduced only 6% under the same conditions. The data serve to emphasize that the receptor/G protein interactions for a given receptor clone can vary depending upon the resident G proteins in the host cell line (93). Additional factors such as receptor density and receptor reserve can also play a role (92).

Functional Assay: cAMP

Activation of all Y-type receptors described thus far is thought to involve coupling to G-proteins which are inhibitory for adenylate cyclase activity ($G_i$ or $G_o$) (1). Based on these prior observations, we investigated the ability of PYY to inhibit forskolin-stimulated cAMP accumulation in 293 cells stably expressing the human Y2 receptor. Incubation of intact cells with 10 $\mu$M forskolin produced a 10-fold increase in cAMP accumulation over a 5 minute period, as determined by radioimmunoassay. Simultaneous incubation with human PYY decreased the forskolin-stimulated cAMP accumulation by 71% in stably transfected 293 cells (FIG. 14) but not in untransfected cells (data not shown). The NPY-mediated response was concentration-dependent ($EC_{50}$=0.25 nM). We conclude that human Y2 receptor activation can result in decreased cAMP accumulation, very likely through inhibition of adenylate cyclase activity. Similar results were obtained for NIH-3T3 cells stably transfected with the human Y2 receptor, in which human NPY decreased forskolin-stimulated cAMP accumulation by 50% in transfected cells with an $EC_{50}$ of 0.21 nM (FIG. 14).

Peptides selected for their ability to bind to the transiently expressed human Y2 receptor were further investigated for functional activity using stably transfected 293 cells (Table 9). All peptides with measurable binding affinity were able to mimic the effects of PYY on cAMP accumulation. $EC_{50}$ values were generally within a 10-fold range of $K_i$ values, often lower in magnitude (Table 9). We also investigated the functional activity of the reported feeding behavior modulator [D-Trp$^{32}$]NPY. Consistent with this peptide's low binding affinity for the human Y2 receptor, we detected no functional activity at concentrations up to 0.3 $\mu$M, or when tested at 0.3 $\mu$M for antagonism of the functional response (data not shown). The reported NPY receptor antagonists PYX-1 and PYX-2 were also inactive when tested under the same paradigm.

Functional Assay: Intracellular Calcium Mobilization

The intracellular free calcium concentration was increased in 293 cells stably transfected with the human Y2 receptor after application of 1 $\mu$M human PYY ($\Delta[Ca^{2+}]_i$=80 nM; FIG. 15). The PYY-mediated response was concentration-dependent, with $EC_{50}$=39 nM, n=2 (FIG. 15). PYY-induced calcium mobilization was relatively maintained in the presence of 1 mM extracellular EGTA ($\Delta[Ca^{2+}]_i$=64 nM for 1 $\mu$M human PYY), suggesting that intracellular calcium stores are the primary source of the transient calcium flux. Pretreatment with pertussis toxin (100 ng/ml for 24 hours) decreased the response to 300 nM human PYY by 93%, thereby supporting a G protein-linked signal transduction pathway. Untransfected 293 cells did not respond to human PYY (data not shown). The calcium mobilization assay provides a second pathway through which Y2 receptor activation can be measured.

DISCUSSION

Attempts to isolate the NPY Y2 receptor subtype based on sequence homology with the Y1 receptor have not been successful so far. Therefore, we chose an expression cloning approach where a functional receptor is actually detected with exquisite sensitivity on the surface of transfected cells, using a highly specific iodinated ligand. Using this strategy, we have identified a human cDNA encoding the pharmacologically defined Y2 receptor. The fact that we had to screen 2.2x10$^6$ independent clones with a 3 kb average insert size to find one clone reveals either a very strong bias against Y2 cDNA cloning in the cDNA library construction procedure, or the Y2 mRNA is expressed at very low levels in human hippocampal tissue. The longest reading frame in the cDNA encodes a 381 amino acid protein with an estimated molecular weight of 42 kD. Given the fact that there is an N-linked glycosylation site in the amino terminus, the apparent molecular weight could be slightly higher and in good agreement with published data on the molecular weight of the human hippocampal Y2 receptor at 50 kD (36). The Y2 receptor carries a large number of potential phosphorylation sites which could be involved in the regulation of its functional characteristics. The nucleotide and amino acid sequence analysis both reveal low identity levels with all 7-TM receptors including the human Y1 and Y4 receptors. The highest transmembrane amino acid identity is found with the mouse MUSGIR receptor. A pharmacological profile on the human GIR homolog will be established with NPY, PYY and pancreatic polypeptide related ligands to find out if this orphan receptor belongs to the same pharmacologically defined neuropeptide Y receptor sub-family. The human Y2 receptor shares very low amino acid identity with the previously cloned human Y1 receptor (31% overall and 41% in transmembrane regions). The human Y2 receptor also displays a unique pharmacological profile and a unique time course of association with $^{125}$I-PYY. The dramatic differences in sequence and pharmacological profile between the human Y1 and Y2 receptors suggest that they might be encoded by two unrelated genes whose products have evolved into binding the same family of ligands. Conversely, they could have diverged from a common ancestor very early in evolution and undergone multiple mutations leading to distinct pharmacological characteristics.

Northern analysis reveals a 4.3 kb band in human brain and demonstrates that our 4.2 kb Y2 cDNA is full-length. Southern analyses are consistent with the human genome containing a single Y2 receptor gene.

The pharmacological binding profile established in our initial characterization served primarily to establish the CG-13 as a human Y2 receptor. The additional data included here reflect an increased understanding of receptor ligand/interactions. We now know, for example, that C2-NPY and PYY$_{3-36}$ can be used to compete for Y2 receptor sites with greater affinity and selectivity than the C-terminal fragments of NPY originally described. We also know that certain peptides which are thought to antagonize NPY-dependent effects, such as [D-Trp$^{32}$]NPY, PYX-1, and PYX-2, are unable to compete for binding of the human Y2 receptor clone described here. Our evidence does not therefore support the cloned Y2 receptor as the molecular target of these particular peptides in vivo or in vitro.

Human Y2 receptor mRNA was detected by PCR techniques in a broad range of human tissues (Table 5). Relatively intense hybridization signals were detected in total brain, thoracic artery, coronary artery, and penis, with more moderate levels in frontal brain, ventricle, and mesentery. This distribution is consistent with evidence for Y2 receptor localization and receptor-dependent effects in CNS, cardiovascular, and reproductive physiology (94). Moderate hybridization signals were also detected in stomach and ileum, consistent with evidence for Y2-mediated effects on chief cell cAMP accumulation (95) and also intestinal electrolyte flux (61; 96). Relatively low levels were detected in nasal mucosa and pancreas, two tissues in which Y2-like receptors have been reported to regulate vasoconstriction and pancreatic secretion, respectively (97, 98, 99). A more definitive localization of the Y2 receptor mRNA and receptor expression (i.e., whether on neurons, enterocytes, vascular smooth muscle cells, etc.) is attainable through in situ hybridization and receptor autoradiography techniques.

The distribution of NPY Y2 mRNA described here in rat brain has a number of potential implications, and raises a number of important questions. Among these are; 1) how does the distribution of this mRNA correlate with that of NPY itself; 2) how does the Y2 mRNA distribution relate to the putative autoradiographic localization of Y2 receptors described by previous investigators; and 3) what are the functional implications of the Y2 mRNA distribution?

Correlation with NPY Immunoreactivity

Neuropeptide Y is one of the most abundant and widely distributed peptides in the mammalian brain (100). In some areas, NPY Y2 mRNA appears to be co-distributed with NPY-immunoreactive (NPYir) neurons, although colocalization in the same neuron(s) remains to be established. In both the arcuate nucleus of the hypothalamus and the medial nucleus of the amygdala, the distribution of Y2 mRNA overlaps with the distribution of NPYir neurons demonstrated by immunocytochemical studies (100, 101). In addition, both areas contain moderate plexuses of NPYir axons. These observations leave open the question of presynaptic/postsynaptic nature of the Y2 receptor. In most other areas of the brain, the Y2 mRNA does not appear to be co-distributed with NPYir neurons, but instead correlates better with the distribution of NPYir terminal fields, suggesting a postsynaptic localization.

Comparison with Receptor Autoradiography

A number of investigators have described the distribution of NPY receptors based on the autoradiographic localization of radiolabelled NPY ligands, among them [$^{125}$I]NPY and [$^{125}$I]peptide YY (PYY), in combination with subtype-selective displacers. The Y2 receptor has been localized by combining [$^{125}$I]PYY with the Y2-selective mask NPY$_{13-36}$ (94). The results of such studies suggest that the Y2 receptor is widely distributed in rat brain, being most abundant in the hippocampus, olfactory bulb, and hypothalamus. We have seen no NPY Y2 mRNA in the olfactory bulb, but both hippocampus and hypothalamus contain Y2 mRNA. However, the pharmacological characterization of NPY receptor subtypes is incomplete at present, and some of the Y2-like binding may be attributable to the so-called atypical Y1 receptor, or to other undiscovered NPY receptor subtypes. Our in situ results suggest that the receptor autoradiographic characterization of the Y2 receptor is likely to be accurate for some areas. The projection fields of neurons containing the Y2 mRNA are important in this respect. Thus the pyramidal neurons of the CA3 region of the hippocampus, which contain relatively intense Y2 hybridization signals, project in a topographic fashion to the lateral septum (102), an area which supposedly contains a high proportion of Y2 receptors (103, 23, 94). Similarly, the olfactory bulb appears to contain mainly NPY receptors of the Y2 subtype. While there is no Y2 mRNA in the olfactory bulb, the piriform cortex contains many neurons which are labelled with the Y2 antisense probe, and provides a major source of olfactory bulb afferents. The localization of NPY Y2 mRNA in the arcuate nucleus of the hypothalamus is particularly interesting, as NPYir neurons in this nucleus provide the NPY innervation of much of the hypothalamus, including the paraventricular and dorsomedial nuclei (104, 105). It is unclear at present which receptor subtype(s) predominate in the paraventricular nucleus, but based on our results with the Y2 mRNA, and those of Mikkelsen and colleagues with the Y1 mRNA (106, 107), both Y1 and Y2 should be present. Similar arguments can be pursued for most of the regions which contain Y2 mRNA, however a definitive profile of Y2 receptor localization awaits the introduction of Y2 selective ligands.

Functional Considerations

Neuropeptide Y is involved in a number of physiological functions, including the regulation of food intake, neuronal excitability, cardiovascular regulation, and circadian rhythms. With regard to food intake, the paraventricular nucleus of the hypothalamus is one site which has been intensively investigated, and has been demonstrated to be a prominent locus of action for the orexigenic effects of NPY. The localization of NPY Y2 mRNA in the arcuate nucleus, and the projections of the arcuate to the paraventricular nucleus, suggest the involvement of this receptor in feeding.

In the hippocampus, NPY immunoreactivity is found mainly in interneurons which innervate pyramidal cells. Here, NPY has been demonstrated to reduce synaptic excitation in areas CA1 and CA3. This has been assumed to be mediated by a Y2 receptor (108), as C-terminal fragments of NPY are effective in the assay. The localization of Y2 mRNA in pyramidal cells of CA3 indicates that this receptor may be involved in the termination of convulsive activity, such as in epilepsy.

The rat Y2a and Y2b receptor analogs represent essential tools for pharmaceutical drug development. Drug candidates screened primarily against human receptors must also be characterized at the rat (or other relevant species analog) so that data generated from in vivo models can be interpreted accurately. While the current panel of peptides revealed no major differences in pharmacological profile between the human Y2 and rat Y2a receptor analogs, even a single amino acid difference between receptors displaying high sequence similarity could have dramatic effects on ligand binding affinity (109). The rat Y2b receptor represents an additional opportunity to evaluate species-dependent differences in ligand binding. It remains to be determined whether the rat Y2b receptor plays a singular role in rat Y2 receptor pharmacology, due either to unique ligand binding properties or to distinctive localization patterns.

We established functional assays for human Y2 receptor activation in both 293 and NIH-3T3 cells based on receptor-dependent inhibition of forskolin-stimulated cAMP accumulation (Table 9). The $EC_{50}$ values for peptides in these assays were generally smaller than the corresponding $K_i$ values, suggesting that receptor activation occurs through a high affinity state of the receptor which is not predominantly represented under the conditions of the binding assay. Such a scenario would be consistent with the weak effect of Gpp(NH)p on radioligand binding to the human Y2 receptor in membrane homogenates.

Our characterization of the Y2 receptor stably expressed in 293 cells also shows definitively that the Y2 receptor can couple simultaneously to both cAMP regulation and calcium mobilization in a single cell type. The calcium mobilization in 293 cells, at least, appears to occur through a pertussis toxin-sensitive G protein. The $EC_{50}$ for the human PYY-mediated calcium response is significantly larger than that for the cAMP response in the same host cell (39 nM vs. 0.31 nM, respectively), suggesting that calcium mobilization requires promiscuous coupling of the receptor to a G protein other than that involved in cyclase regulation. The exact identities of the G proteins mediating these receptor activation events, whether $G_i$, $G_o$, $G_z$ or another type, remain to be determined.

We now have several Y2 receptor expression systems from which to choose, each uniquely suited to different uses.

The transient expression system in COS-7, for example, allows us to generate sufficient quantities of membranes for routine structure/activity relationship measurements. We can also produce mutant receptors by site-directed mutagenesis or related enzymatic techniques and express them transiently in COS-7 for a comparison of pharmacological properties with those of the wild-type receptor. In this way, we can gain insight into receptor binding pockets, ligand binding domains, and mechanisms of activation. The stable expression system in 293 and NIH-3T3 cells offers the convenience of a single transfection followed by routine passaging techniques. The stable expression system also offers the opportunity to select for optimum receptor expression levels, G protein populations, and signal transduction pathways, all of which are critical elements for in vitro functional assays. Such assays can be used to determine agonist or antagonist activity in receptor-selective compounds, thereby generating critical information for drug design.

The expression cloning of a human Y2 receptor allows, for the first time, the ability to develop NPY-receptor subtype specific drugs and represents a major advance in our ability to analyze NPY-mediated physiological processes. Pharmacologically defined Y2 receptors have a widespread anatomical distribution (2). They represent the predominant NPY receptor in brain, with the highest density in hippocampus and relatively high expression in almost all other areas including olfactory bulb, basal ganglia, amygdaloid complex, thalamic and hypothalamic nuclei, pituitary, pineal gland, cerebellum, and brainstem. This distribution is consistent with northern blot analysis, which shows that the Y2 MRNA is present in amygdala, candate nucleus, corpus callosum, hippocampus, hypothalamus, substantia nigra and subthalamic nucleus. Peripheral localization includes sympathetic neurons, dorsal root ganglia, stomach chief cells, intestinal enterocytes, kidney proximal tubule, trachea, and vascular smooth muscle. Y2 receptors are therefore in a position to potentially regulate a variety of physiological functions including cognitive enhancement, circadian rhythm, EEG synchronization, body temperature, blood pressure, locomotor activity, neuroendocrine release, sympathetic activation, sensory transmission, gastrointestinal function, intestinal secretion, renal absorption, and cardiovascular function (1, 2).

Y2 receptors are attractive targets for drug design (1). Y2 receptor regulation may be useful in the treatment of several pathophysiological conditions (1, 2) including memory loss (111), epileptic seizure (72), pain (64), depression, hypertension, locomotor problems, sleep disturbances, eating disorders, sexual/reproductive disorders, nasal congestion (97), and diarrhea (112). A rigorous investigation of Y2-related pathophysiology has been hindered by the absence of suitable non-peptide ligands. The chemical synthesis of subtype selective agonists and antagonists as potential drug candidates will be greatly accelerated by screening against a homogeneous population of cloned human Y2 receptors. As more specific pharmacological tools become available for probing receptor function, additional therapeutic indications are likely to be discovered.

We do not know whether the human and rat Y2 receptors we have discovered account for all of the pharmacological Y2 receptors so far described, or whether the Y2 receptor population is further divided into distinct receptor subtypes. Indeed, there is some suggestion of receptor heterogeneity within the Y2 receptor population (2). These are issues which can now be resolved using nucleotide sequence from the human Y2 receptor as the basis for in situ localization, anti-sense strategies, homology cloning, and related techniques. Such approaches will enable us to investigate the existence of potentially novel NPY receptor subtypes, in humans and other species, with additional pharmacologic and therapeutic significance.

TABLE 1

% aminoacid TM identity of the NPY-2 receptor with other 7 TM Receptors

| m MUSGIR | 42 | h Y-1 | 41 | |
|---|---|---|---|---|
| | | h Y-4 | 41 | |
| h 5HT1A | 28 | h Adenosine A2b | 28 | h |
| Substance K | 33 | | | |
| h 5HT2 | 31 | h Adenosine A1 | 29 | h |
| Substance p | 32 | | | |
| h α-adrenergic-1b | 34 | h Dopamine D1 | 31 | h |
| Neurokinin-3 | 33 | | | |
| h α-adrenergic-2a | 34 | h Dopamine D2 | 32 | h |
| Interleukin-8 | 33 | | | |
| h β-adrenergic-1 | 35 | bov Hist H1 | 25 | h |
| Angiotensin$_1$ | 33 | | | |
| | | h Hist H2 | 28 | h |
| Angiotensin$_2$ | 27 | | | |
| | | | | m |
| Thyrotropin releasing hormone | 27 | | | |
| | | | | h |
| Bradykinin | 25 | | | |
| | | | | r |
| mas oncogene | 20 | | | |

TABLE 2

Pharmacologically defined receptors for NPY and related pancreatic polypeptides. Rank orders of affinity are based on published reports of binding and functional data (M9, M24, M3, M10). Missing peptides in the series reflect a lack of published information.

| | Affinity ($-pk_i$ or $-pEC_{50}$) | | | | | |
|---|---|---|---|---|---|---|
| Receptor | 11 to 10 | 10 to 9 | 9 to 8 | 8 to 7 | 7 to 6 | <6 |
| Y1 | NPY<br>PYY<br>[Leu$^{31}$,Pro$^{34}$]NPY | | NPY$_{2-36}$ | NPY$_{13-36}$ | PP | |
| Y2 | | PYY<br>NPY<br>NPY$_{2-36}$ | NPY$_{13-36}$ | | | [Leu$^{31}$,Pro$^{34}$]NPY<br>PP |
| Y3 | | NPY | [Pro$^{34}$]NPY | NPY$_{13-36}$<br>PP | | PYY |
| PP | PP | | [Leu$^{31}$,Pro$^{34}$]NPY | | | NPY |

TABLE 3

Pharmacological profile of the CG-13 receptor.
Binding data reflect competitive displacement of $^{125}$I-PYY from membranes of COS-7 cells transiently expressing CG-13 receptors. Peptides were tested at concentrations ranging from 0.001 nM to 100 nM. $IC_{50}$ values corresponding to 50% displacement were determined by nonlinear regression analysis and converted to $K_i$ values according to the equation, $K_i = IC_{50}/(1 + [L]/K_d)$, where $[L]$ is the $^{125}$I-PYY concentration and $K_d$ is the equilibrium dissociation constant of $^{125}$I-PYY. The data shown are representative of at least two independent experiments

| Competitor | Human Y1, $K_i$ (nM) | CG-13, $K_i$ (nM) | SK-N-Be(2), $K_i$ (nM) |
|---|---|---|---|
| human PYY | 0.085 ± 0.021 | 0.39 ± 0.05 | 0.11 ± 0.02 |
| human NPY | 0.049 ± 0.009 | 0.69 ± 0.14 | 0.13 ± 0.02 |
| porcine $NPY_{2-36}$ | 1.4 ± 0.2 | 0.78 ± 0.13 | 0.41 ± 0.09 |
| porcine NPY | 0.049 ± 0.001 | 0.86 ± 0.13 | 0.28 ± 0.04 |
| porcine $PYY_{13-36}$ | 32 ± 7 | 1.5 ± 0.2 | 0.86 ± 0.14 |
| porcine $NPY_{18-36}$ | 28 ± 5 | 1.5 ± 0.2 | 2.1 ± 0.5 |
| porcine $NPY_{13-36}$ | 51 ± 16 | 2.4 ± 0.4 | 1.8 ± 0.4 |
| porcine $NPY_{20-36}$ | 62 ± 6 | 3.4 ± 0.3 | 3.1 ± 0.6 |
| porcine $NPY_{16-36}$ | 45 ± 4 | 3.8 ± 0.7 | 5.0 ± 0.5 |
| porcine $NPY_{22-36}$ | 170 ± 30 | 4.6 ± 0.1 | 3.2 ± 0.6 |
| porcine $NPY_{26-36}$ | >300 | 210 ± 60 | 70 ± 7 |
| human NPY free acid | >300 | >300 | 280 ± 120 |
| human PP | 200 ± 70 | >300 | >300 |
| human [Leu$^{31}$,Pro$^{34}$] NPY | 0.13 ± 0.02 | >300 | >300 |

TABLE 4

Extended pharmacological binding profile of the human Y2 receptor vs. other Y-type receptors cloned from human. Binding data reflect competitive displacement of $^{125}$I-PYY from membranes of COS-7 cells transiently expressing human Y1, human Y2, and human Y4 receptors. $IC_{50}$ values corresponding to 50% displacement were determined by nonlinear regression analysis and converted to $K_i$ values according to the equation Chang-Prusoff equation, $K_i = IC_{50}/(1 + [L]/K_d)$, where $[L]$ is the $^{125}$I-PYY concentration and $K_d$ is the equilibrium dissociation constant of $^{125}$I-PYY. Any peptide not included in initial characterization shown in previous tables is referred to as a "new peptide". Data shown are representative of at least two independent experiments.

| Peptide | Y1 | Y2 | Y4 | Comments |
|---|---|---|---|---|
| NPY, human | 0.08 | 0.74 | 2.2 | |
| NPY, porcine | 0.07 | 0.81 | 1.1 | |
| NPY, frog (melanostatin) | 0.07 | 0.87 | 1.2 | new peptide |
| O—Me-Tyr$^{21}$-NPY, human | 0.12 | 1.6 | 6.1 | new peptide |
| C2-NPY, porcine | 73 | 3.5 | 120 | new peptide |
| $NPY_{2-36}$, human | 3.6 | 2.0 | 16 | new peptide |
| $NPY_{2-36}$, porcine | 2.4 | 1.2 | 5.6 | |
| $NPY_{13-36}$, porcine | 70 | 2.5 | 38 | |
| $NPY_{16-36}$, porcine | 41 | 3.6 | 54 | |
| $NPY_{18-36}$, porcine | 70 | 4.2 | >300 | |
| $NPY_{20-36}$, porcine | 63 | 3.6 | 120 | |
| $NPY_{22-36}$, porcine | >1000 | 18 | >990 | |
| $NPY_{26-36}$, porcine | >1000 | 380 | 300 | |
| [Leu$^{31}$,Pro$^{34}$]NPY, human | 0.15 | >130 | 1.1 | |
| [Leu$^{31}$,Pro$^{34}$]NPY, porcine | 0.15 | >540 | 1.5 | new peptide |
| NPY free acid, human | 490 | >1000 | >1000 | |
| $NPY_{1-24}$ amide, human | >1000 | >1000 | >1000 | new peptide |
| [D-Trp$^{32}$]NPY, human | >1000 | >1000 | >1000 | new peptide |
| PYY, human | 0.19 | 0.36 | 0.87 | |
| PYY, porcine | 0.14 | 0.35 | 1.3 | new peptide |
| $PYY_{3-36}$, human | 45 | 0.70 | 14 | new peptide |
| $PYY_{13-36}$, porcine | 33 | 1.5 | 46 | |
| [Pro$^{34}$]PYY, human | 0.14 | >310 | 0.12 | new peptide |
| PP, human | 77 | >1000 | 0.06 | |
| PP, bovine | 240 | >830 | 0.05 | new peptide |
| PP, rat | 460 | >1000 | 0.18 | new peptide |
| PP, avian | 400 | >1000 | 7.0 | new peptide |
| PP, frog | 98 | >1000 | 61 | new peptide |
| PP, salmon | 0.20 | 0.17 | 3.2 | new peptide |
| [Ile$^{31}$, Gln$^{34}$]PP, human | >86 | 20 | 0.09 | new peptide |
| PYX-1 | 507 | 684 | 794 | new peptide |
| PYX-2 | >1000 | >1000 | >1000 | new peptide |

TABLE 5

Macrolocalization of human Y2 receptor mRNA in human tissues by PCR.
Localization data reflect PCR-based amplification of human Y2 cDNA derived from mRNA extracts of human tissues. Southern blots of the PCR products were prepared and hybridized with $^{32}$P-labeled oligonucleotide probes selective for Y-type receptor subtypes. The labeled products were recorded on X-ray film and the relative signal density was determined by visual inspection. In this rating scheme, + = faint signal, ++ = moderate signal, +++ = intense signal.

| Human tissues | Human Y2 PCR Product |
| --- | --- |
| total brain | +++ |
| frontal brain | ++ |
| ventricle (heart) | ++ |
| atrium (heart) | (−) |
| thoracic aorta | +++ |
| coronary artery | ++½ |
| nasal mucosa | + |
| mesentery | ++ |
| stomach | ++ |
| ileum | ++ |
| pancreas | + |
| liver | (−) |
| kidney | + |
| bladder | +½ |
| penis | +++ |
| testes | not determined |
| uterus (endometrium) | (−) |
| uterus (myometrium) | (−) |

TABLE 6

Peptide binding profile of the rat Y2a receptor vs. the human Y2 receptor.
Binding data reflect competitive displacement of $^{125}$I-PYY from membranes of COS-7 cells transiently expressing rat Y2a and human Y2 receptors. IC$_{50}$ values corresponding to 50% displacement were determined by nonlinear regression analysis and converted to K$_i$ values according to the equation Chang-Prusoff equation, $K_i = IC_{50}/(1 + [L]/K_d)$, where [L] is the $^{125}$I-PYY concentration and K$_d$ is the equilibrium dissociation constant of $^{125}$I-PYY. Data shown are representative of at least two independent experiments.

| Peptide | Rat Y2a | Human Y2 |
| --- | --- | --- |
| NPY, human | 1.3 | 0.74 |
| NPY$_{2-36}$, human | 2.2 | 1.2 |
| NPY$_{13-36}$, human | 31 | 2.5 |
| NPY$_{20-36}$, porcine | 93 | 3.6 |
| NPY$_{26-36}$, porcine | >830 | 380 |
| NPY free acid, human | >980 | >1000 |
| [Leu$^{31}$,Pro$^{34}$]NPY, human | >1000 | >130 |
| [D-Trp$^{32}$]NPY, human | >830 | >1000 |
| PYY, porcine | 0.28 | 0.35 |
| PYY$_{13-36}$, porcine | 1.5 | 28 |
| PP, human | >1000 | >1000 |
| PP$_{31-36}$, human | >10000 | >10000 |
| PP, salmon | 0.17 | 0.17 |
| PP, bovine | >1000 | >825 |
| PP, rat | >1000 | >1000 |

TABLE 7

Oligonucleotide probe sequences used for in situ hybridization

| Probe | Sequence | Location | Orientation |
| --- | --- | --- | --- |
| KS972 | 5'-GGC CCA TTA GGT GCA GAG GCA GAT GAG AAT CAA ACT GTA GAA GTG-3' SEQ ID NO:24 | NH$_2$-terminus | sense |
| KS974 | 5'-CAC TTC TAC AGT TTG ATT CTC ATC TGC CTC TGC ACC TAA TGG GCC-3' SEQ ID NO:25 | NH$_2$-terminus | antisense |
| KS973 | 5'-CGG AGG TGT CCA TGA CCT TCA AGG CTA AAA AGA ACC TGG AAG TCA-3' SEQ ID NO:26 | COOH terminus | sense |
| KS975 | 5'-TGA CTT CCA GGT TCT TTT TAG CCT TGA AGG TCA TGG ACA CCT CCG-3' SEQ ID NO:27 | COOH terminus | antisense |

TABLE 8

Distribution of NPY Y2 mRNA in the rat CNS.
Positive hybridization signals are indicated by "+" signs, no signal by "−", and a low signal by "+/−".

| Region | Hybridization |
| --- | --- |
| Cortex | |
| layer 2 | − |
| layer 6 | − |
| piriform | + |
| entorhinal | − |
| cingulate | − |
| Olfactory bulb | − |
| Anterior olfactory n. | − |
| Basal ganglia | |
| caudate-putamen | +/− |
| n. accumbens | − |
| olfactory tubercle | + |
| globus pallidus | − |
| islands of Calleja | − |
| Septal area | |
| lateral septum | + |
| medial septum | − |
| septohippocampal | − |
| diagonal band n. | − |
| Claustrum | − |
| Dorsal endopiriform | − |
| Hypothalamus | |
| anterior | − |
| paraventricular | + |
| dorsomedial | + |
| ventromedial | + |
| arcuate | + |
| lateral | − |
| mammillary | + |
| tuberal | + |
| Thalamus | |
| anterior nuclei | − |
| paraventricular n. | + |
| rhomboid n. | − |
| reuniens n. | − |
| mediodorsal n. | − |
| ventral nuclei | − |
| reticular n. | − |
| centrolateral n. | − |
| centromedial n. | + |
| zona incerta | − |

TABLE 8-continued

Distribution of NPY Y2 mRNA in the rat CNS. Positive hybridization signals are indicated by "+" signs, no signal by "−", and a low signal by "+/−".

| Region | Hybridization |
| --- | --- |
| lateral posterior n. | − |
| lateral dorsal n. | − |
| posterior n. | − |
| medial geniculate n. | − |
| dorsal lateral gen. | − |
| ventral lateral gen. | − |
| habenula | − |
| Hippocampus | |
| CA1 | − |
| CA2 | − |
| CA3 | + |
| subiculum | − |
| presubiculum | − |
| parasubiculum | − |
| Dentate gyrus | |
| granule cell layer | − |
| polymorph layer | − |
| Amygdala | |
| anterior | − |
| medial | + |
| cortical | + |
| amygdalohipp. | − |
| basomedial | + |
| basolateral | − |
| lateral | − |
| central | + |
| bed nucleus | − |
| Midbrain | |
| superior colliculus | − |
| inferior colliculus | − |
| mes. trigeminal | − |
| dorsal raphe | + |
| caudal linear raphe | + |
| median raphe | − |
| raphe magnu | − |
| substantia nigra | − |
| central gray | − |
| Pons/medulla | |
| locus coeruleus | − |
| subcoeruleus | − |
| parabrachial n. | − |
| facial n. | − |
| pontine n. | + |
| pontine ret. n. | − |
| reticulotegmental | + |
| A5 | − |
| A7 | − |
| gigantocellular | − |
| lateral reticular n. | − |
| motor trigeminal | NA |
| spinal trigeminal | NA |
| medial vestibular | − |
| solitarius | NA |
| dorsal vagus | NA |
| hypoglossal | NA |
| Cerebellum | |
| granule cell layer | − |
| molecular layer | − |
| Purkinje cells | − |
| deep nuclei | − |
| Spinal cord | |
| dorsal horn | − |
| ventral horn | + |
| intermediolateral | − |
| Dorsal root ganglia | + |

Abbreviations
1–9 spinal cord laminae
Arc arcuate n. hypothalamus
BMP posterior basomedial n. amygdala
CA3 field CA3 of the hippocampus
CC central canal
Cli caudal linear raphe n.
CM centromedial n. thalamus
DMH dorsomedial n. hypothalamus
DR dorsal raphe n.
LSV lateral septum, ventral
Me medial n. amygdala
MeAV medial n. amygdala, anteroventral division
PDTg posterior dorsal tegmental n.
Pir piriform cortex
PMD dorsal premammillary n.
PMCo posterior medial cortical n. amygdala
Pn pontine n.
PVH paraventricular n. hypothalamus
PVT paraventricular n. thalamus
TC tuber cinereum
TuO olfactory tubercle
VMH ventromedial n. hypothalamus

TABLE 9

Functional activation of the human Y2 receptor and inhibition of cAMP accumulation.

$K_i$ values were derived from binding assays as described in Table 1. Peptides were evaluated for binding affinity and then analyzed for functional activity. Functional data were derived from radio-immunoassay of cAMP accumulation in stably transfected 293 cells stimulated with 10 $\mu$M forskolin. The maximum inhibition of cAMP accumulation relative to that produced by human NPY ($E_{max}$) and the concentration producing a half-maximal effect ($EC_{50}$) were determined by nonlinear regression. Data shown are representative of at least two independent experiments.

| Peptide | Binding $K_i$ (nM) | Function $EC_{50}$ (nM) | $E_{max}$ |
| --- | --- | --- | --- |
| NPY, human | 0.74 | 0.25 | 100% |
| NPY, porcine | 0.81 | 0.20 | 113% |
| C2-NPY, porcine | 3.5 | 0.14 | 116% |
| $NPY_{2-36}$, human | 2.0 | 0.35 | 94% |
| $NPY_{2-36}$, porcine | 1.2 | 1.2 | 96% |
| $NPY_{13-36}$, porcine | 2.5 | 1.7 | 110% |
| $NPY_{16-36}$, porcine | 3.6 | 1.8 | 92% |
| $NPY_{18-36}$, porcine | 4.2 | 2.1 | 92% |
| $NPY_{20-36}$, porcine | 3.6 | 3.2 | 77% |
| $NPY_{22-36}$, porcine | 18 | 2.3 | 88% |
| [$Leu^{31}$, $Pro^{34}$]NPY, human | >130 | >3000 | not determined |
| [$Leu^{31}$, $Pro^{34}$]NPY, porcine | >540 | >3000 | not determined |
| [$D-Trp^{32}$]NPY, human | >1000 | >3000 | not determined |

TABLE 9-continued

Functional activation of the human Y2 receptor
and inhibition of cAMP accumulation.
$K_i$ values were derived from binding assays as described in Table 1.
Peptides were evaluated for binding affinity and then analyzed for
functional activity. Functional data were derived from radio-
immunoassay of cAMP accumulation in stably transfected 293 cells
stimulated with 10 $\mu$M forskolin. The maximum inhibition of cAMP
accumulation relative to that produced by human NPY ($E_{max}$) and
the concentration producing a half-maximal effect ($EC_{50}$) were
determined by nonlinear regression. Data shown
are representative of at least two independent experiments.

| Peptide | Binding $K_i$ (nM) | $EC_{50}$ (nM) | $E_{max}$ |
|---|---|---|---|
| PYY, human | 0.36 | 0.31 | 100% |
| PYY, porcine | 0.35 | 0.16 | 103% |
| $PYY_{3-36}$, human | 0.70 | 0.22 | 99% |
| $PYY_{13-36}$, porcine | 1.5 | 0.13 | 102% |
| [$Pro^{34}$]PYY, human | >310 | >120 | not determined |
| PP, salmon | 0.17 | 0.07 | 79% |
| PYX-1 | 684 | >3000 | not determined |
| PYX-2 | >1000 | >3000 | not determined |

REFERENCES

1. Wahlestedt, C., and D. J. Reis. (1993). Neuropeptide Y-Related Peptides and Their Receptors—Are the Receptors Potential Therapeutic Targets? Ann. Rev. Pharmacol. Tox., 32, 309–352.
2. Dumont, Y., J.-C. Martel, A. Fournier, S. St-Pierre, and R. Quirion. (1992). Neuropeptide Y and neuropeptide Y receptor subtypes in brain and peripheral tissues. Progress in Neurobiology, 38, 125–167.
3. Schwartz, T. W., J. Fuhlendorff, L. L. Kjems, M. S. Kristensen, M. Vervelde, M. O'Hare, J. L. Krstenansky, and B. Bjornholm. (1990). Signal epitopes in the three-dimensional structure of neuropeptide Y. Ann. N.Y. Acad. Sci., 611, 35–47.
4. Fuhlendorff, J., U. Gether, L. Aakerlund, N. Langeland-Johansen, H. Thogersen, S. G. Melberg, U. B. Olsen, O. Thastrup, and T. W. Schwartz. (1990). [$Leu^{31}$,$Pro^{34}$] Neuropeptide Y: A specific $Y_1$ receptor agonist. Proc. Natl. Acad. Sci. U.S.A., 87, 182–186.
5. Grundemar, L., J. L. Krstenansky, and R. Hakanson. (1992). Activation of neuropeptide Y1 and neuropeptide Y2 receptors by substituted and truncated neuropeptide Y analogs: identification of signal epitopes. Eur. J. Pharmacol., 232, 271–278.
6. Beck, A. G., G. Jung, W. Gaida, H. Koppen, R. Lang, and G. Schnorrenberg. (1989). Highly potent and small neuropeptide Y agonist obtained by linking $NPY_{1-4}$ via a spacer to alphahelical NPY25-36. FEBS Lett., 244, 119–122.
7. Beck-Sickinger, A. G., W. Gaida, G. Schnorrenberg, R. Lang, and G. Jung. (1990). Neuropeptide Y: Identification of the binding site. Int. J. Peptide Protein Res., 36, 522–530.
8. Wahlestedt, C., Regunathan, S., and D. J. Reis. (1991). Identification of cultured cells selectively expressing Y1-, Y2-, or Y3-type receptors for neuropeptide Y/peptide YY. Life Sciences, 50, PL-7–PL-12.
9. Schwartz, T. W., S. P. Sheikh, and M. M. T. O'Hare. (1987). Receptors on phaeochromocytoma cells for two members of the PP-fold family—NPY and PYY. FEBS Lett., 255, 209–214.
10. Larhammar, D., A. G. Blomqvist, F. Yee, E. Jazin, H. Yoo, and C. Wahlestedt. (1992). Cloning and functional expression of a human neuropeptide Y/peptide YY receptor of the Y1 type. J. Biol. Chem., 267, 10935–10938.
11. Herzog, H., Y. J. Hort, H. J. Ball, G. Hayes, J. Shine, and L. Selbie. (1992). Cloned human neuropeptide Y receptor couples to two different second messenger systems. Proc. Natl. Acad. Sci. U.S.A., 89, 5794–5798.
12. Eva, C., Keinanen, K., Monyer, H., Seeburg, P., and Sprengel, R. (1990). Molecular cloning of a novel G protein-coupled receptor that may belong to the neuropeptide receptor family. FEBS Lett., 271, 80–84.
13. Chirgwin, J. M., A. E. Przybyla, R. J. MacDonald, and W. J. Rutter. (1979). Isolation of biologically active ribonucleic acid from sources enriched in ribonuclease. Biochemistry, 18, 5294–5299.
14. Gubler, U and B. J. Hoffman. (1983). A simple and very efficient method for generating cDNA libraries. Gene, 25, 263–269.
15. Aruffo, A. and Seed, B. (1987). Molecular cloning of a CD28 cDNA by a high efficiency COS Cell expression system. Proc. Natl. Acad. Sci. USA, 84, 8573–8577.
16. Sambrook, J., Fritsch, E. F. and Maniatis, T. (1989). Molecular cloning: a laboratory manual (Cold Spring Harbor Laboratory Press, Cold Spring Harbor, N.Y.), 2nd Ed.
17. Warden, D. and H. V. Thorne. (1968). Infectivity of polyoma virus DNA for mouse embryo cells in presence of diethylaminoethyl-dextran. J. Gen. Virol., 3, 371.
18. Mc Cormick, M. (1987). Sib Selection. Methods in Enzymology, 151, 445–449.
19. Bradford, M. M. (1976). A rapid and sensitive method for the quantitation of microgram quantities of protein utilizing the principle of protein-dye binding. Anal. Biochem., 72, 248–254.
20. Gearing, D. P., King, J. A.,Gough, N. M. and Nicola N. A. (1989). Expression cloning of a receptor for human granulocyte-macrophage colony-stimulating factor. EMBO J., 8, 3667–3676.
21. Kluxen, F. W., Bruns, C. and Lubbert H. (1992). Expression cloning of a rat brain somatostatin receptor cDNA. Proc. Natl. Acad. Sci., 89, 4618–4622.
22. Kieffer, B., Befort, K., Gaveriaux-Ruff, C. and Hirth, C. G. (1992). The 6-opioid receptor: Isolation of a cDNA by expression cloning and pharmacological characterization. Proc. Natl. Acad. Sci., 89, 12048–12052.
23. Dumont, Y., A. Fournier, S. St.-Pierre, Schwartz, T. W. and R. Quirion. (1990). Differential distribution of neuropeptide Y1 and Y2 receptors in the rat brain. Eur. J. Pharmacol., 191, 501–503.
24. Aicher,S. A., Springston, M., Berger, S. B., Reis, D. J. and Wahlestedt, C. (1991). Receptor selective analogs demonstrate NPY/PYY receptor heterogeneity in rat brain. Neurosci. lett., 130, 32–36.
25. Wei Li and T. D. Hexum. (1991). Characterization of neuropeptide Y (NPY) receptors in human hippocampus. Brain Research., 553, 167–170.
26. Bayer, S. A. (1985). Hippocampal Region, in The rat nervous system, Vol. I, p335–352. (Acad. Press, George Paxinos Ed.).
27. Kozak, M. (1989). The scanning model for translation: an update. J. Cell Biol. 108, 229–241.
28. Kozak, M. (1991). Structural features in eukaryotic mRNAs that modulate the initiation of translation. J. Biol. Chem., 266, 19867–19870.

29. Kornfeld, R. and Kornfeld, S. (1985). Assembly of asparagine linked oligosaccharides. Annu. Rev. Biochem., 54, 631–664.
30. Probst, W. C., Snyder, L. A., Schuster, D. I., Brosius, J and Sealfon, S. C. (1992). Sequence alignment of the G-protein coupled receptor superfamily. DNA and Cell Bio., 11, 1–20.
31. O'Dowd, B. F., M. Hantowich, M. G. Caron, R. J. Lefkowitz and M. Bouvier. Palmitoylation of the human $\beta_2$-adrenergic receptor. J.B.C., 264, 7564–7569 (1989).
32. Findlay, J. and Eliopoulos, E. (1990). Three dimensional modelling of G protein-linked receptors. Science, 11, 492–499.
33. Harrigan, M. T., Faith Campbell N. and Bourgeois S. (1991). Identification of a gene induced by glucocorticoids in murine T-cells: A potential G protein-coupled receptor. Molecular Endocrinology, 5, 1331–1338.
34. Fuhlendorff, J., A. G. Beck-Sickinger, A. Holm, M. Barfoed, K. Borch, H. Lund, B. Lundt, N. L. Johansen, H. Thogersen, and T. W. Schwartz. (1993). Membrane association of NPY—a prerequisite for receptor binding. Neuropeptide Y Conference Abstracts, Cambridge. B40.
35. Sheikh, S. P., M. M. T. O'Hare, 0. Tortora, and T. W. Schwartz. (1989). Binding of monoiodinated neuropeptide Y to hippocampal membranes and human neuroblastoma cell lines. J. Biol. Chem., 264, 6648–6654.
36. Li, W. and T. D. Hexum. (1991). Characterization of neuropeptide Y (NPY) receptors in human hippocampus. Brain Research, 553, 167–170.
37. Colmers, W. F., G. J. Klapstein, A. Fournier, S. St-Pierre, and K. A. Treherne. (1991). Presynaptic inhibition by neuropeptide Y in rat hippocampal slice in vitro is mediated by a Y2 receptor. Br. J. Pharmacol., 102, 41–44.
38. Stanley, B. G., W. Magdalin, A. Seirafi, M. M. Nguyen, and S. F. Leibowitz. (1992). Evidence for neuropeptide Y mediation of eating produced by food deprivation and for a variant of the $Y_1$ receptor mediating this peptide's effect. Peptides, 13, 581–587.
39. Rimland, J., W. Xin, P. Sweetnam, K. Saijoh, E. J. Nestler, and R. S. Duman. (1991). Sequence and expression of a neuropeptide Y receptor cDNA. Mol. Pharmacol., 40, 869–875.
40. Li, X.-J., Y.-N. Wu, R. A. North, and M. Forte. (1992). Cloning, functional expression, and developmental regulation of a neuropeptide Y receptor from *Drosophila melanogaster*. J. Biol. Chem., 267, 9–12.
41. Jazin, E. E., Yoo, H., Blomqvist, A. G., Yee, F., Weng, G., Walker, M. W., Salon, J., Larhammar, D., and Wahlestedt, C. (1993). A proposed bovine neuropeptide Y (NPY) receptor cDNA clone, or its human homologue, confers neither NPY binding sites nor NPY responsiveness on transfected cells. Reg. Peptides, 47, 247–258.
42. Herzog, H., Y. J. Hort, J. Shine, and L. A. Selbie. (1993). Molecular cloning, characterization, and localization of the human homolog to the reported bovine NPY Y3 receptor: lack of NPY binding and activation. DNA and Cell Biology, 12, 465–471.
43. Wahlestedt, C., Grundemar, L., Hakanson, R., Heilig, M., Shen, G. H., Zukowska-grojec, Z. and Reis, D. J. (1990). Neuropeptide Y receptor subtypes, Y1 and Y2. Ann. NY Acad. Sci., 611, 7–26.
44. Unden, A. and Bartfai, T. (1984). Regulation of neuropeptide Y (NPY) binding by guanine nucleotide in rat cerebral cortex. FEBS Lett., 177, 125–128.
45. Michel, M. C. (1991). Receptors for neuropeptide Y: multiple subtypes and multiple second messengers. Trends Pharmacol. Sci., 12, 389–394.
46. De Wied, D. In: Neuropeptides: Basics and Perspectives (Elsevier, Amsterdam-New York-Oxford), 1990.
47. Heilig, M. and E. Widerlov. Neuropeptide Y: an overview of central distribution, functional aspects, and possible involvement of neuropsychiatric illnesses. Acta Psychiatr. Scand., 82, 95–114 (1990).
48. Lundberg, J. M., A. Hemsen, O. Larsson, A. Rudehill, A. Saria, and B. Fredholm. Neuropeptide Y receptor in pig spleen: binding characteristics, reduction of cyclic AMP formation and calcium antagonist inhibition of vasoconstriction. Eur. J. Pharmacol., 145, 21–29 (1988).
49. Hinson, J., C. Rauh, and J. Coupet. Neuropeptide Y stimulates inositol phospholipid hydrolysis in rat brain microprisms. Brain Res., 446, 379–382 (1988).
50. Mihara, S., Y. Shigeri, and M. Fujimoto. Neuropeptide Y-induced intracellular $Ca^{2+}$ increase in vascular smooth muscle cells. FEBS Lett., 259, 79–82 (1989).
51. Aakerlund, L., U. Gether, J. Fuhlendorff, T. W. Schwartz, and O. Thastrup. Y1 receptors for neuropeptide Y are coupled to mobilization of intracellular calcium and inhibition of adenylate cyclase. FEBS Lett., 260, 73–78 (1990).
52. Eva, C., A. Oberto, R. Sprengel, and E. Genazzani. The murine NPY-1 receptor gene: structure and delineation of tissue specific expression. FEBS Lett., 314, 285–288 (1992).
53. Wahlestedt, C., N. Yanaihara, and R. Hakanson. Evidence for different pre- and postjunctional receptors for neuropeptide Y and related peptides. Regul. Pept., 13, 307–318 (1986).
54. Bottcher, G., K. Sjolund, E. Ekblad, R. Hakanson, T. W. Schwartz, and F. Sundler. Co-existence of peptide YY in glicentin immunoreactivity in endocrine cells of the gut. Regul. Pept., 8, 261–273 (1984).
55. Laburthe, M., B. Chenut, C. Rouyer-Fessard, K. Tatemoto, A. Couvineau, A. Servin, and B. Amiranoff. Interaction of peptide YY with rat intestinal epithelial plasma membranes: binding of the radioiodinated peptide. Endocrinology, 118, 1910–1917 (1986).
56. Laburthe, M. Peptide YY and neuropeptide Y in the gut: Availability, biological actions, and receptors. Trends Endocrinol. Metab., 1, 168–174 (1990).
57. Voisin, T., M. Bens, F. Cluzeaud, A. Vandewalle, and M. Laburthe. Peptide YY receptors in the proximal tubule PKSV-PCT cell line derived from transgenic mice: relation with cell growth. J. Biol. Chem., 268, 20547–20554 (1993).
58. McDermott, B. J., Millar, B. B., and Piper, H. M. Cardiovascular effects of neuropeptide Y: receptor interactions and cellular mechanisms. Cardiovascular Research, 27, 893–905 (1993).
59. Westfall, T. C., Han, S. P., Kneupfer, M., Martin, J., Chen, X., Del Valle, Ciarleglio, A., and Nass, L. (1990). Neuropeptides in Hypertension: Role of Neuropeptide Y and Calcitonin Gene Related Peptide. Brit. J. Clin. Pharmacol., 30, 755–825 (1990).
60. Tsuda, K., Tsuda, S., Goldstein. M., and Masauyama, Y. Effects of Neuropeptide Y on Norepinephrine Release in Hypothtalmic Slices of Spontaneously Hypertensive Rats. Eur. J. Pharmacol., 182, 175–179 (1990).
61. Friel, D. D., Miller, R. J., an Walker, M. W. Neuropeptide Y: a powerful modulator of epithelial ion transport. Brit. J. Pharmacol., 88, 425–431 (1986).
62. Playford, R. J., Domin, J., Beecham, J., Parmark, K. I., Tatemoto, K., Bloom, S. R., and Calam, J. Peptide YY: A natural defense against diarrhoea. Lancet, 335, 1555–1557 (1990).

63. Colmers, W. F., Klapstein, G. J., Fournier, A., St-Pierre, S., and Treherne, K. A. Presynaptic Inhibition by neuropeptide Y in rat hippocampal slice in vitro is mediated by a Y2 receptor. Brit. J. Pharmacol., 102, 41–44 (1991).
64. Hua, X. Y., Boublik, J. H., Spicer, M. A., Rivier, J. E., Brown, M. R., and Yaksh, T. L. The antinociceptive effects of spinally administered Neuropeptide Y in the rat: systematic studies on structure-activity relationship. J. Pharmacol. Exp. Ther., 258, 243–253 (1991).
65. Calza, L., Giardino, L., Zanni, M., Velardo, A., Parchi, P., and Marrama, P. Daily changes of Neuropeptide Y-like immunoreactivity in the Suprachiamsmatic Nucleus of the rat. Regul. Pept., 27, 127–137 (1990).
66. Flood, J. F., Hernandez, E. N., and Morley, J. E. Modulation of memory processing by Neuropeptide Y. Brain Res., 421, 280–290 (1987).
67. Lacroix, J. S.; Auberson, S., Morel, D. R. Theodorsson, E., Hokfelt, T. and Lundberg, J. M. Vascular control of the pig nasal mucosa: distribution and effect of somatostatin in relation to noradrenaline and Neuropeptide Y. Regul. Pept., 40 (3), 373–87 (1992).
68. Modin, A., Pernow, J., and Lundberg, J. M. Evidence for two Neuropeptide Y receptors mediating vasoconstriction. Eur. J. Pharmacol. 203, 2, 165–171 (1991).
69. Lundberg, J. M., Franco-Cereceda, A., Lacroix, J. S., and Pernow, J. Neuropeptide Y and sympathetic neurotransmission. Ann. N.Y. Acad. Sci., 611, 166–174 (1990).
70. Lundberg, J. M. Peptidergic control of the autonomic regulation system in the orofacial region. Proc. Finn. Dent. Soc., 85, 4–5, 239–250 (1989).
71. Lacroix, J. S., Angg.ANG.ard, A., Hokfelt, T., O'Hare, M. M., Fahrenkrug, J. and Lundberg, J. M. Neuropeptide Y: presence in sympathetic and parasympathetic innervation of the nasal mucosa. Dept. of Pharm., Karolinska Institutet, Stockholm (1993).
72. Rizzi, M., Monno, A., Samanin, R., Sperk, G., and Vezzani, A., Electrical kindling of the hippocampus in association with functional activation of Neuropeptide Y containing neurons. Euro. J. Neurosci., 5, 1534–1538 (1993).
73. Miller J. and Germain R. N., Efficient cell surface expression of class II MHC molecules in the absence of associated invariant chain, J. Exp. Med., 164, 1478 (1986).
74. J. S. Cohen, Trends in Pharm. Sci., 10, 435 (1989).
75. H. M. Weintraub, Sci. Am. January (1990) p. 40.
76. N. Sarver et al., Science, 247, 1222 (1990).
77. Low, M. J., Lechan, R. M., Hammer, R. E. et al. Science, 231, 1002–1004 (1986).
78. Oberdick, J., Smeyne, R. J., Mann, J. R., Jackson, S. and Morgan, J. I. Science, 248, 223–226 (1990).
79. Hogan B. et al. Manipulating the Mouse Embryo, A Laboratory Manual, Cold Spring Harbor Laboratory (1986).
80. Capecchi M. R. Science, 244, 1288–1292 (1989).
81. Zimmer, A. and Gruss, P. Nature, 338, 150–153 (1989).
82. Sanger, S. (1977) Proc. Natl. Acad. Sci. USA 74:5463–5467.
83. Martel, J. C., Fournier, A., St-Pierre, S., Dumont, Y., Forest, M., and Quirion R. (1990). Comparative structural requirements of branin neuropeptide Y binding sites and vasdeferens neuropeptide Y receptors. Molec. Pharmac. 38, 494–502.
84. Grandt, D., Schimiczek, M., Beglinger, Ch,, Layer, P., Goebell, H., Eysselein, V. E., and Reeve Jr., J. R. (1994a). Two molecular forms of peptide YY (PYY) are abundant in human blood: characterization of a radioimmunoassay recognizing $PYY_{1-36}$ and $PYY_{3-36}$. Regulatory Peptides 51: 151–159.
85. Grandt, D., Schimiczek, M., Struk, K., Shively, J., Eysselein, V. E., Goebell, H., and Reeve Jr., J. R. (1994b). Characterization of two forms of peptide YY, PYY (1–36) AND PYY (3036), in the rabbit. Peptides 15: 815–820.
86. Jorgensen, J. C., Fuhlendorff, J., and Schwartz, T. W. (1990). Structure-function studies on neuropeptide Y and pancreatic polypeptide: evidence for two PP-fold receptors in vas deferens. Eur. J. Pharmac. 186: 105–114.
87. Tatemoto, K., Mann, M. J., and Shimizu, M. (1992) Synthesis of receptor antagonists of neuropeptide Y. Proc. Natl. Acad. Sci U.S.A. 89: 1174–1178.
88. Leibowitz, S. F., Zuereb, M., and Kim, T. (1992) Blockade of naturla and neuropeptide Y-induced carbohydrate feeding by a receptor antagonist PYX-2. Neuroreport 3: 1023–1026.
89. Besecke, L. M., Wolfe, A. M., Pierce, M. E., Takahashi, H. S. and Levine, J.E. (1994). Neuropeptide Y stimulates luteinizing horomone-releasing hormone release from superfused hypothalamic GT1–7 cells.
90. Balasubramaniam, A., Sheriff, S., Johnson, M. E., Prabhakaran, M., Huang, Y., Fischer, J. E., and Chance, W. T. (1994) [D-Trp$^{32}$] Neuropeptide Y: A competitive antagonist of NPY in rat hypothalamus. J. Med. Chem. 37: 811–815 (1994).
91. Walker, M. W., and Miller, R. J. (1988) $^{125}$I-neuropeptide Y and $^{125}$I-peptide YY bind to multiple receptor sites in rat brain. Mol. Pharmac. 34: 779–792.
92. Adham, N., Ellerbrock, B., Hartig, P., Weinshank, R. L., and Brandchek, T. (1993). Receptor reserve masks partial agonist activity of drugs in a cloned rat 5-hydroxytryptamine$_{1B}$ receptor expression system. Mol. Pharmacol. 43: 427–433.
93. Larhammar, D., Blomqvist, A. G>, and Wahlestedt, C. (1993). The receptor revolution—multiplicity of G-protein coupled receptrs. Drug design and discovery 9: 179–188.
94. Dumont, Y., A. Fournier, S. St-Pierre, and R. Quirion (1993) Comparative characterization and autoradiographic distribution of neuropeptide Y receptor subtypes in the rat brain. J.Neurosci. 13:73–76.
95. Singh, G., Singh, L., and Raufman, J.-P. (1992). Y2 receptors for peptide YY and neuropeptide Y on dispersed chief cells from guinea pig stomach. Am. J. Physiol. 262: G756–G762.
96. Cox, H. M., Cuthbert, A. W., Hakanson, R., and Wahlestedt, C. (1988). The effect of neuropeptide Y and peptdie Yy on electrogenic ion transport in rat intestinal epithelia. J. Physiol. Lond. 398: 65–80.
97. Lacroix, J. S., Stjarne, P., Angaard, a., and Lundberg, J. M. (1988). Sympathetic vascular control of the pig nasal mucosa (2): reserpine-resistant, non-Oadrenergic nervous response in relation to neuropeptide Y and ATP. Acta Physiol. Scand. 133: 183–197.
98. Lacroix, J. S., Angaard, A., Hokfelt, T., O'Hare, M. M., Fahrenkrug, J., and Lundberg, J. M. (1990). Neuropeptide Y: presence in sympathetic and parasympathetic innervation of the nasal mucosa. Cell Tissue Res. 259: 119–128.
99. Haung, S. C., and Tsai, M.-F. (1994). Receptors for peptide YY and neuropeptide Y on guinea pig pancreatic acinin. Peptides 15: 405–410.
100. De Qindt, M. E. and P. C. Emson (1986) Distribution of neuropeptide Y-like immunoreactivity in the rat central nervous system-II. Immunohistochemical analysis. Neurosci. 18:545–618.
101. Gustafson, E. L., J. P. Card, and R. Y. Moore (1986) Neuropeptide Y localization in the rat amygdaloid complex. J. Comp. Neuro. 251:349–362.

102. Siegel, A. H. Edinger, and S. Ohgami (1974) the topographic organization of the hippocampal projection to the septal area: A coparative neuronatomical analysis in the gerbil, rat, rabbit, and cat. J. Comp. Neuro. 157:359–378.
103. Lynch, D. R., M. W. Walker, R. J. Miller, and S. H. Snyder (1989) Neuropeptide Y receptor binding sites in rat brain: Differential autoradiographic localizations with $^{125}$I-peptide YY and $^{125}$I-neuropeptide Y imply receptor heterogeneity. J. Neurosci. 9:2607–2619.
104. Bai, F. L., M. Yamano, Y. Shiotani, P. C. Emson, A. D. Smith, J. F. Powell, and M. Tohyama (1985) An arcuato-paraventricular and -dorsomedial hypothalamic neuropeptide Y-containing system with lacks noradrenaline in the rat. Brain Res. 331:172–175.
105. Gustafson, E. L. and R. Y. Moore (1987) Noradrenaline and neuropeptide Y innervation of the rat hypothalamus are differentially affected by 6-hydroxydopamine. Neurosci.Lett. 83:53–58.
106. Mikkelsen, J. D. and P. J. Larsen (1992) A high concentration of NPY (Y1) -receptor mRNA-expressing cells in the rat arcuate nucleus. Neurosci.Lett. 148:195–198.
107. Larsen. P. J., S. P. Sheikh, C. R. Jakobsen, T. W. Schwartz, and J. D. Mikkelsen (1993) Regional distribution of putative NPY $Y_1$ receptors and neurons expressing $Y_1$ mRNA in forebrain areas of the rat central nervous system. Eur.J. Neurosci. 5:1622–1637.
108. Colmers, W. F. and D. Bleakman (1994) Effects of neuropeptide Y on the electrical properties of neurons. Trends Neurosci. 17:373–379.
109. Hall, J. M., Caulfield, M. P., Watson, S. P., and Guard, S. (1993) Receptor subtypes or species homologues: relevance to drug discovery, Trends Pharmacol. 14: 376–383.
110. Birnbaumer, L. (1990) Transduction of receptor signal into modulation of effector activity by G proteins: the first 20 years or so . . . FASEB J. 4: 3178–3188.
111. Morley, J. E. and Flood, J. F. (1991). Neuropeptide Y and memory processing. Ann. N.Y. Acad. Sci. 611: 226–231.
112. Cox, H. and Cuthbert, A. W. (1990) The effects of neuropeptide Y and its fragments upon basal and electrically stimulated ion secretion in rat jejunum mucosa. Br. J. Pharmac. 101: 247–252.

---

---

What is claimed is:

1. A process for identifying a chemical compound which specifically binds to a human or rat Y2 receptor, which comprises contacting nonneuronal cells transfected with a vector comprising DNA encoding, and expressing on their cell surface, (i) a human Y2 receptor, wherein the human Y2 receptor has the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with the chemical compound under conditions suitable for binding, and detecting specific binding of the chemical compound to the human or rat Y2 receptor.

2. A process for identifying a chemical compound which specifically binds to a human or rat Y2 receptor, which comprises contacting a membrane fraction from a cell extract of nonneuronal cells transfected with a vector comprising DNA encoding, and expressing on their cell surface, (i) a human Y2 receptor, wherein the human Y2 receptor has the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with the chemical compound under conditions suitable for binding, and detecting specific binding of the chemical compound to the human or rat Y2 receptor.

3. A process involving competitive binding for identifying a chemical compound which specifically binds to a human or rat Y2 receptor, which comprises separately contacting nonneuronal cells transfected with a vector comprising DNA encoding, and expressing on their cell surface, (i) a human Y2 receptor, wherein the human Y2 receptor has the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with both the chemical compound and a second chemical compound known to bind to the human or rat Y2 receptor, and with only the second chemical compound, under conditions suitable for binding of both compounds, and detecting specific binding of the chemical compound to the human or rat Y2 receptor, a decrease in binding of the second chemical compound to the human or rat Y2 receptor in the presence of the chemical compound indicating that the chemical compound binds to the human or rat Y2 receptor.

4. A process involving competitive binding for identifying a chemical compound which specifically binds to a human or rat Y2 receptor, which comprises separately contacting a membrane fraction from a cell extract of nonneuronal cells transfected with a vector comprising DNA encoding, and expressing on their cell surface, (i) a human Y2 receptor, wherein the human Y2 receptor has the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with both the chemical compound and a second chemical compound known to bind to the human or rat Y2 receptor, and with only the second chemical compound, under conditions suitable for binding of both compounds, and detecting specific binding of the chemical compound to the human or rat Y2 receptor, a decrease in binding of the second chemical compound to the human or rat Y2 receptor in the presence of the chemical compound indicating that the chemical compound binds to the human or rat Y2 receptor.

5. A process for determining whether a chemical compound specifically binds to and activates a human or rat Y2 receptor, which comprises contacting nonneuronal cells producing a second messenger response and transfected with a vector comprising DNA encoding, and expressing on their cell surface (i) a human Y2 receptor having the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with the chemical compound under conditions suitable for activation of the human or rat Y2 receptor, and measuring the second messenger response in the presence and in the absence of the chemical compound, a change in second messenger response in the presence of the chemical compound indicating that the chemical compound activates the human or rat Y2 receptor.

6. A process for determining whether a chemical compound specifically binds to and activates a human or rat Y2 receptor, which comprises contacting a membrane fraction from a cell extract of nonneuronal cells producing a second messenger response and transfected with a vector comprising DNA encoding, and expressing on their cell surface (i) a human Y2 receptor having the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with the chemical compound under conditions suitable for activation of the human or rat Y2 receptor, and measuring the second messenger response in the presence and in the absence of the chemical compound, a change in second messenger response in the presence of the chemical compound indicating that the chemical compound activates the human or rat Y2 receptor.

7. A process for determining whether a chemical compound specifically binds to and inhibits activation of a human or rat Y2 receptor, which comprises separately contacting nonneuronal cells producing a second messenger response and transfected with a vector comprising DNA encoding, and expressing on their cell surface (i) a human Y2 receptor having the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with both the chemical compound and a second chemical compound known to activate the human or rat Y2 receptor, and with only the second chemical compound, under conditions suitable for activation of the human or rat Y2 receptor, and measuring the second messenger response in the presence of only the second chemical compound and in the presence of both the second chemical compound and the chemical compound, a smaller change in second messenger response in the presence of both the chemical compound and the second chemical compound than in the presence of only the second chemical compound indicating that the chemical compound inhibits activation of the human or rat Y2 receptor.

8. A process for determining whether a chemical compound specifically binds to and inhibits activation of a human or rat Y2 receptor, which comprises separately contacting a membrane fraction from a cell extract of nonneuronal cells producing a second messenger response and transfected with a vector comprising DNA encoding, and expressing on their cell surface (i) a human Y2 receptor having the amino acid sequence shown in FIG. 2 (SEQ ID NO: 2) or (ii) a rat Y2 receptor, wherein the rat Y2 receptor has the amino acid sequence shown in FIG. 8 (SEQ ID NO: 4), with both the chemical compound and a second chemical compound known to activate the human or rat Y2 receptor, and with only the second chemical compound, under conditions suitable for activation of the human or rat Y2 receptor, and measuring the second messenger response in the presence of only the second chemical compound and in the presence of both the second chemical compound and the chemical compound, a smaller change in second messenger response in the presence of both the chemical compound and the second chemical compound than in the presence of only the second chemical compound indicating that the chemical compound inhibits activation of the human or rat Y2 receptor.

9. The process of either of claims 5 or 6, wherein the second messenger response comprises adenylate cyclase activity and the change in second messenger response is a decrease in adenylate cyclase activity.

10. The process of either of claims 7 or 8, wherein the second messenger response comprises adenylate cyclase activity and the change in second messenger response is a smaller decrease in the level of adenylate cyclase activity in the presence of both the chemical compound and the second chemical compound than in the presence of only the second chemical compound.

11. The process of claim 5, wherein the second messenger response comprises intracellular calcium levels and the change in second messenger response is an increase in intracellular calcium levels.

12. The process of claim 7, wherein the second messenger response comprises intracellular calcium levels and the change in second messenger response is a smaller increase in the level of intracellular calcium in the presence of both the chemical compound and the second chemical compound than in the presence of only the second chemical compound.

13. The process of any one of claims 1, 2, 3, 4, 5, 6, 7, 8, 9, 10, 11, or 12, wherein the nonneuronal cell is a mammalian cell.

14. The process of claim 13, wherein the mammalian cell is a COS-7 cell, an NIH-3T3 cell, a 293 human embryonic kidney cell, or an LM(tk–) cell.

* * * * *

UNITED STATES PATENT AND TRADEMARK OFFICE
CERTIFICATE OF CORRECTION

PATENT NO.   : 5,989,834
DATED        : November 23, 1999
INVENTOR(S)  : Christophe Gerald et al.

It is certified that error appears in the above-identified patent and that said Letters Patent is hereby corrected as shown below:

Title page, Item [54], and Column 1, line 1,
Title, change "USES OF NUCLEIC ACID ENCODING NEUROPEPTIDE Y/PEPTIDE YY (Y2) RECEPTORS NUCLEIC ACID ENCODING" to
-- USES OF NUCLEIC ACID ENCODING NEUROPEPTIDE Y/PEPTIDE YY (Y2) RECEPTORS --

Column 5,
Line 10, change "$B=B_1*(1-e^{-(kobs1*t)}) =B_2* (1-e^{-(kobs2*t)})$" to -- $B=B_1*(1-e^{-(kobs1*t)})+B_2*(1-e^{-(kobs2*t)})$ --

Column 24,
Line 41, change "25Xtotal" to -- 25X total --

Column 26,
Line 44, change "KH2PO$_4$" to -- $KH_2PO_4$ --

Column 28,
Line 5, change
"(5'-CTGGGTA GT-GGTCATTTGCAGCTCCAGGACTGACATGGTTCTT - 3')" to
-- (5' - CTGATGGTAGTGGTCATTTGCAGCTCCAGGACTGACATGGTTCTT -3') --

Column 33,
Line 31, change "PYY3-36" to -- $PYY_{3-36}$ --

Column 50,
Line 46, change "6-opioid receptor" to -- δ-opioid receptor --

Column 52,
Line 64, change "diarrhoea" to -- diarrhea --

UNITED STATES PATENT AND TRADEMARK OFFICE
CERTIFICATE OF CORRECTION

PATENT NO.    : 5,989,834
DATED         : November 23, 1999
INVENTOR(S)   : Christophe, Gerald et al.

It is certified that error appears in the above-identified patent and that said Letters Patent is hereby corrected as shown below:

Column 53,
Line 59, change "brainin" to -- brain in --

Column 54,
Line 47, change "peptdie" to -- peptide --

Column 55,
Sequence Listing, under (1) General Information, all of the following needs to be inserted:

-- (i) APPLICANT: Synaptic Pharmaceutical Corporation (ii) TITLE OF INVENTION: USES OF NUCLEIC ACID ENCODING NEUROPEPTIDE Y/PEPTIDE YY (Y2) RECEPTORS (iv) CORRESPONDENCE ADDRESS:
- (A) ADDRESSEE: Cooper & Dunham LLP
- (B) STREET: 1185 Avenue of the Americas
- (C) CITY: New York
- (D) STATE: New York
- (E) COUNTRY: U.S.A
- (F) ZIP: 10036

(v) COMPUTER READABLE FORM:
- (A) MEDIUM TYPE: Floppy disk
- (B) COMPUTER: IBM PC compatible
- (C) OPERATING SYSTEM: PC-DOS/MS-DOS
- (D) SOFTWARE: PatentIn Release #1.0, Version #1.30

(vi) CURRENT APPLICATION DATA:
- (A) APPLICATION NUMBER: 08/687,355
- (B) FILING DATE: November 26, 1996
- (C) CLASSIFICATION:

UNITED STATES PATENT AND TRADEMARK OFFICE
CERTIFICATE OF CORRECTION

PATENT NO. : 5,989,834
DATED : November 23, 1999
INVENTOR(S) : Christophe, Gerald et al.

It is certified that error appears in the above-identified patent and that said Letters Patent is hereby corrected as shown below:

(viii) ATTORNEY/AGENT INFORMATION:
    (A) NAME: White, John P.
    (B) REGISTRATION NUMBER: 28,678
    (C) REFERENCE/DOCKET NUMBER: 44742-A-PCT/JPW/MAT (ix) TELECOMMUNICATION INFORMATION:
    (A) TELEPHONE: 212-278-0400
    (B) TELEFAX: 212-391-0525

Column 69,
Sequence Listing, under (2) INFORMATION FOR SEQ. ID NO:6:, (i) SEQUENCE CHARACTERISTICS:, change "(A) LENGTH: 381 amino acids" to -- (A) LENGTH: 382 amino acids --.

Column 71,
Sequence Listing, last line of the continuation of SEQUENCE DESCRIPTION: SEQ ID NO:6: after the sequence "Thr Asn Val", insert -- * --

Signed and Sealed this

Twelfth Day of March, 2002

Attest:

JAMES E. ROGAN
*Director of the United States Patent and Trademark Office*

*Attesting Officer*